(12) United States Patent
Greenfield et al.

(10) Patent No.: US 7,303,876 B2
(45) Date of Patent: Dec. 4, 2007

(54) COMPOSITIONS, METHODS, AND KITS FOR ISOLATING NUCLEIC ACIDS USING SURFACTANTS AND PROTEASES

(75) Inventors: Lawrence Greenfield, San Mateo, CA (US); Luz Montesclaros, Pittsburg, CA (US)

(73) Assignee: Applera Corporation, Foster City, CA (US)

( * ) Notice: Subject to any disclaimer, the term of this patent is extended or adjusted under 35 U.S.C. 154(b) by 243 days.

(21) Appl. No.: 10/800,137

(22) Filed: Mar. 11, 2004

(65) Prior Publication Data

US 2005/0009045 A1    Jan. 13, 2005

Related U.S. Application Data

(63) Continuation of application No. 09/997,169, filed on Nov. 28, 2001, now Pat. No. 6,762,027, which is a continuation-in-part of application No. 09/724,613, filed on Nov. 28, 2000, now Pat. No. 7,001,724.

(51) Int. Cl.
  *C12Q 1/68*    (2006.01)
  *C12N 1/00*    (2006.01)
  *C07H 21/02*   (2006.01)
  *C07H 23/00*   (2006.01)
  *C07H 19/06*   (2006.01)

(52) U.S. Cl. .................. 435/6; 435/243; 536/23.1; 536/26.42; 536/27.21

(58) Field of Classification Search ............... 435/6, 435/243; 536/23.1, 26.42, 27.21
See application file for complete search history.

(56) References Cited

U.S. PATENT DOCUMENTS

| | | | |
|---|---|---|---|
| 4,481,294 | A | 11/1984 | Downs |
| 4,900,677 | A | 2/1990 | Hewitt |
| 4,943,530 | A | 7/1990 | Christner et al. |
| 5,010,183 | A | 4/1991 | Macfarlane |
| 5,130,423 | A | 7/1992 | Van Ness et al. |
| 5,300,635 | A | 4/1994 | Macfarlane |
| 5,596,092 | A | 1/1997 | Schneider |
| 5,728,822 | A | 3/1998 | Macfarlane |
| 6,242,188 | B1 | 6/2001 | Dattagupta et al. |
| 6,342,387 | B1 | 1/2002 | Hayashizaki et al. |
| 6,548,256 | B2 | 4/2003 | Lienau et al. |
| 6,762,027 | B2 | 7/2004 | Greenfield et al. |
| 7,001,724 | B1 | 2/2006 | Greenfield et al. |

FOREIGN PATENT DOCUMENTS

| | | |
|---|---|---|
| DE | 199 37 607 A1 | 2/2001 |

(Continued)

OTHER PUBLICATIONS

Official Action in Japanese Patent Application No. JP 2002-587600 mailed on Sep. 20, 2005.

(Continued)

*Primary Examiner*—Jezia Riley
(74) *Attorney, Agent, or Firm*—Finnegan, Henderson, Farabow, Garrett & Dunner, LLP; Scott R. Bortner

(57) ABSTRACT

The invention relates to compositions and methods for isolating nucleic acids from biological samples, including whole tissue. The invention also provides kits for isolating nucleic acids from biological samples.

23 Claims, 33 Drawing Sheets

FOREIGN PATENT DOCUMENTS

| EP | 0953635 A1 | 11/1999 |
| --- | --- | --- |
| EP | 1 018 549 A1 | 7/2000 |
| EP | 1044984 A2 | 10/2000 |
| JP | 06-205676 A | 7/1994 |
| JP | 07-143879 A | 6/1995 |
| JP | 11-92494 A | 4/1999 |
| JP | 11-332562 A | 12/1999 |
| WO | WO95/15970 | 6/1995 |
| WO | WO98/04730 | 2/1998 |
| WO | WO98/20164 | 5/1998 |
| WO | WO 01/10554 A2 | 2/2001 |

OTHER PUBLICATIONS

English Translation of Official Action in Japanese Patent Application No. JP 2002-587600 mailed on Sep. 20, 2005, provided by Shusaku Yamamoto Patent Law Offices, Osaka, Japan.

U.S. Appl. No. 09/724,613, filed Nov. 28, 2000.

Restriction Requirement dated Mar. 1, 2002, in U.S. Appl. No. 09/724,613, filed Nov. 28, 2000.

Response dated Apr. 30, 2002, in U.S. Appl. No. 09/724,613, filed Nov. 28, 2000.

Office Action dated May 31, 2002, in U.S. Appl. No. 09/724,613, filed Nov. 28, 2000.

Response dated Aug. 30, 2002, in U.S. Appl. No. 09/724,613, filed Nov. 28, 2000.

Office Action dated Oct. 21, 2002, in U.S. Appl. No. 09/724,613, filed Nov. 28, 2000.

Amendment dated Mar. 21, 2003, in U.S. Appl. No. 09/724,613, filed Nov. 28, 2000.

Final Office Action dated Apr. 30, 2003, in U.S. Appl. No. 09/724,613, filed Nov. 28, 2000.

Amendment After Final dated Jul. 30, 2003, in U.S. Appl. No. 09/724,613, filed Nov. 28, 2000.

Office Action dated Sep. 3, 2003, in U.S. Appl. No. 09/724,613, filed Nov. 28, 2000.

Amendment filed Feb. 27, 2004, in U.S. Appl. No. 09/724,613, filed Nov. 28, 2000.

Office Action dated Apr. 15, 2004, in U.S. Appl. No. 09/742,613, filed Nov. 28, 2000.

Amendment and Response to Final Office Action dated Jul. 15, 2004, in U.S. Appl. No. 09/724,613, filed Nov. 28, 2000.

Office Action dated Nov. 8, 2004, in U.S. Appl. No. 09/724,613, filed Nov. 28, 2000.

Chapdelaine, P. et al., "A One-Hour Procedure for the Preparation of Genomic DNA from Frozen Tissues," *BioTechniques*, 14(2):163-164, 1993.

Colosi, J. C. et al., "Tissue Grinding with Ball Bearings and Vortex Mixer for DNA Extraction," *Nucleic Acid Research*, 21(4):1051-1052, 1993.

Dry, P.J., "A Quick and Easy Method for the Purification of DNA From Chorionic Villus Samples," *Nucleic Acids Research*, 16(15):7730, 1988.

Fischer, J. A., "Activity of Proteinase K and RNase in Guanidinium Thiocyanate," *Techniques in Molecular Biology and Cloning*, Abstract 4823, FASEB Journal, 1988.

Goldenberger, D. et al., "A Simple 'Universal' DNA Extraction Procedure Using SDS and Proteinase K is Compatible with Direct PCR Amplification," *PCR Methods and Applications*, 4:368-370, 1995.

Lai, C.-C. et al., "Improved Proteinase K Digestion for the Rapid Isolation of mRNA from Mammalian Tissues," *BioTechniques*, 15(4):620-624, 1993.

Laird, P. W. et al., "Simplified Mammalian DNA Isolation Procedure," *Nucleic Acids Research*, 19(15):4293, 1991.

Macfarlane, D. E. et al., "Isolating RNA from Clinical Samples With Catrimox-14 and Lithium Chloride," *Journal of Clinical Laboratory Analysis*, 11:132-139, 1997.

Macfarlane, D. E. et al., "Isolating RNA from Whole Blood—The Dawn of RNA-Based Diagnosis," *Nature*, 362:186-188, 1993.

Wilson, K., "Preparation of Genomic DNA from Bacteria" in *Current Protocols in Molecular Biology*, Vol. 1, F.M. Ausbel et al. (Eds.), John Wiley & Sons, Inc., NY, pp. 2.4.1-2.4.5, 1994.

Richards, E., "Preparation of Genomic DNA from Plant Tissue" in *Current Protocols in Molecular Biology*, Vol. 1, F.M. Ausbel et al. (Eds.), John Wiley & Sons, Inc., NY, pp. 2.3.3-2.3.7, 1994.

Rauber, N. R. K. et al., "Ribonuclease A Digestion by Proteinase K," *Z. Naturforsch.*, 33 c:660-663, 1978.

Seibert, G. et al., "The Separation of High and Low Molecular Weight RNA by Precipitation with N-Cetyl-N,N,N-trimethylammoniumbromide," *Z. Naturforsch Sect. C. Biosci.*, 32(3-4):294-296, 1977.

Wiegers, U. et al., "A New Method using 'Proteinase K' to Prevent mRNA Degradation During Isolation from HeLa Cells," *Biochemical and Biophysical Research Communications*, 44(2):513-519, (1971).

International Search Report for PCT Application No. PCT/US01/45071, mailed Dec. 27, 2002.

Amendment and Response to Office Action, mailed Feb. 8, 2005, for U.S. Appl. No. 09/724,613, filed Nov. 28, 2000.

Final Office Action, mailed Apr. 15, 2005, for U.S. Appl. No. 09/724,613, filed Nov. 28, 2000.

Amendment and Response to Final Office Action, mailed Jul. 15, 2005, for U.S. Appl. No. 09/724,613, filed Nov. 28, 2000.

Notice of Allowance and Fee(s) Due and Examiner's Amendment, mailed Sep. 12, 2005, for U.S. Appl. No. 09/724,613, filed Nov. 28, 2000.

Office Action, mailed Jun. 25, 2002, for U.S. Appl. No. 09/997,169, filed Nov. 28, 2001.

Response, mailed Oct. 25, 2002 for U.S. Appl. No. 09/997,169, filed Nov. 28, 2001.

Final Office Action, mailed Dec. 12, 2002, for U.S. Appl. No. 09/997,169, filed Nov. 28, 2001.

Amendment After Final, mailed Mar. 12, 2003, for U.S. Appl. No. 09/997,169, filed Nov. 28, 2001.

Advisory Action, mailed Mar. 26, 2003, for U.S. Appl. No. 09/997,169, filed Nov. 28, 2001.

Interview Summary from interview conducted Apr. 10, 2003, for U.S. Appl. No. 09/997,169, filed Nov. 28, 2001.

Second Amendment After Final, mailed Apr. 14, 2003, for U.S. Appl. No. 09/997,169, filed Nov. 28, 2001.

Office Action, mailed Apr. 30, 2003, for U.S. Appl. No. 09/997,169, filed Nov. 28, 2001.

Amendment, mailed Oct. 30, 2003, for U.S. Appl. No. 09/997,169, filed Nov. 28, 2001.

Notice of Allowance and Fee(s) Due, mailed Dec. 12, 2003, for U.S. Appl. No. 09/997,169, filed Nov. 28, 2001.

Communication pursant to Article 96(2) EPC mailed Mar. 21, 2007, in European Patent Application No. 01 274 041.1 (5 pages).

Genomic DNA from 50 mg rat tail sections digested with 1 mg of Prot. K & 1% DTAB and bound onto GF/B and GF/D membranes under 3.75 M GuSCN and 4.5 % Tween 20. The gDNA was finally eluted with of 150 mL of 1X TE and 0.01 N NaOH solutions and 20 mL was used for gel electrophoresis (1 % agarose).

COMPOSITIONS, METHODS, AND KITS FOR ISOLATING NUCLEIC ACIDS USING SURFACTANTS AND PROTEASES

This application is a continuation of U.S. patent application Ser. No. 09/997,169, filed Nov. 28, 2001, now U.S. Pat. No. 6,762,027, which is a continuation-in-part of U.S. patent application Ser. No. 09/724,613, filed Nov. 28, 2000 now U.S. Pat. No. 7,001,724. The entire disclosures of U.S. patent application Ser. Nos. 09/997,169 and 09/724,613 are incorporated herein by reference and may be relied on for any purpose.

FIELD OF THE INVENTION

The invention relates to compositions and methods for releasing and isolating nucleic acids from biological samples, including whole tissue. The invention also provides kits for isolating and/or releasing nucleic acids from biological samples.

BACKGROUND OF THE INVENTION

Current methods for isolating nucleic acids from biological samples may include macerating tissues, lysing cells, and inactivating nucleases using chaotropic salts, such as guanidine hydrochloride or guanidinium thiocyanate, and a non-ionic detergent. The released nucleic acids then may be selectively precipitated from solution.

Various chemical disruption methods, using detergents, chaotropes, proteases, bile salts, organic solvents, and harsh acidic or basic conditions have been employed to macerate tissue and release nucleic acid. The nucleic acid obtained using such methods may be degraded due to long incubation times or exposure to harsh conditions.

SUMMARY OF THE INVENTION

In certain embodiments, compositions are provided for releasing nucleic acids from a biological sample. In certain embodiments, the compositions include at least one cationic surfactant, at least one protease, and a buffer.

In certain embodiments, methods for releasing nucleic acids from a biological sample are provided. In certain embodiments, methods for isolating nucleic acids from a biological sample are provided. In certain embodiments, these methods include combining the sample with at least one cationic surfactant, at least one protease, and a buffer to form a reaction composition. In certain embodiments, the reaction composition further comprises a second surfactant. In certain embodiments, the reaction composition further comprises a salt. In certain embodiments, the composition is incubated under appropriate conditions to release the nucleic acid from the biological sample. In certain embodiments, the released nucleic acid is then isolated.

In certain embodiments, kits for isolating and/or releasing nucleic acid from biological samples are also provided. In certain embodiments, the invention provides kits comprising at least one cationic surfactant and at least one protease. In certain embodiments, kits further comprise a second surfactant, a salt, organic extraction agent(s), organic precipitating agent(s), solubilizing agents(s), nucleic acid-binding solid phase(s), or combinations of these components.

According to certain embodiments, a method of obtaining nucleic acid from a biological sample and binding the nucleic acid to a solid phase is provided. In certain embodiments, this method comprises contacting the biological sample with a disrupting buffer, wherein the disrupting buffer comprises a protease and a cationic surfactant; and binding the nucleic acid to a solid phase. In certain embodiments, the method comprises contacting the biological sample with a disrupting buffer, wherein the disrupting buffer comprises a protease and a cationic surfactant; substantially neutralizing the cationic surfactant; and binding the nucleic acid to a solid phase.

According to certain embodiments, a kit is provided, comprising a protease, a cationic surfactant, and a second surfactant, wherein the second surfactant permits the binding of nucleic acid to a solid phase in the presence of the protease and cationic surfactant.

According to certain embodiments, a kit for obtaining nucleic acid from a biological sample is provided, comprising a protease; a cationic surfactant; a non-ionic surfactant, wherein the non-ionic surfactant permits the binding of nucleic acid to a solid phase in the presence of the protease and cationic surfactant; and a high salt buffer.

BRIEF DESCRIPTION OF THE FIGURES

FIG. 2 illustrates the effect of various surfactants on Proteinase K digestion of a dye-labeled casein substrate.

DETAILED DESCRIPTION OF THE EMBODIMENTS

Figure 1:
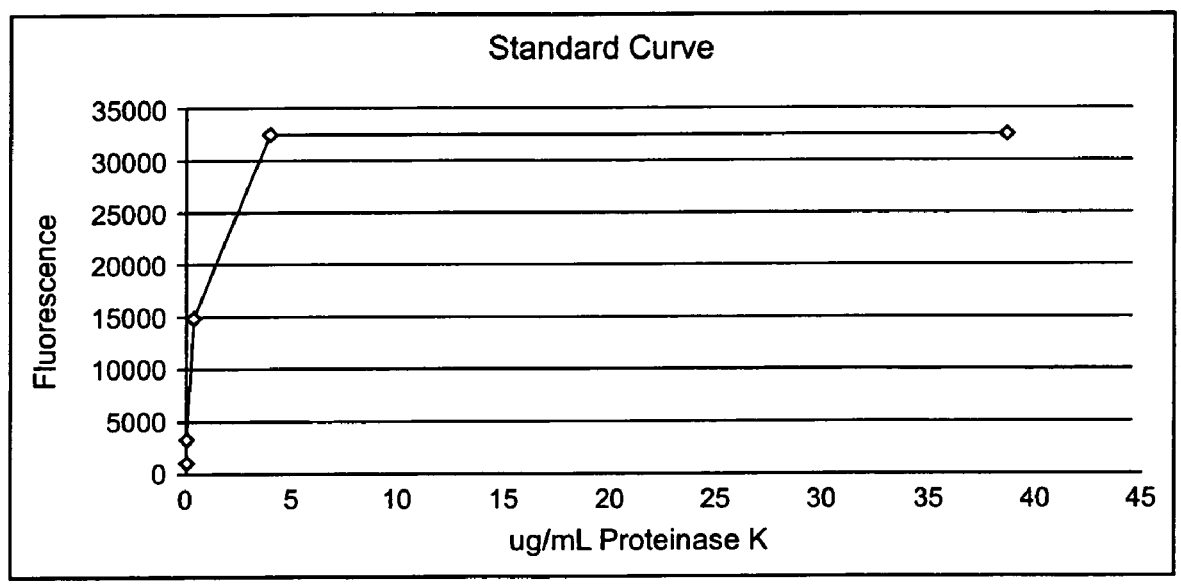
FIG. 1 represents the fluorescent intensity (measured in fluorescence units) of dye-labeled casein substrate incubated with Proteinase K at concentrations ranging from 40 fg/ml to 40 ug/ml.

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

Definitions

The term "alkyl group" refers to a hydrocarbon moiety based on a linear, branched or cyclic alkane. Linear alkanes are organic compounds with the general chemical formula $C_nH_{2n+2}$, where C represents a carbon atom, H represents a hydrogen atom, and n represents a whole number. Exemplary linear alkanes include, but are not limited to, methane ($CH_4$), ethane ($C_2H_6$), propane ($C_3H_8$), butane ($C_4H_{10}$), octane and the like. Exemplary branched alkanes include, but are not limited to, isobutane ($C_4H_{10}$), isopentane ($C_5H_{12}$), and the like. Exemplary cyclic alkanes include, but are not limited to, cyclobutane ($C_4H_8$), cyclohexane ($C_6H_{12}$), and the like. Exemplary alkyl groups include, but are not limited to, methyl (—$CH_3$), propyl (—$C_3H_7$), octyl (—$C_8H_{17}$), and the like. While alkanes are typically unreactive, alkyl groups can be combined with other molecules to form compounds. For example, isopropyl alcohol ($C_3H_7OH$) is an alcohol that contains a propyl group. A general discussion of alkyl groups and alkanes can be found, among other places, in Morrison and Boyd, Organic Chemistry, $3^{rd}$ Ed., Allyn and Bacon, Boston, Mass., 1973; and Vollhardt, Organic Chemistry, W. H. Freeman, New York, N.Y., 1987.

The term "aryl group" refers to a hydrocarbon moiety that is based on benzene or other aromatic compounds. Aryl groups, like alkyl groups, can be combined with other molecules to form compounds. A general discussion of aromatic compounds and aryl groups can be found, among other places, in Morrison and Boyd, Organic Chemistry, $3^{rd}$ Ed., Allyn and Bacon, Boston, Mass., 1973; and Vollhardt, Organic Chemistry, W. H. Freeman, New York, N.Y., 1987, particularly Chapter 19.

The term "biological sample" is used in a broad sense and is intended to include a variety of biological sources that contain nucleic acids. Such sources include, without limitation, whole tissues, including biopsy materials and aspirates; in vitro cultured cells, including primary and secondary cells, transformed cell lines, and tissue. and cellular explants; whole blood, red blood cells, white blood cells, and lymph; and body fluids such as urine, sputum, semen, secretions, eye washes and aspirates, lung washes and aspirates. Fungal and plant tissues, such as leaves, roots, stems, and caps, are also within the scope of the present invention. Microorganisms and viruses that may be present on or in a biological sample are within the scope of the invention. Bacterial cells are also within the scope of the invention.

The term "buffer," as used herein, refers to aqueous solutions or compositions that resist changes in pH when acids or bases are added to the solution. This resistance to pH change is due to the solution's buffering action. Solutions exhibiting buffering activity are referred to as buffers or buffer solutions. Buffers typically do not have an unlimited ability to maintain the pH of a solution or composition. Rather, typically they are able to maintain the pH within certain ranges, for example between pH 5 and pH 7. See, generally, C. Mohan, Buffers, A guide for the preparation and use of buffers in biological systems, Calbiochem, 1999. Exemplary buffers include, but are not limited to, MES ([2-(N-Morphilino)ethanesulfonic acid]), ADA (N-2-Acetamido-2-iminodiacetic acid), and Tris ([tris(Hydroxymethyl) aminomethane]; also known as Trizma); Bis-Tris; ACES; PIPES; MOPS; and the like (all available from Sigma).

Buffers that maintain the pH within a certain pH range, for example, between pH 5 and pH 7, and similar terms as used herein, are intended to encompass any buffer that exhibits buffering action at some point within the stated pH range. Thus, that term encompasses buffers that do not exhibit buffering capacity within the entire stated range, and buffers with buffering capacity that extend beyond the stated range. For example, solution A may exhibit buffering capacity between pH 5.2 and 6.7, solution B may exhibit buffering capacity between 6.0 and 8.0. For purposes of this invention, both of those solutions would be considered buffers that maintain the pH within the range of pH 5.0 to pH 7.0. The skilled artisan will be able to identify an appropriate buffer for maintaining the pH between a specified range using a buffer table. Buffer tables can be found in, among other places, the Calbiochem 2000-2001 General Catalog at pages 81-82, and the Sigma 2000-2001 Biochemicals and Reagents for Life Science Research Catalog at page 1873, both of which are expressly incorporated by reference.

The term "chaotrope" or "chaotropic salt," as used herein, refers to a substance that causes disorder in a protein or nucleic acid by, for example, but not limited to, altering the secondary, tertiary, or quaternary structure of a protein or a nucleic acid while leaving the primary structure intact. Exemplary chaotropes include, but are not limited to, guanidine hydrochloride, guanidinium thiocyanate, sodium thiocyanate, sodium iodide, sodium perchlorate, and urea. A typical anionic chaotropic series, shown in order of decreasing chaotropic strength, includes: CCl3COO—>>CNS—>CF3COO—>ClO4>I—>CH3COO—>Br—, Cl—, or CHO2—. Descriptions of chaotropes and chaotropic salts can be found, among other places, in Hamaguchi, Kozo and Geiduschek; E. Peter; Hatefi, Y. and Hanstein, W. G. (1962), "Solubilization of Particulate Proteins And Nonelectrolytes by Chaotropic Agents," Proc. Natl. Acad. Sci. 62: 1129-1136); The Effect Of Electrolytes On The Stability Of The Deoxyribonucleate Helix, J. Amer. Chem. Soc. 84: 1329-1338); and U.S. Pat. No. 5,234,809.

A "chelator" is a compound that is capable of binding to metal cations, such as sodium (Na+), magnesium (Mg++), or calcium (Ca++) ions. At least two non-metal ions of the chelator form coordinate bonds with the metal cation to incorporate it into the ring. Thus, the metal cation is no longer free to participate in some reactions. For example, a chelated metal may not be available to bind and activate proteins. Cations that have a single charge, such as Na+ are referred to as monovalent cations, while those with a double charge, such as Mg++ or Ca++, are referred to as divalent cations. Some enzymes, such as certain polymerases and nucleases typically function in the presence of free divalent cations. Thus, a divalent cation chelator, provided in sufficient amounts, may inhibit or reduce the activity of such divalent cation-dependent enzymes. Exemplary chelators include, but are not limited to, EDTA, EGTA, diaminoethane, and the like.

A "nuclease," such as a deoxyribonuclease (DNAse)or a ribonuclease (RNAse), is an enzyme that catalyzes the hydrolysis of phosphodiester linkages in nucleic acid polymers. Nucleases cause nucleic acid polymers to degrade, releasing constituent nucleotides and/or oligonucleotides (fragments of the polymers). A DNAse degrades DNA molecules and an RNAse degrades RNA molecules. Nuclease activity can typically be slowed or prevented by appropriate nuclease inhibitors. In certain embodiments, nucleases may be chemicals that degrade either RNA or DNA. Examples of such nucleases include, but are not limited to, phenanthroline-copper complexes; and the combination of iron, hydrogen peroxide, and ethylenediamine tetracetic acid.

As used herein, the term "organic solvent" refers to organic liquids, i.e., those comprising molecules with a hydrocarbon backbone. Organic solvents are capable of solvating non-solvent molecules, e.g., by surrounding them with solvent molecules so that the non-solvent molecules are dissolved in the solvent. Exemplary organic solvents include, but are not limited to, benzene, carbon tetrachloride, chloroform, phenol and other alcohols such as ethanol, methanol, and isopropanol (2-propanol), dimethyl sulfoxide (DMSO), and the like. Organic solvents can be used, for example, to extract nucleic acids from certain biochemical compositions, or to precipitate nucleic acids from aqueous solutions. Discussions of organic solvents can be found, among other places, in Morrison & Boyd, Organic Chemistry, 3d Edition, Allyn & Bacon, Boston, Mass., 1973.

As used herein, the term "protease" refers to an enzyme that catalyzes the cleavage of peptide bonds, e.g., in proteins, polypeptides, oligopeptides, and peptides (collectively "peptides"). Exemplary proteases include, but are not limited to, subtilisins, subtilases, and alkaline serine proteases. Subtilases are a family of serine proteases, i.e., enzymes that utilize a serine in their active site for cleavage. Subtilases are found in prokaryotic and eukaryotic organisms, such as, bacteria, fungi, yeast, and other phyla. Subtilisins are bacterial serine proteases that have broad substrate specificities. Subtilisins are relatively resistant to denaturation by chaotropes, such as urea and guanidine hydrochloride, and anionic surfactants, such as sodium dodecyl sulfate (SDS). Exemplary subtilisins include, but are not limited to: Proteinase K; Proteinase R; Proteinase T (isolated from *Tritirachium album* Limber); Subtilisin DY, Carlsberg, also referred to as Subtilisin, Subtilisin A, Subtilopeptidase A, or Alcalase Novo; BPN', also referred to as Nagarse proteinase, Nagarse, or Subtilopeptidase C; Novo, also referred to as Bacterial proteinase Novo, Subtilisin B, or Subtilopeptidase B; mesentericopeptidase; and Thermitase.

Discussions of subtilases, subtilisins, Proteinase K, and other proteases may be found, among other places, in Genov et al., (1995) Stability Of Subtilisins And Related Proteinases (Subtilases), Int. J. Peptide Protein Res. 45: 391-400); Narhi and Arakawa (1989) Sodium Dodecyl Sulfate Polyacrylamide Gel Electrophoresis As A Method For Studying The Stability Of Subtilisin, Biochimica et Biophysica Acta. Vol. 990:144-149); Dixon and Webb, Enzymes, 3d Edition, Academic Press, New York, N.Y. (1979); and Creighton, Proteins: Structures and Molecular Principles, W. H. Freeman and Co., New York, N.Y. (1984).

The term "salt" as used herein, refers to a compound produced by the interaction of an acid and a base. Exemplary salts include, but are not limited to, sodium chloride, potassium phosphate, and sodium bicarbonate. In water and other aqueous solutions, salts typically dissociate into an "anion," or negatively charged subcomponent, and a "cation," or positively charge subcomponent. For example, when sodium chloride (NaCl) is dissolved in water, it dissociates into a sodium cation (Na+) and a chloride anion (Cl—).

As used herein, the term "surfactant" refers to a surface-active agent that generally comprises a hydrophobic portion and a hydrophilic portion. Examples of surfactants include, but are not limited to, detergents and bile acid salts. (See, e.g., Bhairi, A Guide to the Properties and Uses of Detergents in Biological Systems, Calbiochem-Novabiochem Corp. 1997). Surfactants may be categorized as anionic, nonionic, zwitterionic, or cationic, depending on whether they comprise one or more charged group. Anionic surfactants, such as SDS or lauryl sarkosine, contain a negatively charged group and have a net negative charge. Nonionic surfactants contain non-charged polar groups and have no charge. Exemplary nonionic surfactants include, but are not limited to, t-octylphenoxypolyethoxyethanol (Triton X-100), polyoxyethylenesorbitan monolaurate (Tween 20), polyoxyethylenesorbitan monolaurate (Tween 21), polyoxyethylenesorbitan monopalmitate (Tween. 40), polyoxyethylenesorbitan monostearate (Tween 60), polyoxyethylenesorbitan monooleate (Tween 80), polyoxyethylenesorbitan monotrioleate (Tween 85), (octylphenoxy)polyethoxyethanol (IGEPAL CA-630/NP-40), triethyleneglycol monolauryl ether (Brij 30), and sorbitari monolaurate (Span 20). A zwitterionic surfactant contains both a positively charged group and a negatively charged group, and has no net charge.

A "cationic surfactant" has a positively charged group under the conditions examined. Cationic surfactants may contain quaternary amines or tertiary amines. Exemplary quaternary amine surfactants include, but are not limited to, cetylpyridinium chloride, cetyltrimethylammonium bromide (CTAB; Calbiochem #B22633 or Aldrich #85582-0), cetyltrimethylammonium chloride (CTACl; Aldrich #29273-7), dodecyltrimethylammonium bromide (DTAB, Sigma #D-8638), dodecyltrimethylammonium chloride (DTACl), octyl trimethyl ammonium bromide, tetradecyltrimethylammonium bromide (TTAB), tetradecyltrimethylammonium chloride (TTACl), dodecylethyldimethylammonium bromide (DEDTAB), decyltrimethylammonium bromide (D10TAB), dodecyltriphenylphosphonium bromide (DTPB), octadecylyl trimethyl ammonium bromide, stearoalkonium chloride, olealkonium chloride, cetrimonium chloride, alkyl trimethyl ammonium methosulfate, palmitamidopropyl trimethyl chloride, quaternium 84 (Mackernium NLE; Mcintyre Group, Ltd.), and wheat lipid epoxide (Mackernium WLE; Mcintyre Group, Ltd.). Exemplary ternary amine surfactants include, but are not limited to, octyldimethylamine, decyldimethylamine, dodecyldimethylamine, tetradecyidimethylamine, hexadecyldimethylamine, octyldecyldimethylamine, octyldecylmethylamine, didecylmethylamine, dodecylmethylamine, triacetylammonium chloride, cetrimonium chloride, and alkyl dimethyl benzyl ammonium chloride. Additional classes of cationic surfactants include, but are not limited to, phosphonium, imidzoline, and ethylated amine groups.

Alkyl amine oxides represent a class of surfactants that are typically cationic at a lower pH but are nonionic at a neutral pH. The general structure is as follows:

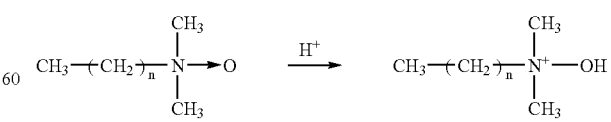

where n represents a number between 1 and 30. Examples include, but are not limited to, hexadecylamine oxide, tetradecylamine oxide, dodecylamine oxide, and decylamine oxide.

The term "whole tissue" according to the present invention is used in the broad sense to include any collection of cells from a single organism. Examples of tissues include, without limitation, muscles, including cardiac, striated, and smooth muscle; organs, such as kidney, liver, spleen, and heart; nerves; dermal and epidermal layers, such as skin; blood; connective tissue such as bone, cartilage, ligaments, and tendons; and the like. Fragments, pieces, sections, slices, and sub-components of whole tissues are within the scope of the invention. The term whole tissue is not limited, for example, to an entire organ or bone. Any aggregate or assembly of cells at any level is, for purposes of this invention, considered whole tissue. Fungal and plant tissues, such as leaves, roots, stems, and caps, are also within the scope of the present invention.

The term "nucleic acid," as used herein, refers to a polymer of ribonucleosides or deoxyribonucleosides comprising phosphodiester linkages between subunits. Such nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Solid phase components (also called solid phases or solid phase supports) that are capable of binding to nucleic acids released from a biological sample include a variety of materials that are capable of binding nucleic acids under suitable conditions. Exemplary solid phase components include, but are not limited to, silica particles, silicon dioxide, diatomaceous earth, glass, alkylsilica, aluminum silicate, borosilicate, nitrocellulose, diazotized paper, hydroxyapatite, nylon, metal oxides, zirconia, alumina, diethylaminoethyl- and triethylaminoethyl-derivatized supports (Chromegabond SAX, LiChrosorb-AN, Nucleosil SB, Partisil SAX, RSL Anion, Vydac TP Anion, Zorbax SAX, Nucleosil NMe2, Aminex A-series, Chromex, and Hamilton HA Ionex SB, DEAE sepharose, QAE sepharose), and hydrophobic chromatography resins (such phenyl- or octyl-sepharose).

Certain polymers, under appropriate conditions, are capable of precipitating nucleic acids from solution. Some polymers are capable of forming a nucleic acid-polymer complex that has a low solubility or is insoluble, so that complexed nucleic acid may precipitate. Examples of polymers that form such complexes with nucleic acids include, but are not limited to, polyethyleneimine, DEAE dextran, polylysine, polyarginine, polyhistidine, other weakly basic polymers (described in, among other places, U.S. Pat. Nos. 5,582,988; 5,733,762; 5,622,822; and 5,599,667), and the like. Other polymers, such as polyethylene glycol, bind significant amounts of water in a solution, which may also cause nucleic acids to precipitate from the solution.

According to certain embodiments, methods of releasing nucleic acid from a biological sample and binding the nucleic acid to a solid phase includes "substantially neutralizing" a cationic surfactant. The term "substantially neutralizing" the cationic surfactant, for the purposes of this application, means that more nucleic acid in a sample is capable of binding a solid phase with such substantial neutralization than without the neutralization. According to certain embodiments, the substantial neutralizing of the cationic surfactant may be accomplished by reducing, inhibiting, or preventing one or more effects of the cationic surfactant. In certain embodiments, these effects may include one or more of the following: precipitation of nucleic acid by the cationic surfactant, binding of the cationic surfactant to nucleic acid, blocking of binding of nucleic acid to a solid phase, and interacting with the solid-phase resulting in interfering with binding of the nucleic acid. Not all of these effects are necessarily present in all the embodiments of the invention. According to certain embodiments, substantially neutralizing the cationic detergent is accomplished by the conditions in the disrupting buffer, and do not necessarily comprise a separate step from contacting the biological sample with the disrupting buffer.

In certain embodiments, "substantially neutralizing" a cationic surfactant may include, but is not limited to, at least one of adding a reagent which substantially neutralizes the cationic surfactant, precipitating the cationic surfactant, removing the cationic surfactant by phase extraction, removing the cationic surfactant by dialysis, binding the cationic surfactant to a solid phase, and removing the cationic surfactant by other methods. In certain embodiments, reagents which substantially neutralize the cationic surfactant include, but are not limited to, chaotropes, nonionic surfactants, anionic surfactants, and zwitterionic surfactants.

The term "disrupting buffer," as used herein, referes to a buffer that is used in a process of releasing cells from tissue, a process of breaking open cells, or a process of releasing cells from tissue and breaking open cells.

Exemplary Embodiments

In certain embodiments, the present invention is directed to compositions, methods, and kits for isolating nucleic acid from biological samples, preferably whole tissue. In certain embodiments, the compositions, methods, and kits of the invention reduce the time needed for sample preparation, decrease potential safety risks posed by multi-step procedures that require repeated sample manipulation, and/or provide high integrity (i.e., minimally degraded) high molecular weight nucleic acid. In certain embodiments, the compositions, methods, and kits of the invention obviate the need for additional equipment to physically or mechanically disrupt tissue.

The compositions and kits comprise, and the methods employ, surfactants and proteases. In certain embodiments, the biological sample is combined with at least one cationic surfactant and at least one protease to form a reaction composition. In certain embodiments, the reaction composition is then incubated in a manner such that nucleic acids are released from the biological samples. For example, in certain embodiments, during incubation, these reaction. compositions typically can: (i) macerate or disaggregate the biological sample; (ii) lyse the cells comprising the sample; (iii) sterilize the sample; (iv) neutralize or inactivate nucleases; and (v) release nucleic acids from the biological sample.

While Proteinase K alone typically will effectively macerate whole tissue when incubated for approximately 12-18 hours, the released nucleic acid is frequently highly degraded. This degradation is due, at least in part, to nucleases present within the sample. In certain embodiments, the maceration process can be accelerated, as disclosed herein, by the addition of a cationic surfactant to the reaction composition. Under appropriate conditions, in certain embodiments, high integrity nucleic acid can be efficiently obtained from biological samples in 60 minutes or less using the compositions and methods of the invention. Thus, in certain embodiments, the compositions and methods of the invention provide an unexpected advantage.

Some cationic surfactants, under appropriate conditions, form a complex with the released nucleic acid and precipitate. In certain embodiments, these cationic surfactant: nucleic acid complexes may be dissolved using a nonionic surfactant and an appropriate salt. In certain embodiments, these cationic surfactant:nucleic acid complexes may be dissolved using a zwitterionic or anionic surfactant, and an appropriate salt. Thus, in certain embodiments, the compositions further comprise a second surfactant and a salt.

In certain embodiments, the released nucleic acid is isolated. In certain embodiments, nucleic acids can be isolated effectively from aqueous solutions that contain biomolecules, such as lipids, proteins, and the like, using organic solvents. For example, in certain embodiments, organic solvents such as phenol or combinations of phenol and chloroform can be used to extract the nucleic acids from such solutions. In certain embodiments, the extracted nucleic acids can be isolated by precipitating the nucleic acid using, for example, alcohols such as ethanol, propanol, or butanol. In certain embodiments, the released nucleic acid is not isolated from the reaction composition.

In certain embodiments, nucleic acids may also be isolated from the reaction composition using certain polymers or divalent cations for precipitating the nucleic acids. Exemplary polymers for precipitating nucleic acids include, but are not limited to, polyethylene glycol, polyethyleneimine, DEAE dextran, polylysine, polyarginine, polyhistidine, and other weakly basic polymers. Descriptions of such polymers may be found, among other places, in U.S. Pat. Nos. 5,582,988; 5,733,762; 5,622,822; and 5,599,667. In certain embodiments, certain divalent cations may also cause nucleic acid molecules to selectively precipitate from solution. Examples of such divalent cations include, but are not limited to, zinc chloride, magnesium chloride and magnesium sulfate.

Additionally, in certain embodiments, nucleic acids may be isolated using solid phase supports that selectively bind nucleic acids. For example, but not limited to, nucleic acids from a sample can be adsorbed to a solid phase in the presence of high concentrations of a chaotrope or salt. In certain embodiments, the solid phase may be washed to remove contaminating material, and the nucleic acid can be eluted from the solid phase using a solution with a low ionic strength. Suitable solid phases include, but are not limited to, silica particles, silicon dioxide, diatomaceous earth, glass, alkylsilica, aluminum silicate, or borosilicate.

Also, in certain embodiments, nucleic acids can be bound to an ion exchange resin in the presence of low ionic strength. In certain embodiments, following removal of the contaminating components by washing, the nucleic acid is eluted from the solid phase by increasing the ionic strength. Exemplary ion-exchange resins include, but are not limited to, diethylaminoethyl- and triethylaminoethyl-derivatized supports (Chromegabond SAX, LiChrosorb-AN, Nucleosil SB, Partisil SAX, RSL Anion, Vydac TP Anion, Zorbax SAX, Nucleosil NMe2, Aminex A-series, Chromex, and Hamilton HA Ionex SB, DEAE sepharose, or QAE sepharose, and the like). The skilled artisan will appreciate that other solid phase materials may also be used, in certain embodiments, for example, but not limited to, nitrocellulose, diazotized paper, hydroxyapatite, nylon, metal oxides, zirconia, alumina, and reverse-phase resins (such octyl or phenyl sepharose).

The compositions of the invention include at least one protease. In certain embodiments, proteases such as subtilisins, subtilases, and alkaline serine proteases are employed. Exemplary proteases include, but are not limited to, Proteinase R, Proteinase T, subtilisin DY, dispase, subtilisin Carlsberg, subtilopeptidase A, thermolysin, thermostable proteases (such as those from *Thermus* Rt41A and *Bacillus thermoproteolyticus rokko*), and alkaline serine proteases from *Streptomyces griseus* or *Bacillus licheniformis*. According to certain embodiments, the protease is Proteinase K.

Certain proteases, including Proteinase K, may be stabilized by the presence of calcium chloride. When calcium chloride is combined with certain anionic surfactants, such as SDS, a relatively insoluble precipitate may be formed. In certain instances, scientists may try to avoid such precipitation by not using calcium chloride when employing both protease and anionic surfactants. In certain embodiments of the invention in which no substantial amount of anionic surfactants are employed, calcium chloride may be included. Calcium ions, as well as other divalent cations, typically do not react with cationic surfactants to form an insoluble complex.

To obtain high integrity DNA, in certain embodiments, DNAse inhibitors may be added to the compositions of the invention. For example, many endogenous DNAses are inhibited by divalent cation chelators, such as EDTA (ethylenediaminetetraacetic acid), EGTA ([ethyleneglycol-bis (β-aminoethyl)-N,N,N',N',-tetraacetic acid]), DTPA (diethylenetriaminepentaacetic acid), and the like.

In certain embodiments, the at least one cationic surfactant comprises a quaternary amine, a tertiary amine, or both. In certain embodiments, the at least one cationic surfactant comprises cetyltrimethylammonium bromide (CTAB), cetyltrimethylammonium chloride (CTACl), hexadecyltrimethylammonium bromide (HDTAB), or hexadecyltrimethylammonium chloride (HDTACl), and the at least one protease comprises Proteinase K.

In certain embodiments, the at least one cationic surfactant comprises an alky amine oxide at a pH that makes the surfactant cationic. In certain embodiments, the at least one cationic surfactant comprises at least one of octylamine, oxide, decylamine oxide, dodecylamine oxide, tetradecylamine oxide, and hexadecylamine oxide.

In certain embodiments, the at least one cationic surfactant comprises an alkyl imidazoline derivative or an alkyl phosphonium derivative.

In certain embodiments, isolating the nucleic acid comprises extracting the nucleic acid with an organic agent, such as, but without limitation, phenol, chloroform, both phenol and chloroform, or a β-lactam derivative. In certain embodiments, the nucleic acid may be precipitated with an organic agent, for example, without limitation, an alcohol such as isopropanol, ethanol, or butanol. In certain embodiments, isolating the nucleic acid comprises a combination of extracting the nucleic acid with an organic agent and precipitating the extracted nucleic acid with an organic agent.

In certain embodiments, methods for isolating ribonucleic acid from a biological sample are provided comprising using a cationic surfactant, a protease, and a buffer. In certain embodiments, the cationic surfactant is CTAB (Sigma or Aldrich), CTACl (Sigma or Aldrich), HDTAB (Sigma #H-5882 or Fluka #52367), or HDTACl (Fluka #41199). When high integrity RNA is desired, the presence of endogenous RNAses sometimes limit the efficiency of some current procedures. In certain embodiments, two components of the instant compositions and methods, however, can counteract the activity of endogenous RNAses, enhancing the isolation of high integrity RNA. First, Proteinase K may inactivate RNAse. Second, cationic surfactants may form complexes with RNA, decreasing the susceptibility of the RNA to RNAse degradation. See, e.g., Dahl, C. E. and Macfarlane, D. E., Isolation Of RNA From Cells In Culture Using Catrimox-14™ Cationic Surfactant, BioTechniques Vol. 15, No. 6: 1102-1105 (1993); Macfarlane, D. E. and Dahle, C. E., Isolation RNA From Whole Blood-The Dawn Of RNA-Based Diagnosis? Nature, Vol. 362: 186-188 (1993); Macfarlane, D. E. and Dahle, C. E., Isolating RNA From Clinical Samples With Catrimox-14 and Lithium Chloride, Journal of Clinical Laboratory Analysis. 11: 132-139 (1997).

According to certain embodiments, endogenous RNAse activity is further diminished using the compositions and methods of the invention. For example, in certain embodiments, RNAses typically are less active at lower pH, e.g., between pH 5 and 7, and temperatures below 50° C. In certain embodiments, acridine orange may also decrease the nucleolytic activity of RNAse, presumably by interacting with the released RNA molecules making them less susceptible to degradation. In certain embodiments, RNAse inhibitors may also be added to limit or prevent RNAse activity. Exemplary RNAse inhibitors include, but are not limited to, aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvic acid, formamide, dimethylformamide, copper, zinc, and the like. In certain embodiments, the compositions and methods of the invention comprise at least one RNAse inhibitor.

According to certain embodiments, cationic surfactants in the compositions and used in the methods have the general chemical formula:

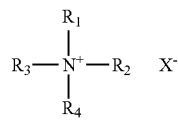

($N^+R_1R_2R_3R_4$:$X^-$), where the cation moieties $R_1$, $R_2$, $R_3$, and $R_4$ independently may be: —H, an alkyl group containing up to 20 carbon atoms, or an aryl group containing between 6 and 26 carbon atoms; wherein at least one of $R_1$, $R_2$, $R_3$, or $R_4$ contains an alkyl group of at least 6 carbons; and where $X^{31}$ is an anion. For example, the cationic surfactant may be an alkyltrimethyl ammonium salt, where $R_1$, $R_2$, and $R_3$ are methyl groups, and $R_4$ is an alkyl group comprising 6, 8, 10, 12, 14, 16, or 18 carbon atoms. The cationic subcomponent ($N^+R_1R_2R_3R_4$) of the alkyltrimethyl ammonium salt might be (without limitation) a cetyltrimethylammonium group, a hexadecyltrimethylammonium group, a tetradecyltrimethylammonium group, a dodecyltrimethylammonium group, a lauryl trimethylammonium group, or the like. The anionic subcomponent ($X^-$) of this exemplary alkyltrimethyl ammonium salt might be (without limitation) any of the following ions: bromide, chloride, iodide, hydroxide, nitrate, sulfate, phosphate, formate, acetate, propionate, oxalate, malonate, succinate, or citrate. In certain embodiments, the cationic surfactant is a benzyldimethyl-n-alkylammonium salt, comprising the same group of anions.

In certain embodiments, the compositions and methods of the invention may further comprise solubilizing agents. In certain embodiments, solubilizing agents are particularly useful when the biological sample is resistant to digestion, for example, when the sample comprises whole tissue. In certain embodiments, solubilizing agents help to disassemble the intercellular matrix, allowing the surfactant and protease to more effectively penetrate and disaggregate the sample. Exemplary solubilizing agents include, but are not limited to, 1-methyl-2-pyrolidinone, N-methyl pyrolidinone, pyrolidinone, dimethylsulfoxide, dimethylformamide, and the like.

In certain embodiments, the invention also provides kits designed for releasing and/or for isolating nucleic acid from biological samples. The kits comprise at least one cationic surfactant and at least one protease, and according to certain embodiments may include additional component(s). In certain embodiments, the kits preferably contain components in pre-measured unit amounts to minimize the measurements by end-users. In certain embodiments, the kits include instructions for performing one or more methods of the invention. In certain embodiments, the kit components are optimized to operate in conjunction with one another.

In certain embodiments, the at least one surfactant comprises CTAB, CTACl, HDTAB, HDTACl, or an equivalent. In certain embodiments, the at least one protease comprises Proteinase K. In certain embodiments, other reagents for isolating extracted nucleic acid may be included in such kits. In certain embodiments, the kits of the invention may further comprise reaction buffers, salts, ions, stabilizers, nuclease inhibitors, solubilizing agents, or combinations of these components.

According to certain embodiments, methods for obtaining nucleic acid from a biological sample and binding the nucleic acid to a solid phase is provided, which comprises: contacting the biological sample with a disrupting buffer, wherein the disrupting buffer comprises a protease and a cationic surfactant; and binding the nucleic acid to a solid phase.

According to certain embodiments, methods for obtaining nucleic acid from a biological sample and binding the nucleic acid to a solid phase is provided, which comprises, contacting the biological sample with a disrupting buffer, wherein the disrupting buffer comprises a protease and a cationic surfactant; substantially neutralizing the cationic surfactant; and binding the nucleic acid to a solid phase. According to certain embodiments, the cationic surfactant does not precipitate when the pH of the buffer is raised above pH 8.

According to certain embodiments of the methods, the cationic surfactant is selected from at least one of the group comprising cetyltrimethylammonium bromide (CTAB), cetyltrimethylammonium chloride (CTACl), tetradecyltrimethylammonium bromide (TTAB), tetradecyltrimethylammonium chloride (TTACl), dodecyltrimethylammonium bromide (DTAB), dodecyltrimethylammonium chloride (DTACl), dodecylethyldimethylammonium bromide (DEDTAB), decyltrimethylammonium bromide (D10TAB), and dodecyltriphenylphosphonium bromide (DTPB).

According to certain embodiments, the substantially neutralizing of the cationic surfactant is accomplished by substantially removing the cationic surfactant. According to certain embodiments, such methods may include, but are not limited to, one or more of precipitation, phase extraction, and dialysis. For an exemplary summary of such methods, see, e.g., K. Ohlendieck, Removal of Detergent From Protein Fractions, Methods Mol. Biol. 59:305-312, (1996). In certain embodiments, anionic detergents can be removed by precipitation with cations that form an insoluble complex, such as potassium and guanidinium. See, e.g., Shively, J. E., *Methods of Protein Microcharacterization*, pp. 41-87 (1986). Commercially available dialysis products for detergent removal include, but are not limited to, Harvard/Amika Dialysis products, Biodialyser (Western Analytical Products, Inc.), and Amicon®, Microcon®, and Centricon® Centrifugal devices (Millipore Corporation). Chromatographic approaches for detergent removal include, but are not limited to, gel filtration; hydrophobic chromatography; reverse phase HPLC; and ion exchange chromatography. For an exemplary summary of such techniques and principles, see, e.g., Bhairi, S. M., *Detergents: A Guide To The Properties And Uses Of Detergents In Biological Systems*, (1997). Examples of commercially available resins and other products for detergent removal include, but are not limited to, CALBIOSORB™ Adsorbent (Calbiochem-Novabiochem Corporation); Detergent-OUT™ SDS-300 (Genotech); Detergent-OUT™ DTG-100; OrgoSol-Detergent-OUT™ (Genotech); Bio-Beads SM2TM (BioRad); Vivapure Ion Exchange (Vivascience); and ZipTim$_{HPL}$ (Millipore Corporation).

According to certain embodiments of the methods, the substantially neutralizing of the cationic surfactant comprises adding a second surfactant that substantially neutralizes the cationic surfactant. According to certain embodiments, the second surfactant is a nonionic surfactant. According to certain embodiments, the nonionic surfactant is selected from at least one of the group comprising t-octylphenoxypolyethoxyethanol (Triton X-100), polyoxyethylenesorbitan monolaurate (Tween 20), polyoxyethylenesorbitan monolaurate (Tween 21), polyoxyethylenesorbitan monopalmitate (Tween 40), polyoxyethylenesorbitan monostearate (Tween 60), polyoxyethylenesorbitan monooleate (Tween 80), polyoxyethylenesorbitan monotrioleate (Tween 85), (octylphenoxy) polyethoxyethanol (IG-EPAL CA-630/NP-40), triethyleneglycol monolauryl ether (Brij 30), and sorbitan monolaurate (Span 20). According to certain embodiments, the nonionic surfactant is Tween 20. According to certain embodiments, the Tween 20 is present in a concentration of at least 4% w/w. According to certain embodiments, the Tween 20 is present in a concentration of 20% w/w.

According to certain embodiments of the methods, the method of obtaining nucleic acid from a biological sample and binding the nucleic acid to a solid phase further comprises adding a salt. According to certain embodiments, the salt is selected from at least one of the group comprising NaCl, NaBr, NaI, NaSCN, LiCl, LiBr, LiI, GuHCl, and GuSCN. According to certain embodiments of the methods, the salt is CaCl$_2$ and is present in a concentration of at least 20 mM.

According to certain embodiments of the methods, the protease is selected from at least one of the group comprising subtilisins, subtilases, and alkaline serine proteases. According to certain embodiments, the protease is selected from at least one of the group comprising proteinase K, proteinase, R, proteinase T, subtilisin. DY, an alkaline serine protease from *Streptomyces griseus*, an alkaline serine protease from *Bacillus lichenformis*, dispase, subtilisin Calsberg, subtilopeptidase A, and thermolysin.

According to certain embodiments, the protease is a thermostable protease. According to certain embodiments, the thermostable protease is isolated from an organism selected from at least one of the group comprising *Thermus* Rt41A and *Bacillus thermoproteolyticus rokko*.

According to certain embodiments of the methods, the lysing buffer further comprises a ribonuclease inhibitor. According to certain embodiments, the ribonuclease inhibitor is selected from at least one of the group comprising vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)] poly(adenyhlic acid), zinc sulfate, bromopyruvate, formamide, copper, and zinc. According to certain embodiments, the ribonuclease inhibitor is aurintricarboxylic acid. According to certain embodiments, the aurintricarboxylic acid is present in a concentration of 10 µM.

According to certain embodiments, the method of obtaining nucleic acid from a biological sample and binding the nucleic acid to a solid phase further comprises adding a deoxyribonuclease inhibitor. According to certain embodiments, the deoxyribonuclease inhibitor comprises a divalent cation chelator. According to certain embodiments, the divalent cation chelator is selected from at least one of the group comprising EDTA, EGTA, and DPTA.

According to certain embodiments, a kit is provided, comprising: a protease; a cationic surfactant; a salt; and a second surfactant, wherein the second surfactant substantially neutralizes the cationic surfactant.

According to certain embodiments of the kits, the cationic surfactant does not precipitate when the pH of the buffer is raised above pH 8.

According to certain embodiments of the kits, the cationic surfactant is selected from at least one of the group comprising cetyltrimethylammonium bromide (CTAB), cetyltrimethylammonium chloride (CTACl), tetradecyltrimethylammonium bromide (TTAB), tetradecyltrimethylammonium chloride (TTACl), dodecyltrimethylammonium bromide (DTAB), dodecyltrimethylammonium chloride (DTACl), dodecylethyldimethylammonium bromide (DEDTAB), decyltrimethylammonium bromide (D$_{10}$TAB), and dodecyltriphenylphosphonium bromide (DTPB).

According to certain embodiments of the kits, the protease is selected from at least one of the group comprising subtilisins, subtilases, and alkaline serine proteases. In certain embodiments, the protease is selected from at least one of the group comprising proteinase K, proteinase, R, proteinase T, subtilisin DY, an alkaline serine protease from *Streptomyces griseus*, an alkaline serine protease from *Bacillus lichenformis*, dispase, subtilisin Calsberg, subtilopeptidase A, and thermolysin.

According to certain embodiments of the kits, the protease is a thermostable protease. In certain embodiments, the thermostable protease is isolated from an organism selected from at least one of the group comprising *Thermus* Rt41A and *Bacillus thermoproteolyticus rokko*.

According to certain embodiments, the kit further comprises a ribonuclease inhibitor. In certain embodiments, the ribonuclease inhibitor is selected from at least one of the group comprising vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvate, formamide, copper, and zinc. In certain embodiments, the ribonuclease inhibitor is aurintricarboxylic acid. In certain embodiments, wherein the aurintricarboxylic acid is present in a concentration of 10 µM.

According to certain embodiments, the kit further comprises a deoxyribonuclease inhibitor. In certain embodiments, the deoxyribonuclease inhibitor comprises a divalent cation chelator. In certain embodiments, the divalent cation chelator is selected from at least one of the group comprising EDTA, EGTA, and DPTA.

According to certain embodiments, the kit further comprises a salt. In certain embodiments, the salt is selected from the group comprising NaBr, NaI, NaSCN, LiCl, LiBr, LiI, GuHCl, and GuSCN. In certain embodiments, the salt is CaCl$_2$. In certain embodiments, the CaCl$_2$ is present in a concentration of at least 20 mM.

According to certain embodiments, the second surfactant of the kits is a nonionic surfactant. In certain embodiments, the nonionic surfactant is selected from the group comprising t-octylphenoxypolyethoxyethanol (Triton X-100), polyoxyethylenesorbitan monolaurate (Tween 20), polyoxyethylenesorbitan monolaurate (Tween 21), polyoxyethylenesorbitan monopalmitate (Tween 40), polyoxyethylenesorbitan monostearate. (Tween 60), polyoxyethylenesorbitan monooleate (Tween 80), polyoxyethylenesorbitan monotrioleate (Tween 85), (octylphenoxy) polyethoxyethanol (IGEPAL CA-630/NP40), triethyleneglycol monolauryl ether (Brij 30), and sorbitan monolaurate (Span 20). In certain embodiments, the non-ionic surfactant is Tween 20. In certain embodiments, the Tween 20 is present in a concentration of at least 4% w/w. In certain embodiments, the Tween 20 is present in a concentration of 20% w/w.

According to certain embodiments, a kit for the isolation of nucleic acid from a biological sample is provided, comprising: a protease; a cationic surfactant; a non-ionic surfactant, wherein the non-ionic surfactant permits the binding of nucleic acid to a solid phase in the presence of the protease and cationic surfactant; and a buffer with a high salt concentration.

During the process of combining the process of releasing nucleic acid from samples using cationic surfactants with the process of binding the nucleic acid to a solid phase into a single nucleic acid isolation process, it was found that many of the cationic surfactants used to accomplish proteolysis were insoluble in the presence of the high salt concentrations that were used for binding nucleic acids onto solid phases. In addition, some cationic surfactants that were soluble in high salt inhibited the binding of nucleic acids to solid phases. This decreases nucleic acid binding to solid phases. In certain embodiments, one uses high salt concentrations for binding nucleic acids to a solid phase.

EXAMPLES

The following examples illustrate certain embodiments of the invention, and do not limit the scope of the invention in any way.

Example 1

An assay was developed to measure the activity of Proteinase K with BoDipy-labeled Casein Conjugate (Enz Check Protease Assay Kit, Product number E6638; Molecular Probes, Eugene, Oreg.). The concentration of fluorescent BoDipy moieties in this derivatized conjugate is sufficiently high so that when the protein is intact, the fluorescence of individual moieties is quenched. Upon digestion of the derivatized casein by a protease, however, peptides containing a lower number of BoDipy dye molecules are released, resulting in an increase in fluorescence. To determine an initial dynamic range for an assay, BoDipy-labeled Casein was digested for one hour with a decreasing concentration of Proteinase K as follows.

Proteinase K (Product number 2546, Ambion) was added over a range of final concentrations (40 fg/ml to 40 µg/ml) to 500 µL of buffer (10 mM Tris, pH 8, 20 mM CaCl$_2$) containing 10 µg/ml BoDipy-labeled Casein Conjugate. Following a one hour incubation at 60° C. with mixing, 100 µL aliquots were transferred to a 96-well optical plate (MicroAmp® Optical 96-Well Reaction Plate, Applied Biosystems, Foster City, Calif.) and the fluorescence was measured in an ABI Prism 7700 spectrophotometer (Applied Biosystems). The background fluorescence was determined by incubating the substrate in buffer without Proteinase K.

As shown in FIG. 1, the amount of fluorescence increased as the Proteinase K concentration increased. The signal appeared to plateau at around 30,000 fluorescence units and released fluorescence was detected from reaction compositions containing as little as 50 ng/ml Proteinase K.

Example 2

Initially, a series of reaction compositions were analyzed for their ability to disaggregate a biological sample, e.g., slices of liver. These reaction compositions comprised 100 mM Tris, pH 8.0, 20 mM dithiothreitol (DTT), and optionally, 1 mg/ml Proteinase K, surfactants (e.g., cationic, nonionic and anionic detergents), chaotropes, or the additive 1-methyl-2-pyrollidinone (Sigma). Each reaction compositions was placed in a tube with a slice of liver and then incubated at 65° C. The tubes were observed periodically to determine which reaction compositions were able to efficiently macerate the sample.

As shown in Table 1, Proteinase K alone was able to effectively digest the liver tissue, but only after extended incubation at 65° C. Of all of the reaction compositions examined, those containing the cationic surfactant CTAB most effectively macerated the sample during a one hour incubation period. Additionally, CTAB appeared to enhance the proteolytic activity of Proteinase K.

TABLE 1

| | 65° C. | | | | | |
|---|---|---|---|---|---|---|
| | No Proteinase K | | | 1 mg/ml Proteinase K | | |
| | 2-5 hr | 16-24 hr | 72 hr | 1 hr | 2-5 hr | 16-24 hr |
| Cationic Surfactants | | | | | | |
| Cetyltrimethylammonium bromide (1%) | | | | | 100% | 100% |
| Cetyltrimethylammonium bromide (0.1%) | | | | | 100% | 100% |
| Nonionic Surfactants | | | | | | |
| Tween 80 (0.1%) | | | | | 0% | 0% |
| Tween 80 (1%) | | | | | 0% | 0% |
| Tween 80 (0.1%) | | | | | 0% | |
| Triton X-100 (0.1%) | | | | | 0% | 0% |
| Triton X-100 (2%) | 0% | 0% | | | | |

TABLE 1-continued

| | 65° C. | | | | | |
|---|---|---|---|---|---|---|
| | No Proteinase K | | | 1 mg/ml Proteinase K | | |
| | 2-5 hr | 16-24 hr | 72 hr | 1 hr | 2-5 hr | 16-24 hr |
| Triton X-100 (1%) | | | | | 30% | 100% |
| Anionic Surfactants | | | | | | |
| Chenodeoxycholic Acid (0.1%) | | | | | 0% | 0% |
| Chenodeoxycholic Acid (1%) | | | | | 0% | 0% |
| Chenodeoxycholic Acid (2%) | | 0% | | | | |
| Cholic Acid (2%) | | 0% | | | | |
| Glycocholic Acid (0.1%) | | | | | 0% | 0% |
| Glycocholic Acid (1%) | | | | | 0% | 0% |
| Taurochenodeoxycholic Acid (0.1%) | | | | | 0% | 0% |
| Taurochenodeoxycholic Acid (1%) | | | | | 0% | 0% |
| Taurocholic Acid (0.1%) | | | | | 0% | 0% |
| Taurocholic Acid (1%) | | | | | 0% | 0% |
| Taurocholic Acid (2%) | | 0% | | | | |
| Taurodeoxycholic Acid (0.1%) | | | | | 0% | 0% |
| Taurodeoxycholic Acid (1%) | | | | | 0% | 0% |
| Octyl sulfonate (2%) | | | 0% | | | |
| Hexane sulfonic acid (2%) | | | 0% | | | |
| Octanonic Acid (2%) | | | 0% | | | |
| SDS (1%) | 0% | | | | 50% | |
| Lauryl Sarcosine (2%) | | | 0% | | | |
| Saponin (0.1%) | | | | | 0% | 0% |
| Saponin (1%) | | | | | 0% | 0% |
| Saponin, (2%) | 0% | 50% | | | | |
| NiaProof Type 8 (0.1%) | | | | | 0% | 0% |
| NiaProof Type 8 (1%) | | | | | 0% | 0% |
| Niaproof Type 8 (2%) | 0% | | | | | |
| Chaotropes | | | | | | |
| Guanidinium chloride (2 M) | 0% | | | | 0% | |
| Guanidinium thiocyanate (1 M) | 0% | | | | 25% | |
| Tetramethylammonium chloride (0.1 M) | | 0% | | 0% | | 0% |
| Tetramethylammonium chloride (1 M) | | 0% | | 0% | | 0% |
| Other additives | | | | | | |
| 1-methyl 2-pyrrolidinone (2%) | | 0% | | | | |
| No Additives | | | | | | |
| None | | | | | 0% | 75% |

Example 3

To test the effect of cationic surfactants on the activity of Proteinase K, a series of reaction compositions were prepared as follows. Reaction compositions comprised: Casein BoDipy conjugate (1 μg, 10 ng/μL), 10 mM Tris, pH 8, 20 mM $CaCl_2$, 1% surfactant (shown in Table 2 below) and a dilution series of Proteinase K at concentrations of 20 μg/ml, 5 μg/ml, 1.25 μg/ml, 0.31 μg/ml, 0.078 μg/ml, 0.02 μg/ml and 0.005 μg/ml. The anionic surfactant sodium dodecyl sulfate (SDS), known to activate Proteinase K activity under the conditions tested, was included as a positive control. Reaction tubes were incubated at 60° C. in a 96-well optical plate (MicroAmp® Optical 96-Well Reaction Plate, Applied Biosystems) and the amount of released fluorescence was measured at the indicated time points using an ABI Prism 7700.

TABLE 2

Surfactants

| Surfactant | Source |
|---|---|
| Olealkonium chloride | (CAS No.: 37139-99-4, McIntyre Group LTD). |
| Mackernium SDC-85 (Stearalkonium chloride) | (CAS No. 122-19-0, McIntyre Group LTD). |
| Mackernium NLE | (Quaternium-84) (McIntyre Group LTD) |
| Mackernium 006 | (Polyquaternium-6) (Cas No. 26062-79-3) (McIntyre Group, LTD) |
| Mackernium 007 | (Polyquaternium-7) (Cas No. 26590-05-6) (McIntyre Group, LTD) |
| Mackernium WLE | (Wheat Germamidopropyl Epoxy Q) (McIntyre Group, LTD) |
| Benzalkonium Chloride | (Sigma, Product Number B-6295) |
| Benzyldimethylhexadecylammonium Chloride | (Sigma, Product Number B-4136) |
| Benzyldimethyltetradecylammonium Chloride | (Sigma, Product Number B-5651) |
| Benzyldimethyldodecylammonium bromide | (Sigma, Product Number B-5776) |
| Tetradecyltrimethylammonium Bromide | (Sigma, Product Number T-4762) |

TABLE 2-continued

Surfactants

| Surfactant | Source |
|---|---|
| Hexadecyltrimethylammonium Bromide | (Sigma, Product Number H-5882) |
| Dodecyltrimethylammonium Bromide | (Sigma, Product Number D-8638) |
| Mixed Alkyltrimethylammonium Bromide | (Sigma, Product Number M-7635) |
| Cetyltrimethylammonium bromide (CTAB) | (Calbiochem, Product number B22633) |
| Sodium Dodecyl Sulfate (SDS) | (Sigma, Product Number L6026) |

Figure 2A:
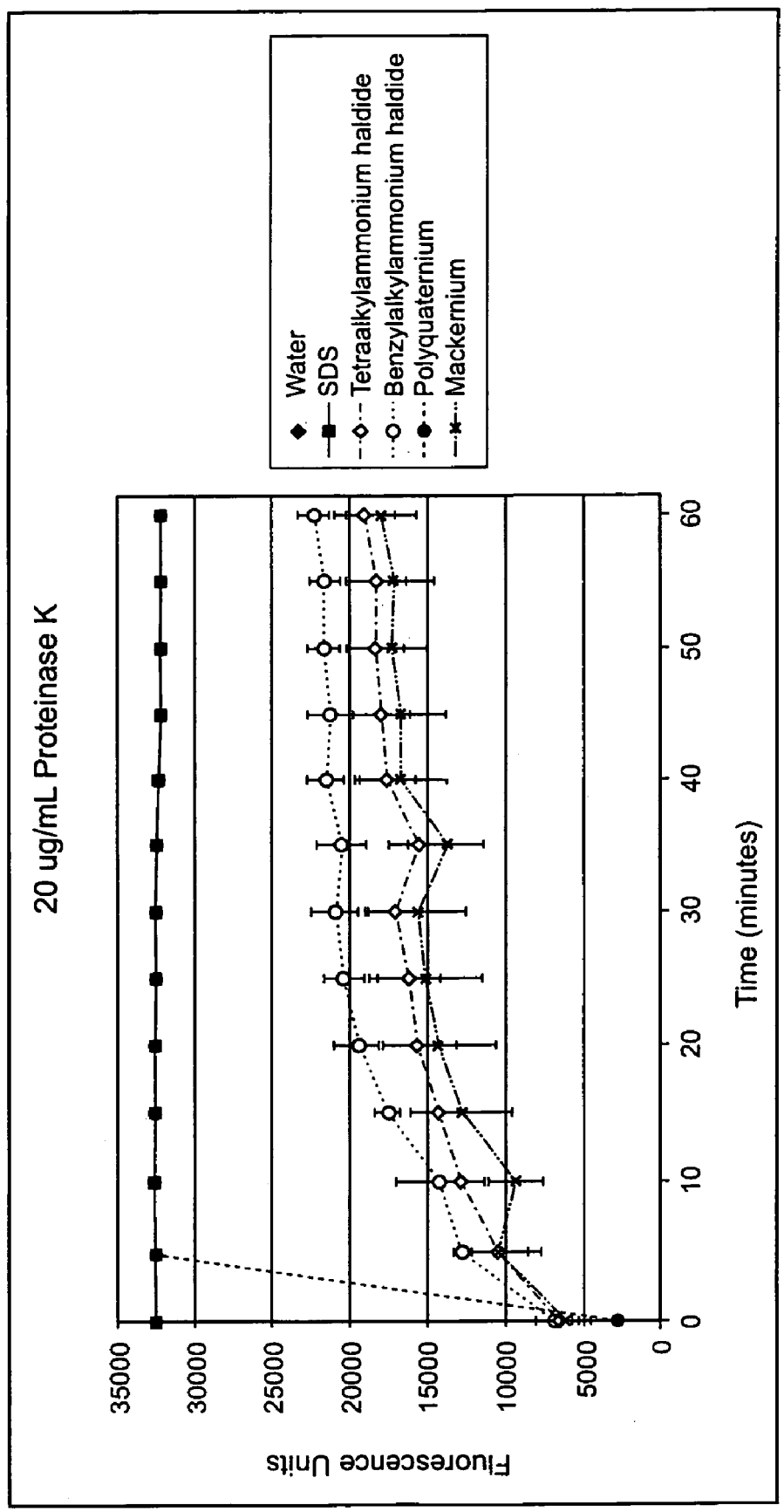
FIG. 2A depicts a reaction composition comprising 20 μg/ml Proteinase K.
Figure 2B:
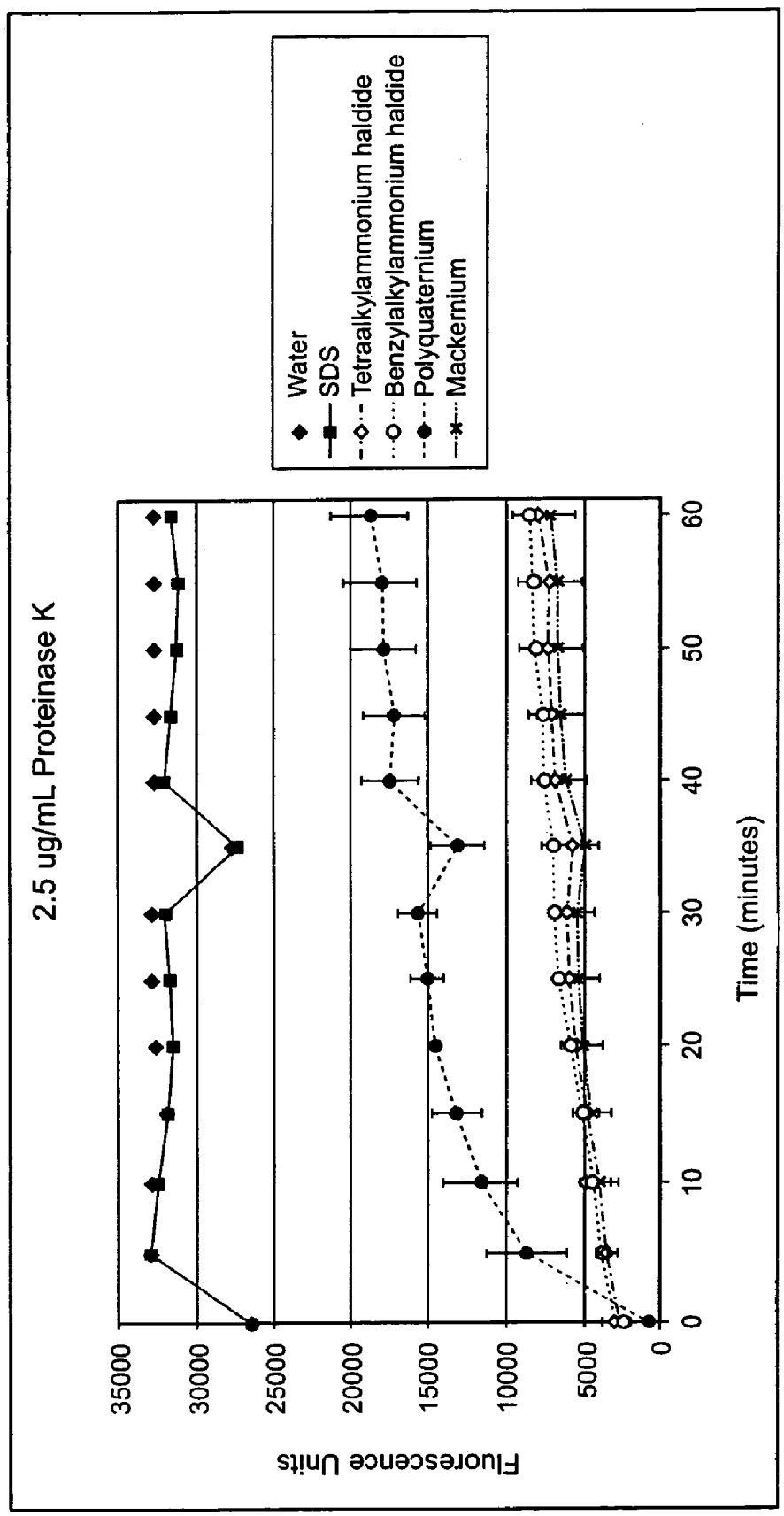
FIG. 2B depicts a reaction composition comprising 2.5 μg/ml Proteinase K.
Figure 2C:
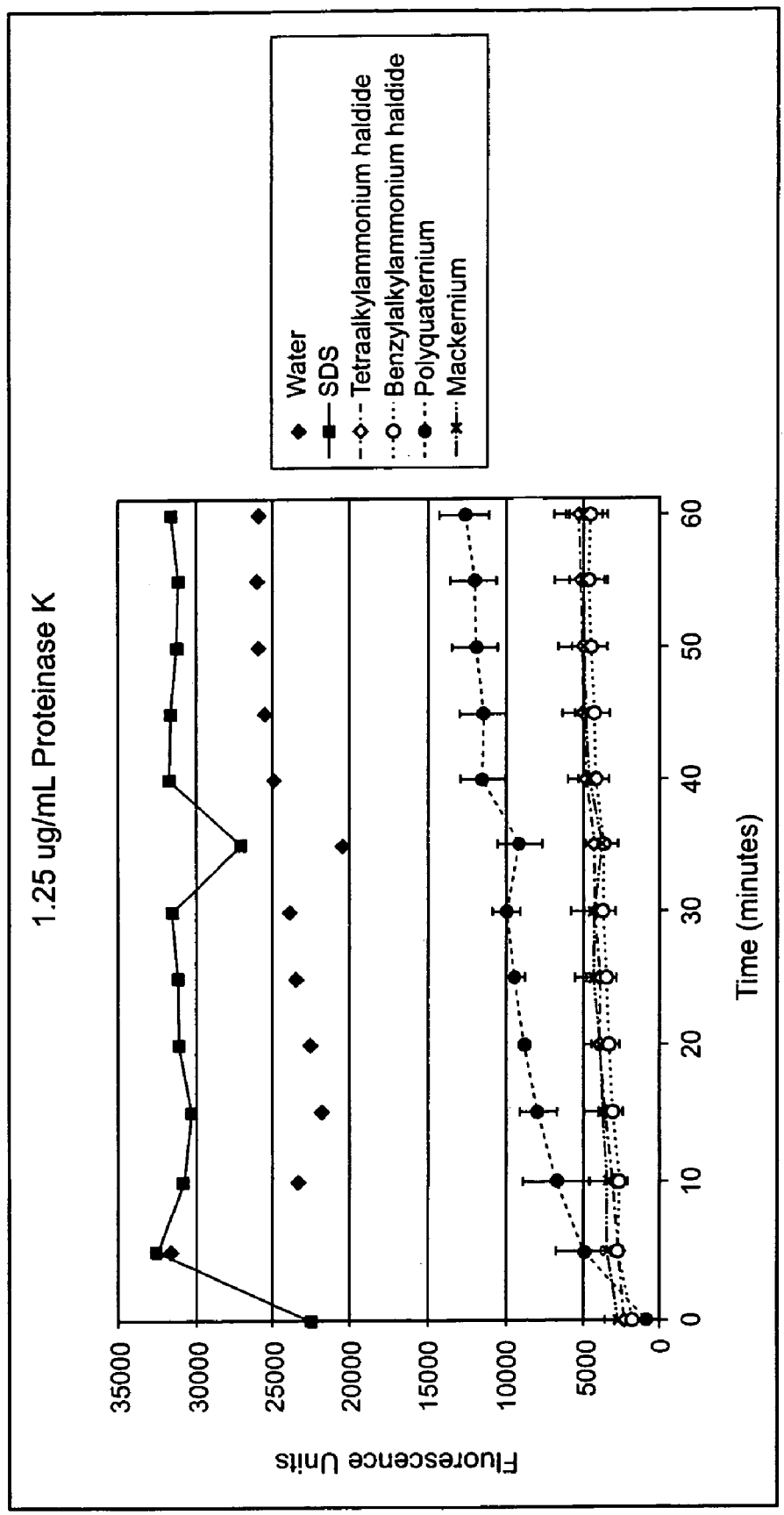
FIG. 2C depicts a reaction composition comprising 1.25 μg/ml Proteinase K. The tetraalkylammonium halide symbol (open diamond) represents the average data for the cationic surfactants dodecyltrimethylammonium bromide, tetradecyltrimethylammonium bromide, hexadecyltrimethylammonium bromide, cetyltrimethylammonium bromide, and mixed alkyltrimethylammonium bromide. The symbol for benzylalkylammonium halide (open circle) represents the average data for the cationic surfactants benzalkonium chloride, benzyldimethyldodecylammonium bromide, benzyldimethylhexadecylammonium bromide and benzyldimethyltetradecyl ammonium chloride. The symbol for Mackernium (X) represents the average data for the cationic surfactants Mackernium SDC-85, Mackernium KP, Mackernium WLE and Mackernium NLE. The polyquaternium symbol (closed circle) represents the average data for the cationic polymers Mackernium 006 and Mackernium 007. The results obtained using water (closed diamond) and using the anionic surfactant SDS (closed square) are also shown. The error bars represent the standard deviation for the each data set.

As shown in FIGS. 2A-C: (i) Proteinase K without surfactant has high proteolytic activity, even at ambient temperature (see 0 minutes incubation in water); (ii) SDS enhances the activity of Proteinase K on the casein substrate; (iii) the two cationic polymers (Mackernium 006 and 007) have a slightly inhibitory activity on Proteinase K activity; and (iv) all of the cationic surfactants tested appear to inhibit Proteinase K activity (compare the tetraalkylammonium halide, benzylalkylammonium halide, or polyquaterniums curve with that for water alone, i.e., no surfactant).

Example 4

Since it is typically difficult to extract nucleic acid from whole tissue, it can be used effectively to illustrate the efficiency of the compositions and methods of the invention. Thus, the remainder of the examples were performed using liver tissue as an exemplary whole tissue. The skilled artisan will understand, however, that the disclosed compositions and methods may also be effectively employed using a broad range of biological samples and that the invention is not to be limited to use with any sample type.

In the initial approach for evaluating the efficacy of nucleic acid release by various test treatments, liver samples were digested for a specified period of time in reaction compositions comprising surfactant and Proteinase K. The protocol included removing undigested material using centrifugation. Preliminary results using purified nucleic acid and cationic surfactants demonstrated that the cationic surfactant was forming a precipitate with the nucleic acid (data not shown). Further, this complex was being removed with the undigested tissue during centrifugation. Thus, one way to quantify the amount of nucleic acid being released from the sample, included freeing the nucleic acid from the surfactant: nucleic acid complex. Conditions were evaluated for freeing the nucleic acid from the cationic surfactant complexes as follows.

Calf thymus DNA (Sigma; 700 μg/ml lightly sheared using an 18 gauge hypodermic needle) was mixed with 1% CTAB in 100 mM Tris, pH 8 to form a reaction composition. Initially, a noticeable precipitate was observed. A variety of additives, shown in Table 3, were tested with aliquots of this reaction composition to identify compositions that would solubilize the cationic surfactant: nucleic acid precipitate.

TABLE 3

| Sample | Additive (final concentration) | Result |
|---|---|---|
| 1 | 91 mM NaCl | Nucleic acid precipitated |
| 2 | 333 mM NaCl | Nucleic acid precipitated |
| 3 | 117 mM Tetramethylammonium chloride | Nucleic acid precipitated |
| 4 | 758 mM Tetramethylammonium chloride | Nucleic acid precipitated |
| 5 | 95 mM Tetrabutylammonium chloride | Nucleic acid precipitated |
| 6 | 400 mM Tetrabutylammonium chloride | Nucleic acid precipitated |
| 7 | 312.5 mM NaCl, 6.25% 1-Methyl-2-Pyrrolidinone | Nucleic acid precipitated |
| 8 | 692 mM Tetramethylammonium chloride, 7.5% 1-Methyl-2-pyrrolidinone | Nucleic acid precipitated |
| 9 | 370 mM Tetrabutylammonium chloride, 7.4% 1-Methyl-2-pyrrolidinone | Nucleic acid precipitated |
| 10 | 9.1% 1-Methyl-2-pyrrolidinone (Sigma #M-6762) | Nucleic acid precipitated |
| 11 | 294 mM NaCl, 5.9% 1-Methyl-2-Pyrrolidinone, 5.9% Tween 20 | Nucleic acid pellet fairly dissolved |
| 12 | 643 mM Tetramethylammonium chloride, 7.0% 1-Methyl-2-pyrrolidinone, 7.0% Tween 20 | Nucleic acid pellet fairly dissolved |
| 13 | 345 mM Tetrabutylammonium chloride, 6.9% 1-Methyl-2-Pyrrolidinone, 6.9% Tween 20 | Nucleic acid pellet began to solubilize |
| 14 | 8.3% 1-Methyl-2-Pyrrolidinone, 8.3% Tween 20 | Nucleic acid pellet began to solubilize |
| 15 | 10% Tween 20 (Sigma #P-9416) | Nucleic acid precipitated |
| 16 | 312.5 mM NaCl, 6.25% Tween 20 | Nucleic acid pellet completely solubilized |
| 17 | 2.0% Tween 20 | Nucleic acid precipitated |
| 18 | 160 mM NaCl, 1.6% Tween 20 | Nucleic acid precipitated |
| 19 | 9.1% 1-hexanesulfonic acid | Nucleic acid pellet partially solubilized |
| 20 | 17% 1-hexanesulfonic acid | Nucleic acid pellet partially solubilized |
| 21 | 200 mM NaCl, 16% Hexane sulfonic acid | Nucleic acid pellet partially solubilized |
| 22 | 9.1% Decanesulfonic acid | Nucleic acid pellet partially solubilized |
| 23 | 217 mM NaCl, 8.7% Decanesulfonic acid | Nucleic acid pellet partially solubilized |
| 24 | 50% Nucleic Acid Purification Lysis Solution | Nucleic acid pellet completely solubilized |
| 25 | 33% Nucleic Acid Purification Lysis Solution | Nucleic acid pellet completely solubilized |
| 26 | 23% Nucleic Acid Purification Lysis Solution | Nucleic acid pellet partially solubilized |
| 27 | 297 mM NaOAc | Nucleic Acid precipitated |
| 28 | 292 mM NaOAc, 1.8% Tween 20 | Nucleic Acid precipitated |
| 29 | 313 mM NaOAc, 2.6% Tween 20 | Nucleic Acid precipitated |
| 30 | 535 mM NaCl, 1.75% Tween 20 | Nucleic acid pellet completely solubilized |

As shown in Table 3, four of the reaction compositions resulted in complete solubilization of the precipitate. Nucleic Acid Purification Lysis Solution (#4305895, Applied Biosystems), used at final concentrations of 33% or 50%, completely solubilized the precipitate (see samples 24-25). Additionally, some combinations of the salt NaCl and the nonionic detergent Tween 20 completely solubilized the precipitate (see samples 16 and 30). However, neither NaCl nor Tween 20, used alone, solubilized the precipitate (see samples 1, 2, 15, and 17). The skilled artisan will understand that additional combinations of salts and non-ionic surfactants used at varying concentrations can be used to dissolve the cationic surfactant: nucleic acid precipitates.

Example 5

To evaluate the ability of various cationic surfactants to increase the digestion of tissue by Proteinase K, liver slices were digested using reaction compositions including one of the sixteen surfactants (shown in Table 4), both with and without Proteinase K. The reducing agent dithiothreitol (DTT) was included to evaluate the effect of reducing conditions on tissue digestion. Liver tissue (80-120 mg) was placed into each of thirty-four Eppendorf tubes (seventeen pairs of tubes) containing 1000 μL of 10 mM Tris, pH 8, 20 mM $CaCl_2$, and 20 mM dithiothreitol. One of the sixteen surfactants was added to one pair of tubes to yield a final concentration of 1% surfactant. The seventeenth pair of tubes served as non-surfactant controls. One milligram (mg) of Proteinase K was added to one tube of each of the seventeen pairs. The thirty-four tubes were then incubated at 60° C. with mixing (Eppendorf Thermomixer, Model 5436).

TABLE 4

| Surfactant | Chemical Formula |
| --- | --- |
| SDS | $CH_3(CH_2)_{11}OSO_3Na$ |
| Mackernium KP | $R_1R_2(CH_3)_2NCl$ $R_1$ = fatty group, $R_2$ = benzyl, methyl or epoxy group |
| Mackernium WLE | $R_1R_2(CH_3)_2NCl$ $R_1$ = fatty group, $R_2$ = benzyl, methyl or epoxy group |
| Benzalkonium chloride | $C_6H_5CH_2N(CH_3)_2RCl$ R = $C_8H_{17}$ to $C_{18}H_{37}$ |
| Mackernium 006 | Polyquaternium |
| Mackernium 007 | Polyquaternium |
| Mackernium NLE | $R_1R_2(CH_3)_2NCl$ $R_1$ = fatty group, $R_2$ = benzyl, methyl or epoxy group |
| Mackernium SDC-85 | $R_1R_2(CH_3)_2NCl$ $R_1$ = fatty group, $R_2$ = benzyl, methyl or epoxy group |
| Dodecyltrimethylammonium bromide | $CH_3(CH_2)_{11}N(CH_3)_3Br$ |
| Tetradecyltrimethylammonium bromide | $CH_3(CH_2)_{13}N(CH_3)_3Br$ |
| Hexadecyltrimethylammonium bromide | $CH_3(CH_2)_{15}N(CH_3)_3Br$ |
| CTAB | $CH_3(CH_2)_{15}N(CH_3)_3Br$ |
| Mixed alkyltrimethylammonium bromide | $CH_3(CH_2)_nN(CH_3)_3Br$ |
| Benzyldimethyldodecylammonium bromide | $C_6H_5CH_2N[(CH_2)_{11}CH_3](CH_3)_2Br$ |
| Benzyldimethyltetradecyl ammonium chloride | $C_6H_5CH_2N[(CH_2)_{13}CH_3](CH_3)_2Cl$ |
| Benzyldimethylhexadecylammonium bromide | $C_6H_5CH_2N[(CH_2)_{15}CH_3](CH_3)_2Br$ |

Each tube was visually evaluated after 15 minutes and 52 minutes of incubation. The results, shown in Table 5 (fifteen minutes incubation) and Table 6 (fifty-two minutes incubation), indicate that under the conditions tested, the combination of CTAB and Proteinase K caused total disaggregation of the tissue sample at either time point. Notably, CTAB alone caused no apparent sample disaggregation. The presence of DTT did not seem to significantly effect tissue disaggregation under these conditions.

TABLE 5

Observations after Fifteen Minutes Incubation.

| Surfactant | PK | Tissue Disaggregation | Color of Composition |
| --- | --- | --- | --- |
| Buffer alone (control) | Y | 0 | Light pink |
| SDS | Y | 3 | Slightly Cloudy |
| Mackernium KP | Y | 1 | Slightly Cloudy |
| Mackernium WLE | Y | 0 | Clear |
| Benzalkonium chloride | Y | 1 | Slightly Cloudy |
| Mackernium 006 | Y | 1 | Slightly Cloudy |
| Mackernium 007 | Y | 2 | Slightly Cloudy |
| Mackernium NLE | Y | 1 | Slightly Cloudy |
| Dodecyltrimethylammonium bromide | Y | 2 | Medium Cloudy |
| Tetradecyltrimethylammonium bromide | Y | 0 | Clear |
| Hexadecyltrimethylammonium bromide | Y | 0 | Clear |
| CTAB | Y | 4 | Dark brown |
| Mackernium SDC-85 | Y | 3 | Medium cloudy |
| Mixed alkyltrimethylammonium bromide | Y | 3 | Medium cloudy |
| Benzyldimethyldodecylammonium bromide | Y | 0 | Clear |
| Benzyldimethylhexadecylammonium bromide | Y | 0 | Clear |
| Benzyldimethyltetradecyl ammonium chloride | Y | 0 | Clear |
| Buffer alone (control) | N | 0 | Pink |
| SDS | N | 0 | Slightly cloudy |
| Mackernium KP | N | 0 | Clear |
| Mackernium WLE | N | 0 | Pink |
| Benzalkonium chloride | N | 0 | Clear |
| Mackernium 006 | N | 0 | Slightly pink |
| Mackernium 007 | N | 0 | Slightly pink |
| Mackernium NLE | N | 0 | Slightly brown |
| Dodecyltrimethylammonium bromide | N | 0 | Slightly pink |
| Tetradecyltrimethylammonium bromide | N | 0 | Slightly pink |
| Hexadecyltrimethylammonium bromide | N | 0 | Clear |
| CTAB | N | 0 | Slightly pink |
| Mackernium SDC-85 | N | 0 | Clear |
| Mixed alkyltrimethylammonium bromide | N | 0 | Clear |
| Benzyldimethyldodecylammonium bromide | N | 0 | Slightly cloudy |
| Benzyldimethylhexadecylammonium bromide | N | 0 | Clear |
| Benzyldimethyltetradecyl ammonium chloride | N | 0 | Clear |

PK=presence or absence of Proteinase K in the reaction composition; Y=Proteinase K was present; N=Proteinase K was not present in the reaction composition. Tissue disaggregation: 0=none; 1=No fragmentation, supernatant slightly cloudy; 2=Little fragmentation, supernatant slightly cloudy; 3 More significant tissue supernatant, supernatant very cloudy; 4=complete tissue aggregation with little insoluble material remaining.

TABLE 6

Observations after Fifty-Two Minutes Incubation.

| Surfactant | PK | Tissue Disaggregation | Color of Composition |
| --- | --- | --- | --- |
| Buffer alone (control) | Y | 0 | Slightly brown |
| SDS | Y | 3 | Moderately cloudy |

TABLE 6-continued

Observations after Fifty-Two Minutes Incubation.

| Surfactant | PK | Tissue Disaggre-gation | Color of Composition |
|---|---|---|---|
| Mackernium KP | Y | 4 | Very cloudy |
| Mackernium WLE | Y | 2 | Medium cloudy |
| Benzalkonium chloride | Y | 2 | Medium cloudy |
| Mackernium 006 | Y | 0 | Slightly brown |
| Mackernium 007 | Y | 2 | Some cloudiness |
| Mackernium NLE | Y | 1 | Slightly cloudy |
| Dodecyltrimethylammonium bromide | Y | 3 | Medium cloudy |
| Tetradecyltrimethylammonium bromide | Y | 1 | Slightly brown |
| Hexadecyltrimethylammonium bromide | Y | 1 | Medium brown |
| CTAB | Y | 4 | Very brown, milky |
| Mackernium SDC-85 | Y | 3 | Very cloudy |
| Mixed alkyltrimethylammonium bromide | Y | 3 | Very cloudy |
| Benzyldimethyldodecyl-ammonium bromide | Y | 1 | Slightly cloudy |
| Benzyldimethylhexadecyl-ammonium bromide | Y | 1 | Slightly cloudy |
| Benzyldimethyltetradecyl ammonium chloride | Y | 1 | Slightly cloudy |
| Water | N | 0 | Slightly brown |
| SDS | N | 0 | Slightly pink |
| Mackernium KP | N | 0 | Clear |
| Mackernium WLE | N | 0 | Slightly brown |
| Benzalkonium chloride | N | 0 | Clear |
| Mackernium 006 | N | 0 | Slightly brown |
| Mackernium 007 | N | 0 | Slightly cloudy |
| Mackernium NLE | N | 0 | Clear |
| Dodecyltrimethylammonium bromide | N | 0 | Clear |
| Tetradecyltrimethylammonium bromide | N | 0 | Clear |
| Hexadecyltrimethylammonium bromide | N | 0 | Slightly brown |
| CTAB | N | 0 | Slightly brown |
| Mackernium SDC-85 | N | 0 | Slightly pink |
| Mixed alkyltrimethylammonium bromide | N | 0 | Clear |
| Benzyldimethyldodecyl-ammonium bromide | N | 0 | Slightly brown |
| Benzyldimethylhexadecyl-ammonium bromide | N | 0 | Clear |
| Benzyldimethyltetradecyl ammonium chloride | N | 0 | Clear |

See legend to Table 5 for explanation of nomenclature.

Example 6

To examine the ability of cationic surfactants and Proteinase K to release high integrity nucleic acids from a biological sample, the released nucleic acid was isolated. Slices of liver tissue (90-200 mg per slice) were placed into each of twenty-two Eppendorf microfuge tubes. Four hundred μL of 50 mM Tris, pH 8, 20 mM $CaCl_2$, $_1$% surfactant, and 1 mg Proteinase K was added to each tube. The tubes were incubated at 60° C. for 22 minutes with mixing (Eppendorf Thermomixer, Model 5436).

Following the incubation, Nucleic Acid Purification Lysis Solution (#4305895, Applied Biosystems; final concentration 29%), sodium acetate (final concentration 214 mM) and glycogen (Mussel type VII, Sigma; final concentration 143 μg/ml) was added to each tube to dissolve the surfactant: nucleic acid complexes. The tubes were centrifuged in an Eppendorf microfuge (Model 5415C) at 14,000 RPM for 5 minutes to pellet remaining tissue fragments. The resulting supernatant was extracted using 700 μL of phenol (Sigma) saturated with 10 mM Tris HCl, pH 8.0, and 1 mM EDTA (saturated phenol). The pelleted material was also extracted with saturated phenol to obtain nucleic acid if any remained in the undigested sample. The extracted nucleic acid was precipitated using an equal volume (750 μL) of 2-propanol, and the tubes were incubated at −20° C. for 3 hours. The samples were centrifuged at ambient temperature in a microfuge at 14,000 RPM for 5 minutes, as before, to pellet the nucleic acid. The nucleic acid pellets were washed with 1 ml of 70% ethanol and the samples were centrifuged at ambient temperature in a microfuge at 14,000 RPM for 5 minutes. The washed nucleic acid pellets were resuspended in 100 μL 10 mM Tris, pH 8, 0.1 mM EDTA, and 1 unit/μL RNasin. The amount of released nucleic acid was quantitated using a UV/N is Spectrophotometer (Hewlett Packard, Model 8453). For quantitation purposes, it was assumed that the material that absorbed UV light at a wavelength of 260 nm was nucleic acid. Thus, an extinction coefficient of 1 $OD_{260}$=40 μg/ml was used.

Figure 3:
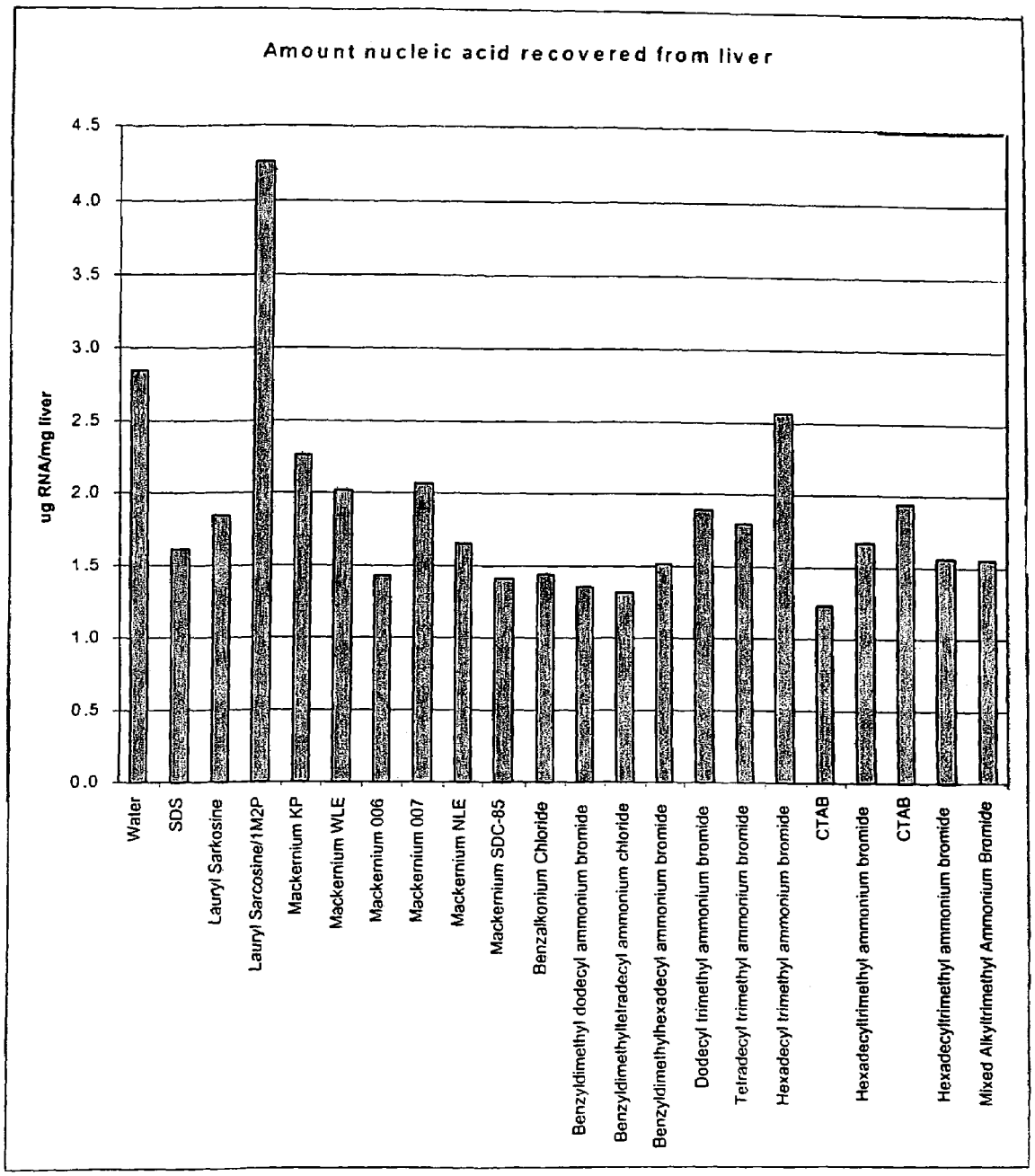
FIG. 3 illustrates the quantity of nucleic acid, measured in μg of nucleic acid/mg of sample, released using reaction compositions comprising Proteinase K and various surfactants.

FIG. 3 shows the amount of $A_{260}$-absorbing material recovered from the sample (μg nucleic acid/mg tissue processed). The results were normalized for the weight of each sample. Despite the reduced proteolytic activity of Proteinase K in the presence of the cationic surfactants, as demonstrated in the previous example, the amount of $A_{260}$-absorbing material was similar to the amount obtained with the anionic surfactants or without surfactant.

To evaluate the integrity of the released nucleic acid (i.e., its degree of degradation), and the amount of nucleic acid remaining in the tissue pellet, one tenth of each sample was analyzed by electrophoresis on a 1% agarose gel according to standard molecular biology procedures. Descriptions of standard molecular-biology procedures may be found, among other places, in Molecular Cloning: A Laboratory Manual, Sambrook et al., 1989, Cold Spring Harbor Press, Cold Spring Harbor, N.Y.; Current Protocols in Molecular Biology, Ausbel et al., 1993 and supplements through September 2000, John Wiley & Sons, New York, N.Y.; or Molecular Biology Techniques, W. Ream et al., Academic Press, San Diego, Calif., 1999.

Figure 4A:
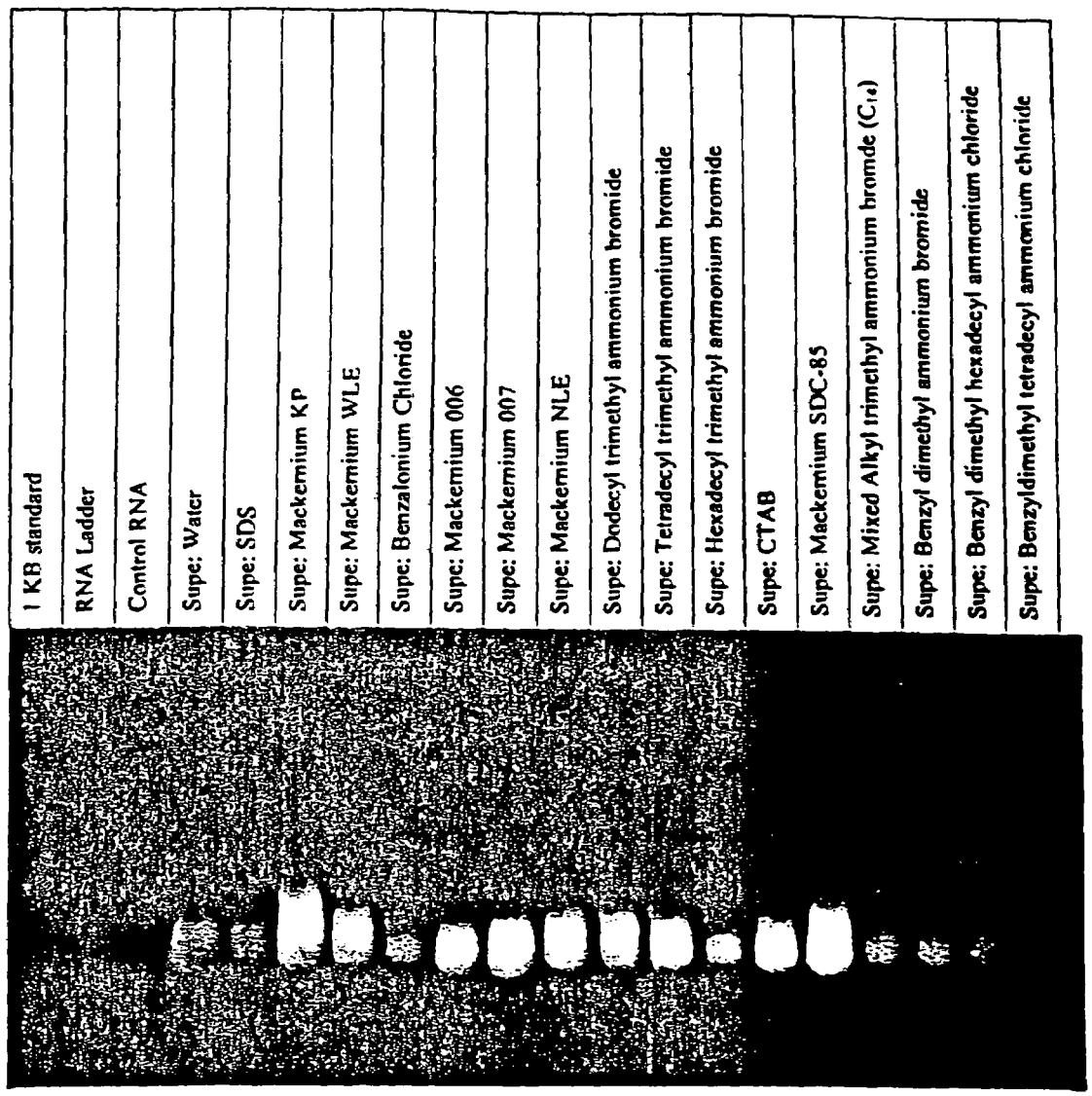
FIG. 4 depicts a stained agarose gel that provides a comparison between the amount of nucleic acid that is released (supe) with the nucleic acid remaining in the sample (pellet) following incubation with the reaction compositions comprising the indicated surfactants.
Figure 4B:
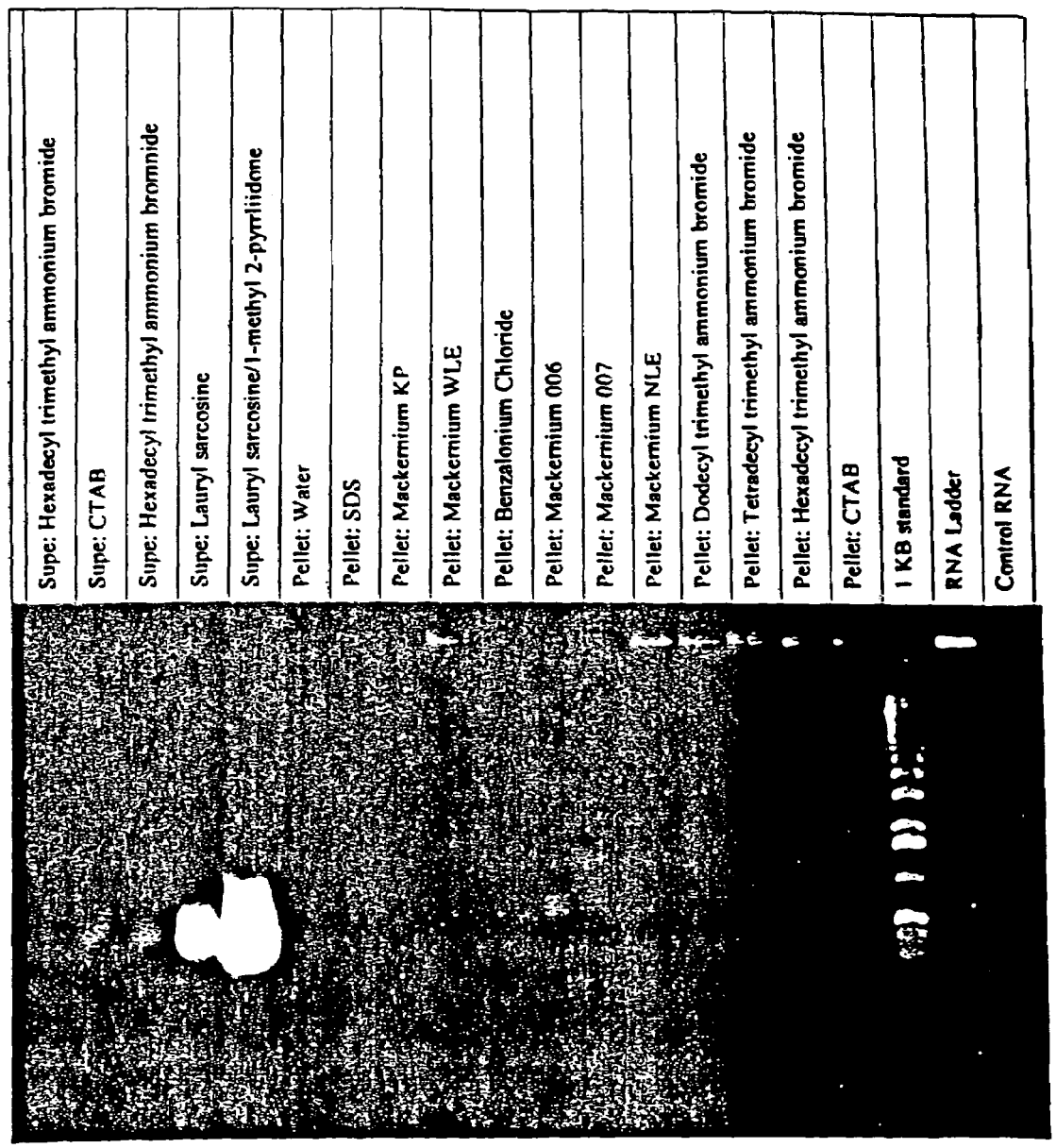

As shown in FIG. 4, most of the cationic surfactant: Proteinase K combinations released nucleic acid as evidenced by the little nucleic acid that remained in the pellet. The released nucleic acid was observed to have a high electrophoretic mobility, since it appeared near the bottom of the gel. Since intact, high integrity nucleic acid typically has a low, rather than a high, electrophoretic mobility, the recovered nucleic acid apparently was highly fragmented using these conditions. In other words, it apparently had a low integrity.

Example 7

The results from Example 6 indicate that there was significant nuclease activity present in the sample. To reduce the nucleolytic activity of endogenous RNAses, the pH of the reaction composition was lowered to approximately 6.0 and the incubation temperature was decreased to 45° C. Several additives, including phenylglyoxal (Aldrich #14243-3), 1-methyl-2-pyrolidinone, RNA Later (Ambion, #7020), and Streck Tissue Fixitive (Streck Laboratories, #265138) were also tested to evaluate their effect on endogenous RNAse activity in these reaction compositions. Phenylglyoxal is known to reduce ribonuclease activity (see Takahashi, The Structure And Funtion Of Ribonuclease $T_1$.

XI. Modification Of The Single Arginine Residue In Ribonuclease T1 By Phenylglyoxal And Glyoxal, J. Biochem (Japan) 68:659-664, 1970). The product literature for RNA Later claims that the reagent stabilizes RNA in tissue and Streck Tissue Fixative is believed to preserve the integrity of tissue.

Slices of liver tissue (100-200 mg/sample) were placed into nineteen Eppendorf tubes. Four hundred microliters of a reaction composition comprising 100 mM MES (Sigma #M-5287), pH 6, 20 mM $CaCl_2$, and 1 mg Proteinase K, was added to each tube. Additional components, including anionic surfactants (SDS, Sarkosyl) and cationic surfactants (CTAB, CTACl, and tetramethl ammonium chloride) were added to specific tubes, as shown in Table 7.

TABLE 7

| Tube # | Additional Reaction Composition Components |
|---|---|
| 1 | No additional components (control) |
| 2 | 1% Sodium Dodecyl Sulfate (SDS) |
| 3 | 1% SDS, 10% 1-Methyl-2-pyrolidinone |
| 4 | 1% SDS, 100 mM Phenylglyoxal |
| 5 | 1% SDS, 80% RNA Later |
| 6 | 1% SDS, 80% Streck Tissue Fixative |
| 7 | 1% Cetyltrimethylammonium bromide (CTAB) |
| 8 | 1% CTAB, 10% 1-Methyl-2-pyrolidinone |
| 9 | 1% CTAB, 100 mM Phenylglyoxal |
| 10 | 1% CTAB, 80% RNA Later |
| 11 | 1% CTAB, 80% Streck Tissue Fixative |
| 12 | 1% Sarkosyl |
| 13 | 1% Sarkosyl, 10% 1-Methyl-2-pyrolidinone |
| 14 | 1% Sarkosyl, 10 mM Phenylglyoxal |
| 15 | 1% Sarkosyl, 80% RNA Later |
| 16 | 1% Sarkosyl, 80% Streck Tissue Fixative |
| 17 | 1% Cetyltrimethylammonium chloride (CTACl) |
| 18 | 600 mM Tetrabutylammonium chloride |
| 19 | 800 mM Tetramethylammonium chloride |

The tubes were incubated at 45° C. for 20 minutes with mixing (Eppendorf Thermomixer, Model 5436). Following the incubation, 171 µL of a solution containing 1.75 M NaCl, 29% Tween 20, 585 µg/ml glycogen (447 mM NaCl, 7.5% Tween 20, and 149 µg/ml glycogen) was added to each tube to dissolve the surfactant: nucleic acid complex. Glycogen served as a nucleic acid carrier. Undigested tissue fragments were removed by centrifugation using the methods the same as or similar to those discussed in Example 6. The supernatant was phenol extracted (saturated with 10 mM Tris HCl, pH 8, 1 mM EDTA; Sigma #P-4557), isopropanol precipitated (Aldrich #19076-4), and ethanol washed using methods the same as or similar to those described in Example 6. The washed nucleic acid pellets were resuspended with 100 µL 10 mM Tris, pH 8.0, 0.1 mM EDTA, and 1 unit/µL Rnasin. The amount of nucleic acid released and its integrity were evaluated as described in Example 6.

Figure 5:
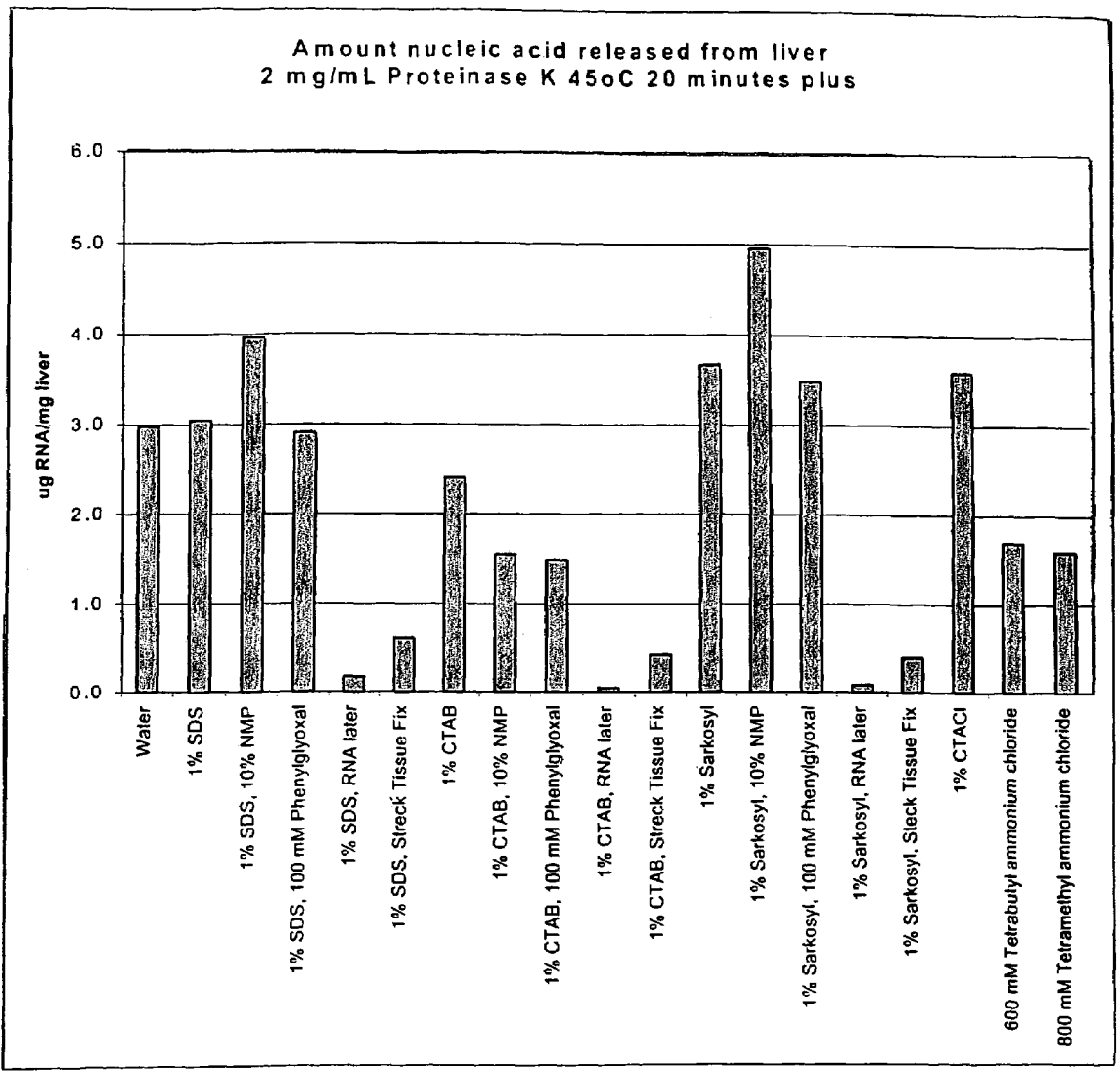
FIG. 5 illustrates the quantity of nucleic acid that is released and isolated from liver slices incubated for 20 minutes at 45° C. in reaction compositions comprising 2 mg/ml Proteinase K and the indicated surfactants. When used in these figures, NMP is 1-methyl-2-pyrolidinone.
Figure 6:
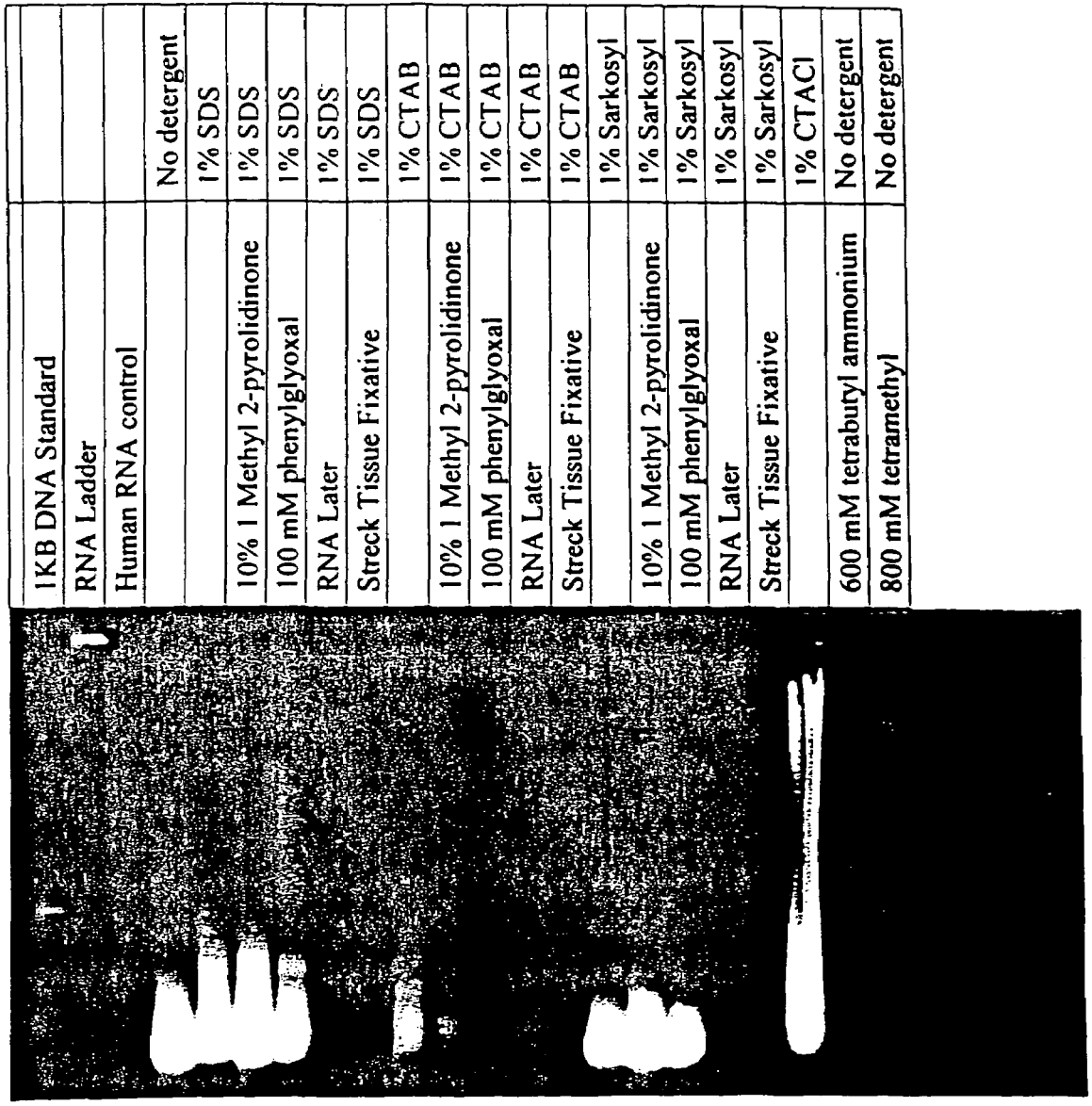
FIG. 6 depicts an ethidium bromide stained agarose gel that demonstrates the quality (integrity) of the released and isolated nucleic acid of FIG. 5.

As shown in FIG. 5, under these conditions, Proteinase K combined with either of the cationic surfactants (CTAB and CTACl) or the anionic surfactants (SDS and Sarkosyl) released $A_{260}$ absorbing material from the sample. When either Streck Tissue Fixative or RNA Later was added to these reactions, very little $A_{260}$ absorbing material was released. The average molecular weight for the released nucleic acid was typically higher when Proteinase K digestion was carried out at the lower pH and temperatures (compare FIG. 4 to FIG. 6). Additionally, the average molecular weight for the released nucleic acid was typically higher when Proteinase K digestion was performed in the presence of the cationic surfactants (compare Lanes 5-9 and 15-19 to 10-14 in FIG. 6).

Example 8

To compare CTACl to CTAB, those two surfactants were evaluated in parallel along with hexadecyltrimethylammonium bromide (HDTAB), hexadecyltrimethylammonium chloride (HDTACl), and Sarkosyl. Three additives, phenylglyoxal, acridine orange (e.g., Sigma #A6014), and 1-methyl-2-pyrolidinone, were also evaluated. Phenylglyoxal was tested to determine if it would reduce RNAse activity. Acridine Orange, a dye compound known to interact with nucleic acid molecules, was tested to determine if it would reduce nuclease activity. 1-Methyl-2-pyrrolidinone was tested to see if it would enhance solubility of the sample by various reaction compositions.

Slices of liver-tissue (100-200 mg/sample) were placed into twenty-one Eppendorf tubes. Four hundred microliters of a reaction composition, comprising 100 mM MES, pH 6, 20 mM $CaCl_2$, and 1 mg Proteinase K, was added to each tube. Additional components were added to specific tubes, as shown in Table 8.

TABLE 8

| Tube # | Additional Reaction Composition Components |
|---|---|
| 1 | 1% Cetyltrimethylammonium Bromide (CTAB) |
| 2 | 1% CTAB, 100 mM Phenylglyoxal |
| 3 | 1% CTAB, 10% 1-Methyl-2-pyrolidinone |
| 4 | 1% CTAB, 200 µg/ml Acridine orange |
| 5 | 1% Cetyltrimethylammonium Chloride (CTACl) |
| 6 | 1% CTACl, 100 mM Phenylglyoxal |
| 7 | 1% CTACl, 10% 1-Methyl-2-pyrolidinone |
| 8 | 1% CTACl, 200 µg/ml Acridine orange |
| 9 | 1% Hexatrimethylammonium Bromide (HTMAB) |
| 10 | 1% HTMAB, 100 mM Phenylglyoxal |
| 11 | 1% HTMAB, 10% 1-Methyl-2-pyrolidinone |
| 12 | 1% HTMAB, 200 µg/ml Acridine orange |
| 13 | 1% Hexatrimethylammonium Chloride (HTMACl) |
| 14 | 1% HTMACl, 100 mM Phenylglyoxal |
| 15 | 1% HTMACl, 10% 1-Methyl-2-pyrolidinone |
| 16 | 1% HTMACl, 200 µg/ml Acridine orange |
| 17 | 1% Sarkosyl (N-lauryl sarcosine) |
| 18 | 1% Sarkosyl, 100 mM Phenylglyoxal |
| 19 | 1% Sarkosyl, 10% 1-Methyl-2-pyrolidinone |
| 20 | 1% Sarkosyl, 200 µg/ml Acridine orange |
| 21 | No additives |

The tubes were incubated at 45° C. for 30 minutes with mixing (Eppendorf Thermomixer, Model 5436). Surfactant: protease complexes were solubilized using methods the same as or similar to those described in Example 7. Remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended and the amount and the integrity of the released nucleic acid were evaluated using methods the same as or similar to those described in Example 6.

Figure 7:
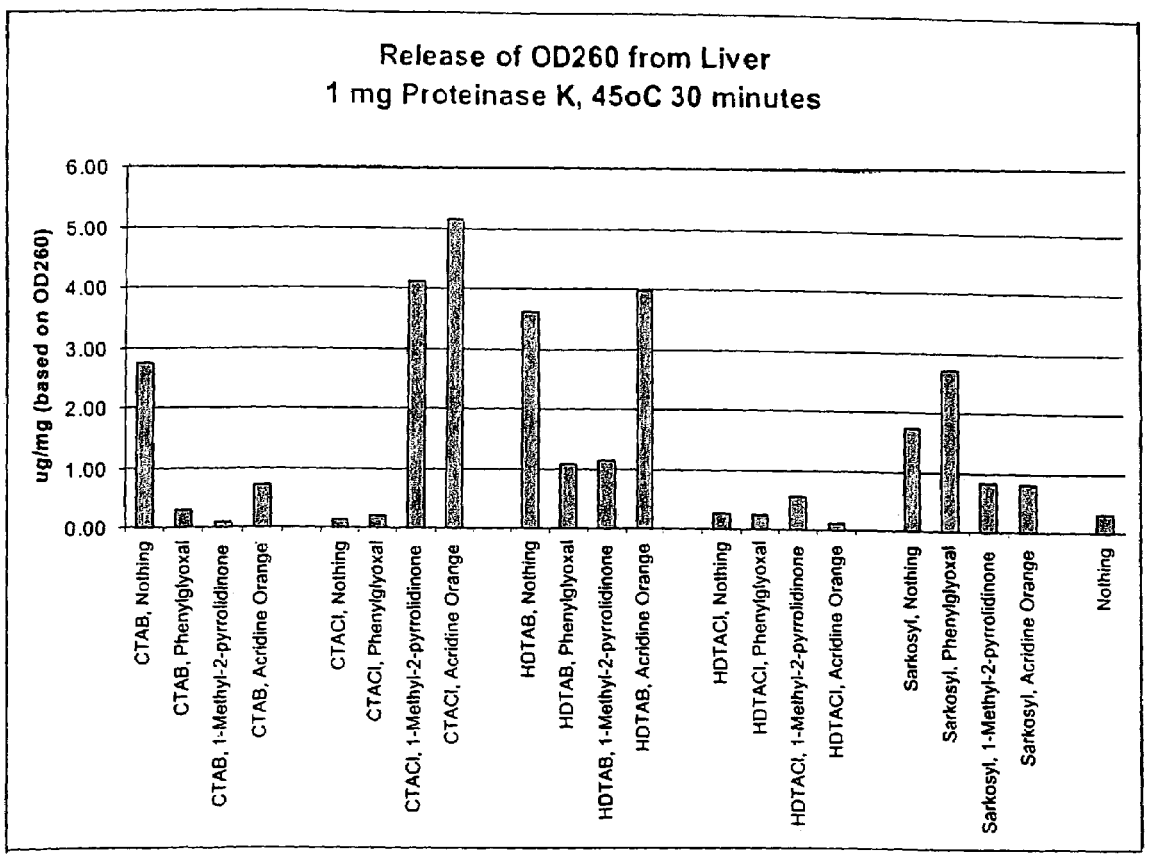
FIG. 7 illustrates the quantity of nucleic acid that is released and isolated from liver slices incubated for 30 minutes at 45° C. in reaction compositions comprising 1 mg/ml Proteinase K and the indicated surfactants and additives. When used in these figures, "nothing" means no additional reagent was added.

As shown in FIG. 7, the effect of the three additives varied depending on the surfactant. For example, the amount of nucleic acid released using CTACl and 1-methyl-2-pyrolidinone was greater in comparison with a composition of CTACl without an additive. However, the amount of nucleic acid released using HDTAB and 1-methyl-2-pyrolidinone was less in comparison with a composition of HDTAB without an additive.

Figure 8:
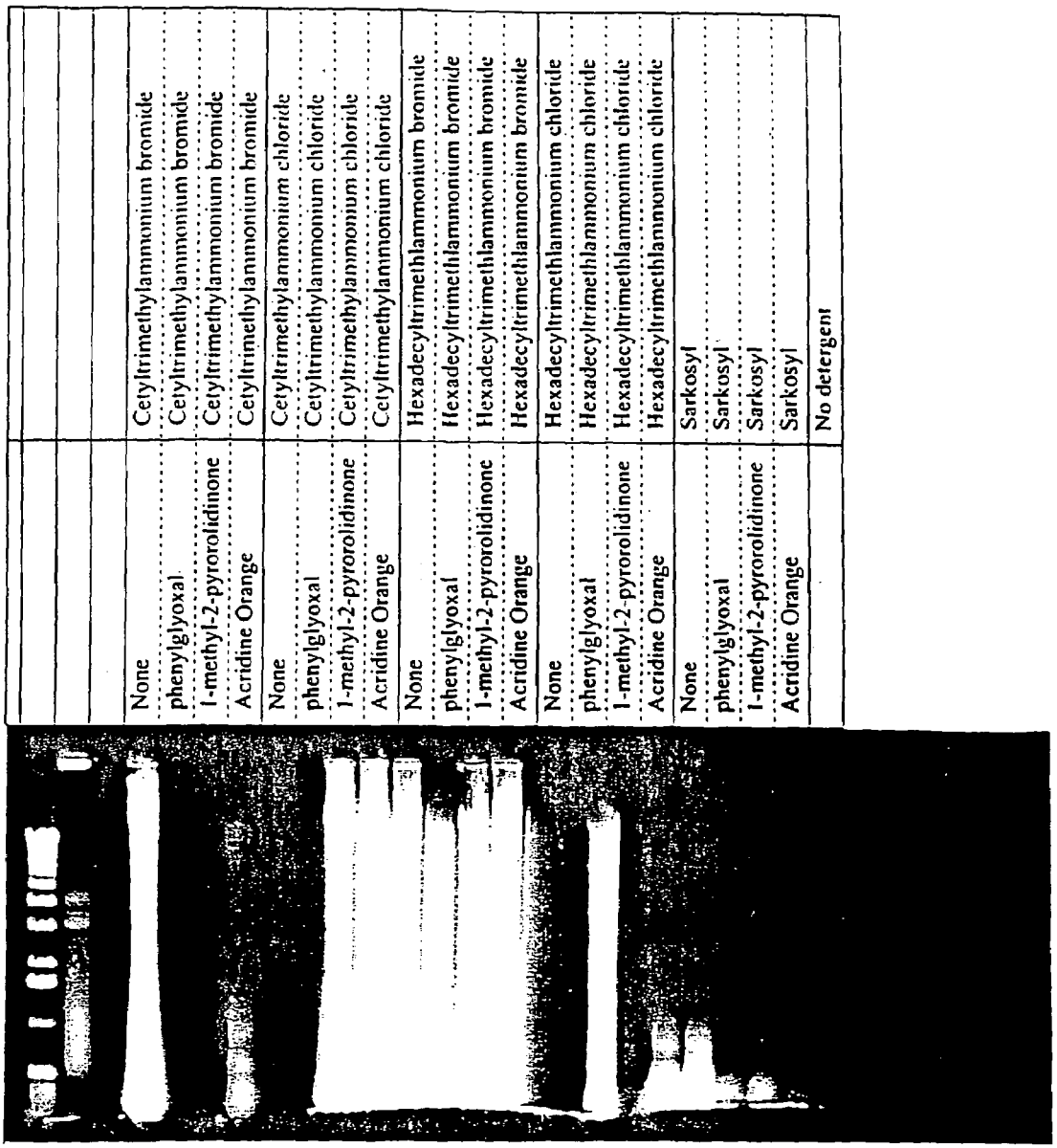
FIG. 8 depicts an ethidium bromide stained agarose gel that demonstrates the quality (integrity) of the released and isolate nucleic acid of FIG. 7.

When the released nucleic acid was analyzed by gel electrophoresis, high molecular weight nucleic acid was apparent in all reaction compositions containing HDTAB (see FIG. 8). High molecular weight nucleic acid was also present in reaction compositions containing CTACl and either 1-methy-2-pyrolidinone or acridine orange. High molecular weight nucleic acid was also observed in the reaction composition comprising HDTACl and 1-methyl-2-pyrolidinone.

Example 9

Example 7 demonstrated that the presence of certain reagents that have been used to stabilize RNA in tissue samples (i.e. Streck Tissue Fixative and RNA Later) inhibited the activity of Proteinase K. To attempt to reduce this inhibition, tissue was pre-incubated in several reagents to allow them to diffuse into the sample. Residual reagent was removed prior to incubation of the samples in reaction compositions.

Liver slices were incubated in various solutions prior to exposure to reaction compositions as follows. Slices of liver tissue (94-330 mg/sample) were placed into four sets of six Eppendorf tubes. Five hundred microliters of either Nucleic Acid Purification Lysis Solution, RNA Later, or Streck Tissue Fixative was added to one set of tubes. The fourth set of tubes contained no pretreatment solution and served as a control.

The tubes were incubated for 4 hours at 4° C., then centrifuged in an Eppendorf microfuge (Model 5415C) at ambient temperature for 2 minutes at 14,000 RPM. The supernatant was discarded and four hundred microliters of a reaction composition comprising 100 mM MES, pH 6.0, 20 mM $CaCl_2$, and 1 mg Proteinase K, was added to each tube. One of the six additional components shown in Table 9 was also added to each tube. The tubes were incubated at 45° C. with mixing (Eppendorf Thermomixer, Model 5436) for 30 minutes.

The resulting surfactant: protease complex was solubilized using methods the same as or similar to those described in Example 7. Remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended and the amount of nucleic acid released and the integrity of that nucleic acid were evaluated using methods the same as or similar to those described in Example 6.

TABLE 9

| Tube | Additional Reaction Composition Components |
|------|---------------------------------------------|
| 1 | 1% Cetyltrimethylammonium Bromide (CTAB) |
| 2 | 1% CTAB, 10% 1-methyl-2-pyrolidinone (NMP) |
| 3 | 1% CTAB, 200 µg/ml Acridine Orange |
| 4 | 1% Cetyltrimethylammonium Chloride (CTACl) |
| 5 | 1% CTACl, 10% NMP |
| 6 | 1% CTACl, 200 µg/ml Acridine Orange |

Figure 9:
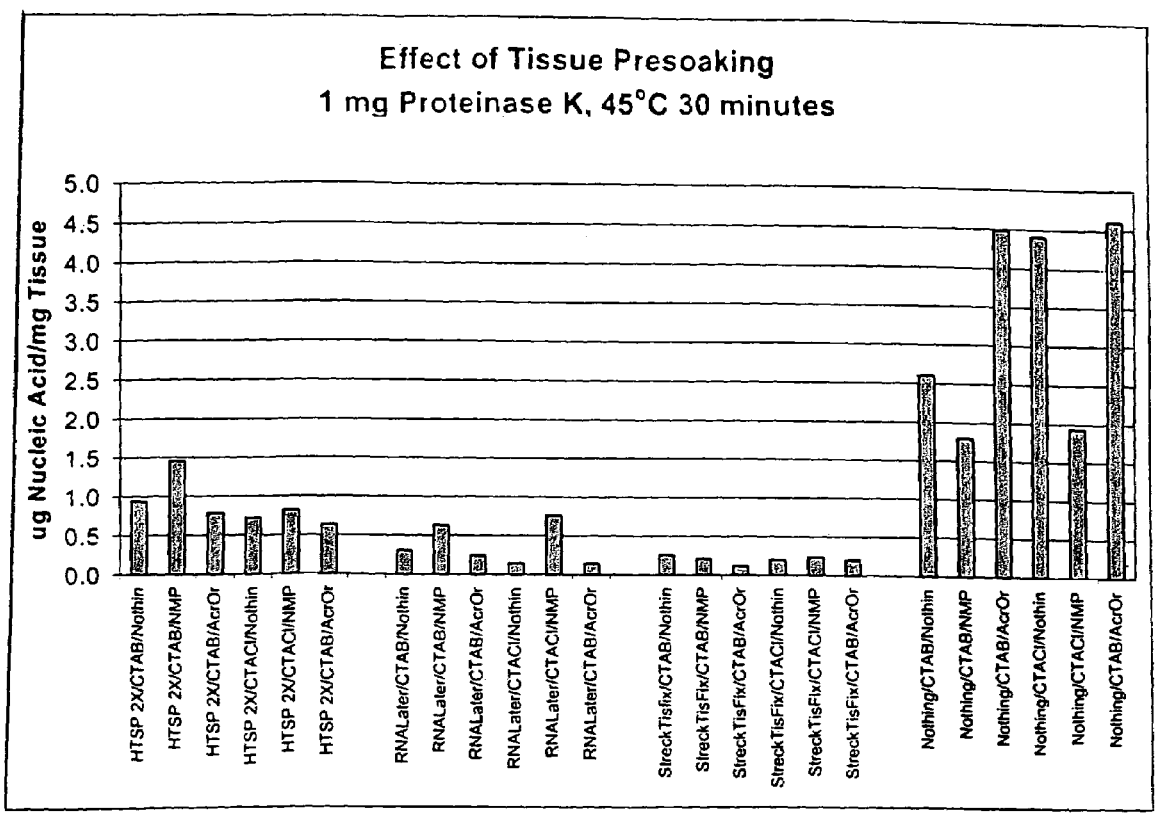
FIG. 9 illustrates the effect of exposing liver slices to pretreatment solutions prior to incubation for 30 minutes at 45° C. in reaction compositions comprising 1 mg/ml Proteinase K and the indicated surfactants and additives. When used in these figures, HTSP 2X means Nucleic Acid Purification Lysis Solution; AcrOr means acridine orange.
Figure 10:
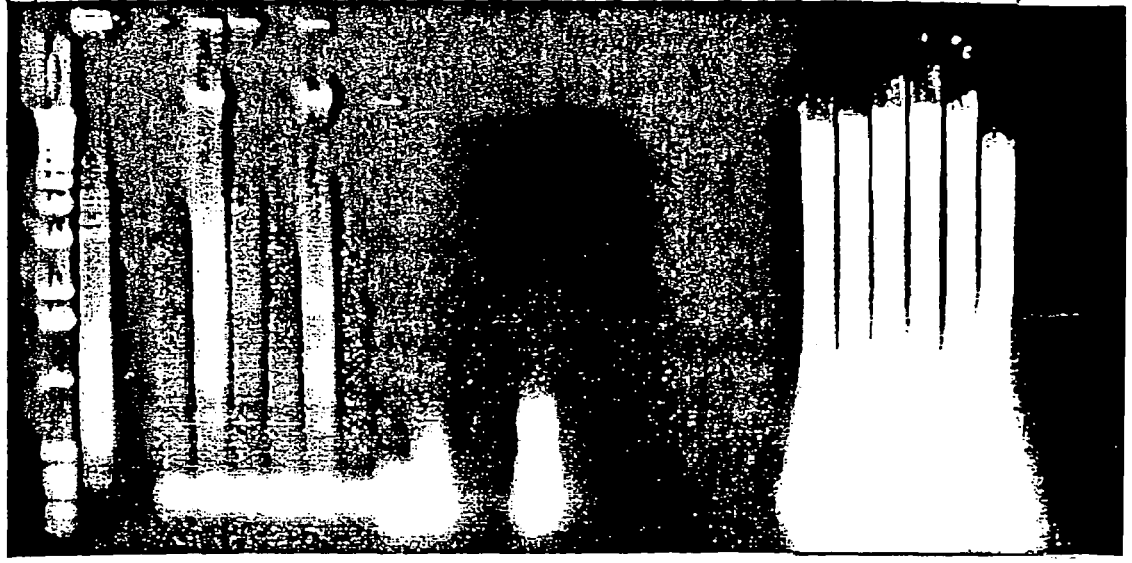
FIG. 10 depicts a stained agarose gel that demonstrates the quality of nucleic acid released and isolated from samples that were incubated in pretreatment solutions prior to surfactant: Proteinase K treatment.

As shown in FIG. 9, pretreatment of the samples with one of the pretreatment solutions resulted in a decreased amount of $A_{260}$-absorbing material that was released when compared to the control.

Example 10

The ability of aurintricarboxylic acid to maintain the integrity of the nucleic acid released using reaction compositions comprising CTAB, CTACl, or SDS, was evaluated. Aurintricarboxylic acid is believed to inhibit the binding of proteins, e.g., nucleases, to nucleic acid and has been demonstrated to inhibit ribonucleases. Slices of liver tissue (77-186 mg/sample) were placed into twenty-one Eppendorf tubes. To each tube was added 400 µL of a reaction composition comprising 50 mM MES, pH 6.0, 20 mM $CaCl_2$, and additional components as shown in Table 10.

TABLE 10

| Tube | Additional Reaction Composition Components |
|------|---------------------------------------------|
| 1 | 1% CTAB, 5 mM Aurintricarboxylic Acid |
| 2 | 1% CTAB, 2 mM Aurintricarboxylic Acid |
| 3 | 1% CTAB, 1 mM Aurintricarboxylic Acid |
| 4 | 1% CTAB, 0.5 mM Aurintricarboxylic Acid |
| 5 | 1% CTAB, 0.2 mM Aurintricarboxylic Acid |
| 6 | 1% CTAB, 0.1 mM Aurintricarboxylic Acid |
| 7 | 1% CTAB |
| 8 | 1% CTACl, 5 mM Aurintricarboxylic Acid |
| 9 | 1% CTACl, 2 mM Aurintricarboxylic Acid |
| 10 | 1% CTACl, 1 mM Aurintricarboxylic Acid |
| 11 | 1% CTACl, 0.5 mM Aurintricarboxylic Acid |
| 12 | 1% CTACl, 0.2 mM Aurintricarboxylic Acid |
| 13 | 1% CTACl, 0.1 mM Aurintricarboxylic Acid |
| 14 | 1% CTACl |
| 15 | 1% SDS, 5 mM Aurintricarboxylic Acid |
| 16 | 1% SDS, 2 mM Aurintricarboxylic Acid |
| 17 | 1% SDS, 1 mM Aurintricarboxylic Acid |
| 18 | 1% SDS, 0.5 mM Aurintricarboxylic Acid |
| 19 | 1% SDS, 0.2 mM Aurintricarboxylic Acid |
| 20 | 1% SDS, 0.1 mM Aurintricarboxylic Acid |
| 21 | 1% SDS |

The tubes were incubated at 55° C. with mixing (Eppendorf Thermomixer, Model 5436) for 30 minutes. The resulting surfactant-protease complex was solubilized using methods the same as or similar to those described in Example 7. Undigested tissue fragments were removed by centrifugation using methods the same as or similar to those described in Example 7. The supernatant was phenol extracted, isopropanol precipitated and ethanol washed using methods the same as or similar to those described in Example 6. The washed nucleic acid pellets were resuspended and the integrity of the released nucleic acid were evaluated using methods the same as or similar to those described in Example 6.

Figure 11:
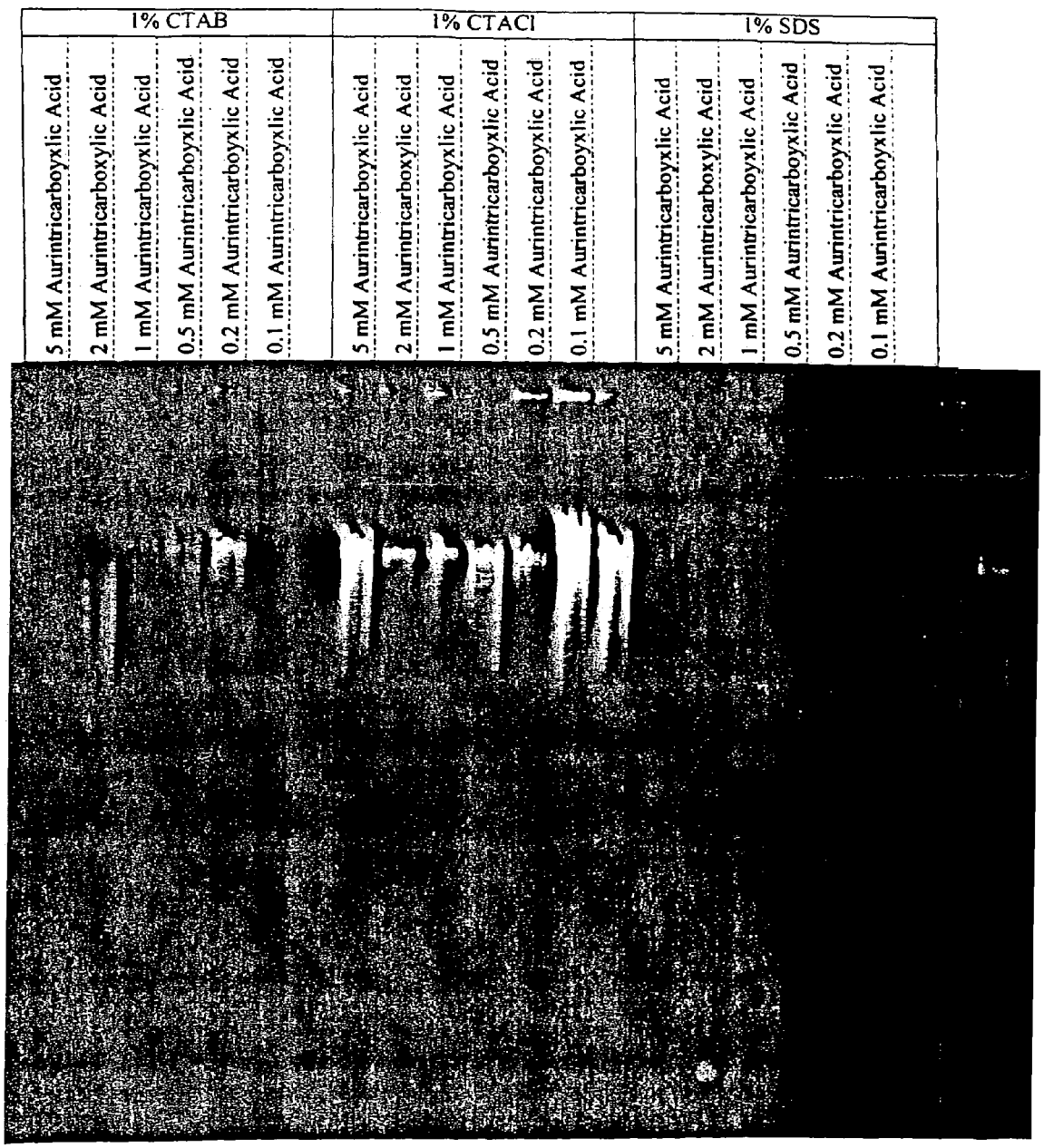
FIG. 11 depicts a stained agarose gel that demonstrates the quality of nucleic acid released and isolated using reaction compositions comprising varying amounts of aurintricarboxylic acid.

As shown in FIG. 11, the presence of aurintricarboxylic acid in the reaction composition enhanced the yield of high molecular weight nucleic acid. Reaction compositions containing aurintricarboxylic acid and either CTAB or CTACl released a large amount of high integrity nucleic acid. When SDS was the surfactant in the reaction composition, less nucleic acid was released.

Example 11

To examine the ability of other cationic reagents to release high integrity nucleic acid, additional compounds were tested as follows. Slices of liver tissue (80-140 mg/sample) were placed into fourteen Eppendorf tubes. Five hundred microliters of a reaction composition comprising 100 mM MES, pH 6, 20 mM $CaCl_2$, 0.5 mM aurintricarboxylic acid (e.g., Sigma #A1895), and 1 mg Proteinase K, was added to each tube. One of the cationic reagents shown in Table 11, was added to each tube to a final concentration of 1%. As a control, one tube contained no additional reagent. The tubes were incubated at 60° C. for 30 minutes with mixing (Eppendorf Thermomixer, Model 5436). Following the incubation, 200 µL of a solution containing 1.75 M NaCl, 29% Tween 20, and 585 µg/ml glycogen (resulting in a final concentration of 447 mM NaCl, 7.5% Tween 20, and 149 µg/ml glycogen) was added to each tube to dissolve the surfactant:nucleic acid complex. The remaining tissue fragments were removed by centrifugation using methods the same as or similar to those described in Example 7. The supernatant was phenol extracted, isopropanol precipitated, and ethanol washed using methods the same as or similar to those described in Example 6. The washed nucleic acid pellets were resuspended in 100 µL 10 mM Tris, pH 8.0, 0.1 mM EDTA, and 1 unit/µL Rnasin. The amount of nucleic acid released and its integrity were evaluated using methods the same as or similar to those described in Example 6.

TABLE 11

| Tube | Cationic Reagent |
|---|---|
| 1 | dodecyltrimethylammonium bromide (DTAB) |
| 2 | tetradecyltrimethylammonium bromide (TTAB) |
| 3 | CTAB |
| 4 | CTACl |
| 5, 6 | HTAB |
| 7 | Mackernium 006 (polyquaternium 6) |
| 8 | Mackernium (Olealkonium chloride) |
| 9 | Mackernium NLE (Quaternium-84) |
| 10 | Mackernium 007 (Polyquaternium 7) |
| 11 | Mackernium Stearalkonium SDC85 Chloride |
| 12 | Benzalkonium chloride |
| 13 | SDS |

Figure 12:
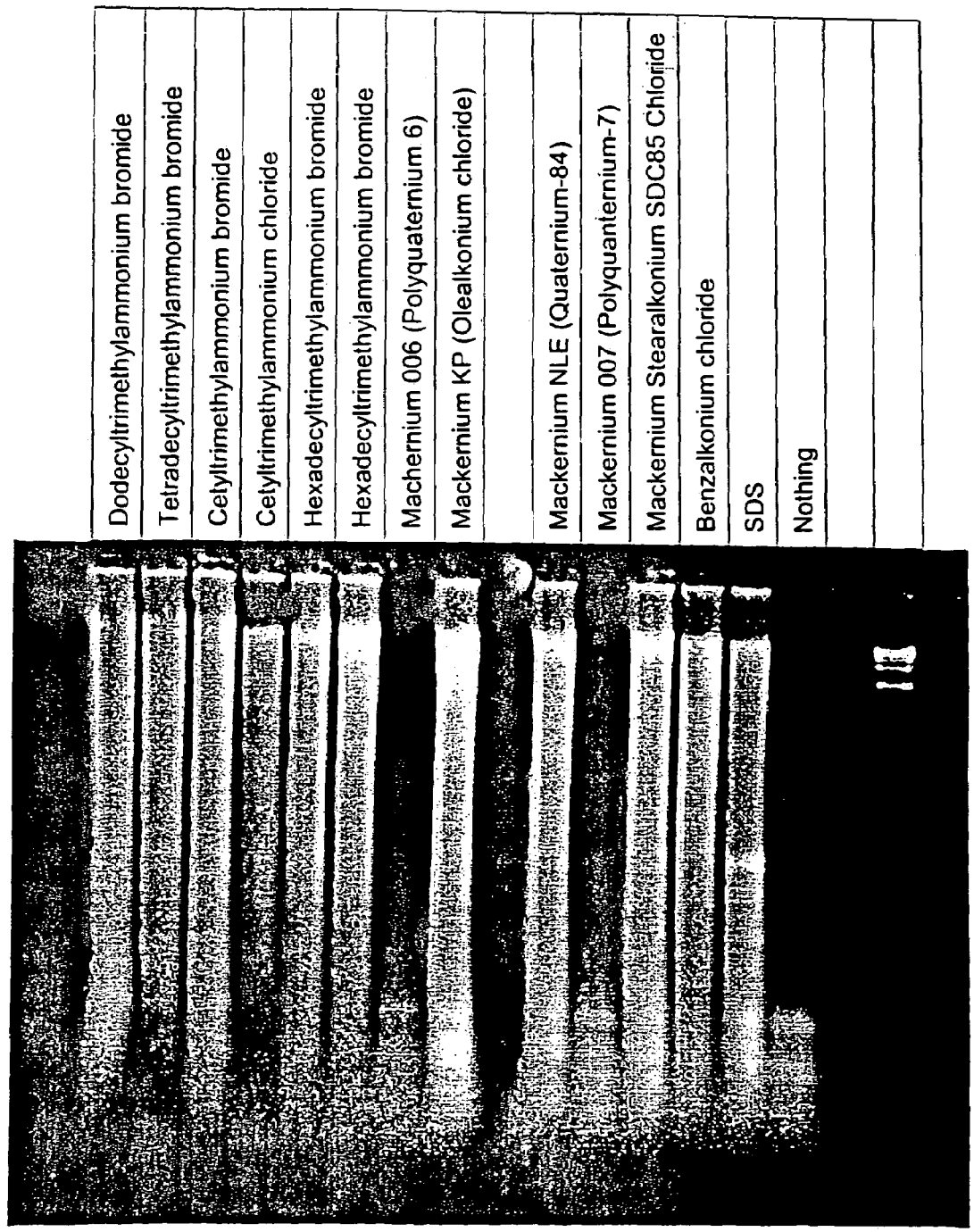
FIG. 12 depicts a stained agarose gel that provides a comparison of the amount and integrity of nucleic acid released and isolated with various cationic compounds.

As shown in FIG. 12, all of the cationic reagents tested, except for Mackernium 006 and 007, released high integrity nucleic acid. Of the eleven cationic reagents tested, nine were surfactants and two, Mackernium 006 and 007, were cationic polymers. This result demonstrates that, under these conditions, all of the cationic surfactants when used in conjunction with Proteinase K, effectively released nucleic acid from the sample.

The following terms, abbreviations, and sources apply to the materials discussed throughout Examples 12 to 21.

Solid phase glass fiber membranes, GF/B and GF/D, were obtained from Whatman Biosciences (Cat. Nos. 1821-150 and 1823-150). Proteinase K was obtained from Ambion (Cat. No. 2548). Rat and mouse tissues were taken from animals provided by Pel-Freeze Biologicals (Rogers, Ark.). Calf thymus genomic DNA was obtained from Sigma (Product No. D 8515).

Abbreviations or names of the following reagents and sources for them are as follows:

In the following Examples, these following cationic surfactants were used: cetyltrimethylammonium bromide (CTAB, Aldrich #85582-0), cetyltrimethylammonium chloride (CTACl, Aldrich #29273-7), dodecyltrimethylammonium bromide (DTAB, Sigma #D-8638), dodecyltrimethylammonium chloride (DTACl, Fluka Product Number 44242), octyltrimethylammonium bromide, tetradecyltrimethylammonium bromide (TTAB, Sigma Product No. T 4762), tetradecyltrimethylammonium chloride (TTACl, Fluka Product No. 87212), dodecylethyldimethylammonium bromide (DEDTAB, Fluka Product No. 44165), decyltrimethylammonium bromide ($D_{10}$TAB, Fluka Product No. 30725), dodecyltriphenylphosphonium bromide (DTPB, Research Chemicals Product No. 14295), quaternium 84 (MNLE or Mackernium NLE; McIntyre Group, Ltd.), olealkonium chloride (Mackernium KP or MKP; McIntyre Group, Ltd.), and wheat lipid epoxide (MWL or Mackernium NLE; McIntyre Group, Ltd.).

Abbreviations or names of the following reagents and sources for them are as follows: sodium dodecylsulfate (SDS, Ambion Cat. No. 9822), lithium dodecylsulfate (LDS, Sigma Product No. L4632 ), sodium N-lauroylsacrosinate or lauroyl sarkosine (Sarkosyl, Sigma Product No. L 5125), t-octylphenoxypolyethoxyeihanol (Triton X-100, Sigma Product No. T 8787), polyoxyethylenesorbitan monolaurate (Tween 20, Sigma Product No. P 9416), polyoxyethylenesorbitan monolaurate (Tween 21, Sigma Product No. P 2565), polyoxyethylenesorbitan monopalmitate (Tween 40, Sigma Product No. P 1504), polyoxyethylenesorbitan monostearate (Tween 60, Sigma Product No. P 1629), polyoxyethylenesorbitan monooleate (Tween 80, Sigma Product No. P 8074), polyoxyethylenesorbitan monotrioleate (Tween 85, Sigma Product No. P 4634), (octylphenoxy)polyethoxyethanol (IGEPAL CA-630/NP40, Sigma Product No. I 3021), triethyleneglycol monolauryl ether (Brij 30, Aldrich Product Number 23598-9), and sorbitan monolaurate (Span 20, Sigma Product Number S 6635).

Abbreviations or names of the following reagents and sources for them are as follows: guanidinium hydrochloride (Sigma, Lot 38H5432), guanidinium thiocyanate (Sigma, Product Number G-9277), sodium iodide (Aldrich Chemical Company, Product Number 38,311-2, Lot Number 07004TS), sodium perchlorate (Aldrich Chemical Company, Product Number 41,024-1, Lot KU 06910HU), sodium bromide (Aldrich, Product Number 31050-6, Lot 11805KR), sodium chloride (Aldrich Chemical Company, Product Number 33,251-4, Lot Number 16524CS), Tris (Trizma base, Tris[Hydroxymethyl]aminomethane, Sigma, Product Number T-6791, Lot Number 1261-15738), lithium iodide (Sigma Product Number L 4508), potassium iodide (Sigma Product Number P 2963), rubidium iodide (Sigma Product Number R 2252), cesium iodide (Sigma Product Number C 8643), lithium bromide (Aldrich 21,322-5), lithium chloride (Sigma Product Number L 9650), sodium thiocyanate (Sigma Product Number S 7757), urea (Sigma Product Number U 5378), EDTA (Ambion Catalog Number 9261), and sodium hydroxide (Sigma, Product Number S-8045, Lot Number 127H0531 and 69H1264).

Example 12

In certain instances, the solubility of detergents in high salt may relate to on the composition of the salt and the detergent itself. A mixing experiment was performed to examine the solubility of a variety of anionic, cationic, and nonionic surfactants in different salt compositions. Surfactants at a final concentration of 0.5% (Sarkosyl, LDS, SDS, and CTAB) or 5.0% (Triton X-100, Tween 20, Tween 21, Tween 40, Tween 60, Tween 80, Tween 85, NP-40, Brij 30, and Span 20) were added to salt solutions. The salt solutions contained LiI, NaI, KI, RbI, CsI, GuSCN, GuHCl, or $NaClO_4$, at pH 6.0 or 10.0. The concentration were 2M, 4M or 6M for a given salt, as indicated in Table 12. Some salt solutions included 8M urea and others did not include 8M urea. The solubility of the surfactants was scored as either soluble or insoluble. The solubility of the surfactant in the salt solution was determined initially by visual observations for cloudiness or precipitate formation. The resulting solutions were also centrifuged to verify the absence of a precipitate by the absence of a precipitate pellet. The surfactants that produced cloudiness in the solution or formed precipitates and precipitate pellet were scored insoluble (X) and the ones that resulted in clear solution with no apparent pellet formation after centrifugation were scored as soluble (S). Some detergents with "S(V)" scores dissolved in the salt solution but produced a noticeably viscous solution. The results are shown in Table 12. The insolubility that was observed appears to be independent of pH and was not changed by addition of the denaturing reagent urea.

Example 13

The solubilities of several cationic surfactants were examined in different chaotropic salt solutions. The cationic surfactants examined were cetyltrimethylammonium bromide (CTAB), cetyltrimethylammonium chloride (CTACl), tetradecyltrimethylammonium bromide (TTAB), tetradecyltrimethylammonium chloride (TTACl), dodecyltrimethylammonium bromide (DTAB), dodecyltrimethylammonium (DTACl), dodecylethyidimethylammonium bromide (DEDTAB), decyltrimethylammonium bromide ($D_{10}$TAB), and dodecyltriphenylphosphonium bromide (DTPB). Each of the cationic surfactants tested was presented in a 1% concentration. Each of the cationic surfactants was examined in a 5M solution of one of the chaotropic salts containing 2% Tween 20. Each cationic surfactant and salt combination was

TABLE 12

Solubility of Surfactants in Different Chaotropes at pH 6 & pH 10

| Chaotrope | | pH | Sarkosyl | LDS | SDS | CTAB | Triton X- | Tween 20 | Tween 21 | Tween 40 | Tween 60 | Tween 80 | Tween 85 | IGEPA | Brij 30 | Span 20 |
|---|---|---|---|---|---|---|---|---|---|---|---|---|---|---|---|---|
| 6 M LiI | | 6.0 | | | | | | | | | | | | | | |
| 6 M NaI | | 6.0 | S X | X | X | X | X | S | S | S | X | X | X | X | S | X |
| 6 M KI | | 6.0 | S X | X | X | X | X | X | X | X | X | X | X | X | X | X |
| 4 M RbI | | 6.0 | S | | | | | | | | | | | | | |
| 2 M CsI | | 6.0 | S | | | | | | | | | | | | | |
| 6 M GuSCN | | 6.0 | S | X | X | X | X | S | S | S | S | S | S | S | S | S |
| 6 M GuHCl | | 6.0 | S | X | X | S | S | S | X | S | X | S | X | S | S | X |
| 6 M NaClO$_4$ | | 6.0 | | X | X | X | X | X | X | X | X | X | X | X | X | X |
| 4 M LiI | Urea | 6.0 | | | | | | | | | | | | | | |
| 4 M NaI | Urea | 6.0 | S | X | X | X | S | S | S | S | X | S | S(V) | S | S(V) | X |
| 4 M KI | Urea | 6.0 | S | X | X | X | S | S | X | S | X | X | X | S | X | X |
| 4 M RbI | Urea | 6.0 | | | | | | | | | | | | | | |
| 4 M CsI | Urea | 6.0 | | | | | | | | | | | | | | |
| 4 M GuSCN | Urea | 6.0 | S | X | X | X | S | S | S | S | S | S | S | S | S | X |
| 4 M GuHCl | Urea | 6.0 | S | X | X | S | S | S | X | S | X | S | X | S | X | X |
| 4 M NaClO$_4$ | Urea | 6.0 | S | X | X | X | S | S | S | S | X | S | X | S | X | X |
| 6 M LiI | | 10.0 | | | | | | | | | | | | | | |
| 6 M NaI | | 10.0 | S X | X | X | X | S | S | X | S | X | X | X | S | X | X |
| 6 M KI | | 10.0 | S X | X | X | | X | X | X | X | X | X | X | X | X | X |
| 4 M RbI | | 10.0 | S | | | | | | | | | | | | | |
| 2 M CsI | | 10.0 | S | | | | | | | | | | | | | |
| 6 M GuSCN | | 10.0 | S | X | X | | X | S | S | S | S | S | S | S | S | S |
| 6 M GuHCl | | 10.0 | S | X | X | | S | S | X | S | X | X | X | X | S | X |
| 6 M NaClO$_4$ | | 10.0 | S X | X | X | | X | X | X | X | X | X | X | X | X | X |
| 4 M LiI | Urea | 10.0 | | | | | | | | | | | | | | |
| 4 M NaI | Urea | 10.0 | S | X | X | | S | S | S | S | X | S | S(V) | S | X | X |
| 4 M KI | Urea | 10.0 | S | X | X | | S | S | X | S | X | S | X | S | X | X |
| 4 M RbI | Urea | 10.0 | | | | | | | | | | | | | | |
| 4 M CsI | Urea | 10.0 | | | | | | | | | | | | | | |
| 4 M GuSCN | Urea | 10.0 | S | X | X | | S | S | S | S | S | S | S(V) | S | S | X |
| 4 M GuHCl | Urea | 10.0 | S | X | X | | S | S | X | S | X | S | X | S | X | X |
| 4 M NaClO$_4$ | Urea | 10.0 | S | X | X | | S | S | S | X | S | X | S | X | X | X |

X- Insoluble
S - Soluble tested at pH 6 (50 mM MES), pH 8 (50 mM Tris-HCl), and pH 10 (50 mM AMP). The solubility of each surfactant was visually evaluated and scored using the same criterion used in Example 12. The results are shown in Table 13.

chaotrope solution were separately added to six different tubes with DTAB and precipitate. Six hundred μl of each chaotrope solution were separately added to six different tubes with DTACl and precipitate. Results are shown in Table 13. Solutions were assessed for whether the DNA dissolved ("R") or didn't dissolve ("IR").

The nucleic acid precipitates dissolved in most chaotropic salt solutions, including in those solutions where the surfactant itself was not soluble.

TABLE 13

Solubility of cationic surfactants in different chaotropic solutions (5 M) containing 2% Tween 20

| Chaotrope (MW) | pH | CTAB | CTACl | TTAB | TTACl | DTAB | DTACl | DEDTAB | D$_{10}$TAB | DTPB |
|---|---|---|---|---|---|---|---|---|---|---|
| NaBr (102.9) | 6 | s | x | x | s | s R | s R | s | s | s |
|  | 8 | s | x | x | s | s | s | s | s | s |
|  | 10 | s | x | x | s | s | s | s | s | s |
| NaI (149.9) | 6 | x | x | x | x | x IR | x R | s | s | s |
|  | 8 | x | x | x | x | x | x | s | s | s |
|  | 10 | x | x | x | x | x | x | s | s | s |
| NaSCN (81.1) | 6 | x | x | x | x | s R | s R | s | s | s |
|  | 8 | x | x | x | x | s | s | s | s | s |
|  | 10 | x | x | x | x | s | s | s | s | s |
| LiCl (42.4) | 6 | s | s | s | s | s R | s R | s | s | s |
|  | 8 | s | s | s | s | s | s | s | s | s |
|  | 10 | s | s | x | s | x | s | s | s | s |
| LiBr (86.9) | 6 | x | x | s | s | s R | s R | s | s | s |
|  | 8 | x | x | s | s | s | s | s | s | s |
|  | 10 | x | x | X | x | x | x | X | x | X |
| LiI (133.8) | 6 | x | x | x | x | x R | s R | s | s | s |
|  | 8 | x | x | x | x | s | s | s | s | s |
|  | 10 | x | x | x | x | x | s | s | s | s |
| GuHCl (95.5) | 6 | s | s | s | s | s R | s R | s | s | s |
|  | 8 | s | s | s | s | s | s | s | s | s |
|  | 10 | s | s | s | s | s | s | s | s | s |
| GuSCN (118.2) | 6 | x | x | x | x | s R | s R | s | s | s |
|  | 8 | x | x | x | x | s | s | s | s | s |
|  | 10 | x | x | x | x | s | s | s | s | s |

Legend:
s - surfactant dissolved in solution
x - surfactant formed precipitate
R - DNA precipitate formed in 1.6% cationic surfactant, dissolved after addition of chaotropic solution, but surfactant precipitate did not dissolve
IR - DNA precipitate did not dissolve The results suggest a relationship between solubility and surfactant chain length. In addition, the radius of the counter anion also influences solubility of the detergent. Surfactants with alkyl chain lengths of 12 carbon atoms or shorter, such as DEDTAB, D10TAB, DTPB, DTAB and DTACl, appeared more soluble than larger surfactants. In the presence of the large anion iodide, some of the cationic surfactants were insoluble. All cationic surfactants were more soluble in both GuHCl and LiCl than other chaotropic salts.

Example 14

To verify that formation of surfactant-nucleic acid precipitate in the presence to DTAB and DTACl was reversible, the following experiment was performed. Calf thymus genomic DNA (Sigma) was partially sheared by passing three times through an 18 gauge hypodermic needle. Ninety microliters of a solution containing 8 μg of the sheared DNA was placed into each of 16 microfuge tubes. DTAB was added to a final 1.6% concentration to 8 of the tubes and DTACl was added to the remaining 8. The tubes were briefly vortexed and precipitation was noted in all the tubes. Eight chaotrope solutions were then prepared with 50 mM MES pH 6.0 and 5M of one of the following: NaBr, NaI, NaSCN, LiCl, LiBr, LiI, GuHCl or GuSCN. Six hundred μl of each Example 15

To attempt to obtain genomic DNA from rat tails, 50 mg rat tail pieces were macerated in microfuge tubes in 200 μl of buffer comprising 5 mg/ml Proteinase K, 100 mM Tris-HCl (pH 8.0), 20 μM ATA, 20 mM CaCl$_2$, and 1% of one of the following cationic surfactants: CTACl, CTAB, TTAB, DTAB, MNLE (quaternium 84, Mackernium NLE; Mcintyre Group, Ltd.), MKP(olealkonium chloride, Mackernium KP; Mcintyre Grp, Ltd), and MWL (wheat lipid epoxide, Mackernium WLE; Mcintyre Group, Ltd.). The tubes were incubated at 65° C. for 60 minutes with mixing at 1000 rpm (Eppendorf Thermomixer, Model 5436). From each tube, 100 μl and 50 μl aliquots were transferred to fresh tubes. Six hundred μl of chaotrope solution containing 5M GuSCN, 50 mM Tris-HCl, pH 8.0, 20 mM EDTA, and 2% Tween 20 was added to each tube and the solutions were mixed until the Schlerin patterns disappeared. To remove undigested tissue particulates such as hair and bones, the tubes were centrifuged at 4° C. for 5 minutes at 14,000 rpm. The released genomic DNA in the supernatant solution was isolated by glass filter-adsorption and vacuum-filtration method using the ABI PRISM 6100 Nucleic Acid PrepStation (Applied Biosystems Product Number 6100-01). The sample solutions were transferred to the glass fiber GF/B filters (in a 96-well format) and were evacuated with a 2.4 psi vacuum. The filters were washed three times with 90% ethyl alcohol. DNA was recovered from the glass fiber first by using 200 µl of TE solution (10 mM Tris, pH 8.0, 1 mM EDTA). Following a three minute incubation at room temperature, the DNA-containing eluate was evacuated and collected into a 96-well sample archive tray (ABI Prism 4306737, Applied Biosystems). A second separate elution was done with 100 µl of 0.1N NaOH.

Figure 13:
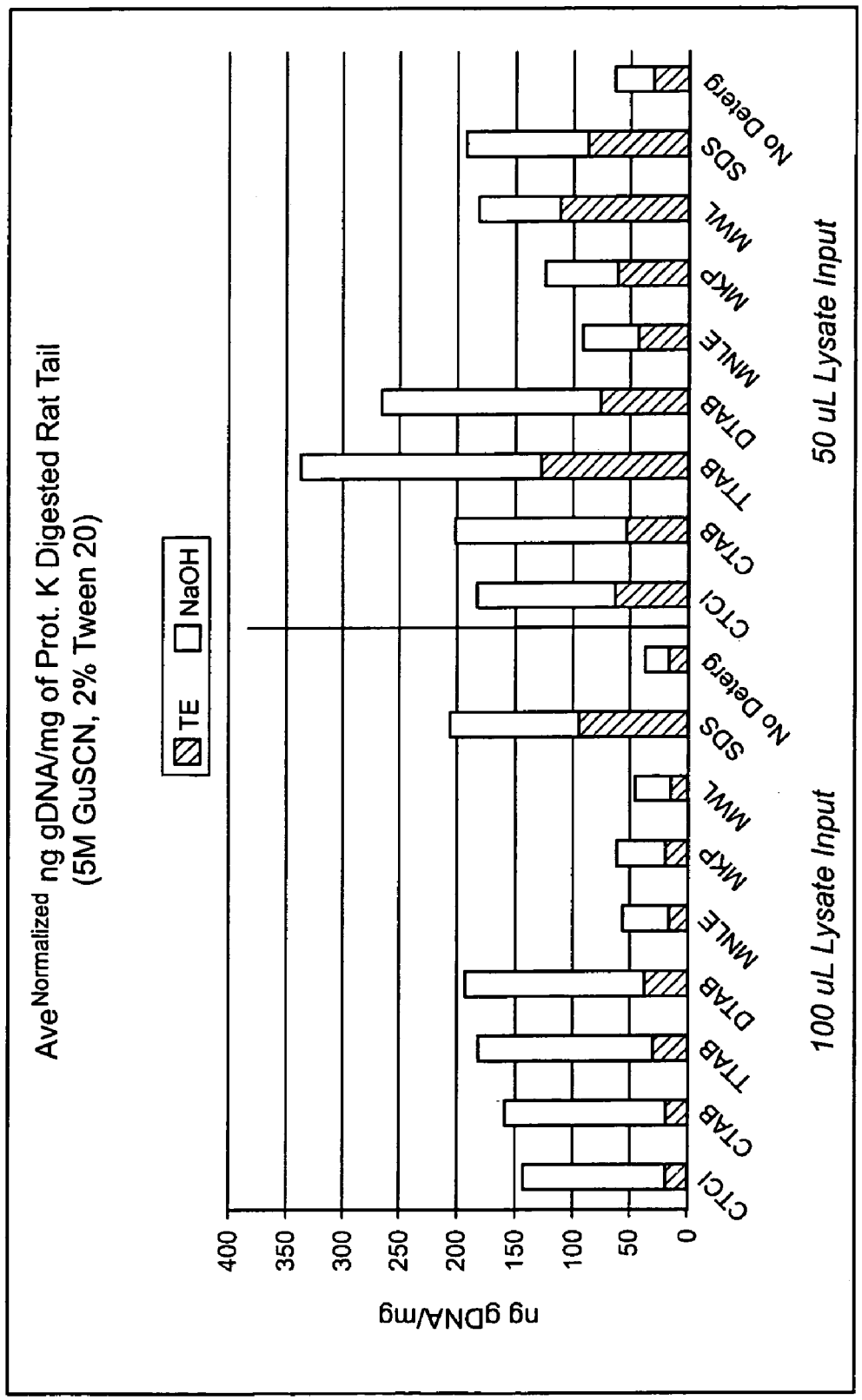
FIG. 13 shows the average efficiency of recovery of genomic DNA from Proteinase K digested rat tail using a variety of different surfactants in 5M GuSCN, 2% Tween 20, when eluting initially with TE (10 mM Tris, pH 8.0, 1 mM EDTA) followed by elution with 100 mM N NaOH. The values indicate the cumulative release of nucleic acid.

The results of the recovery are shown in FIG. 13 as a function of nanograms of DNA recovered per milligrams of rat tail tissue. In addition, it appears from the substantial increase in recovery by NaOH, that the DNA that was recovered eluted more efficiently under alkaline conditions.

Example 16

The ability of purified DNA to be reversibly bound to a GF/B glass fiber filter was assessed. Binding and release of genomic DNA was tested in the presence of 2% Tween 20 at three different pH levels (pH 6, 8, and 10), in the presence of one of three different salts (sodium thiocyanate, guanidinium thiocyanate, and sodium bromide), and in the either with one of two different cationic surfactants (DTAB and DTACl), or without any cationic surfactant. Eight micrograms of partially sheared calf thymus genomic DNA (prepared as in Example 15) was added to 600 µl DNA binding solution containing 5M of one salt (NaSCN, NaBr or GuSCN), 20 mM EDTA, 2% Tween 20, 50 mM buffer (one of MES, pH 6.0; Tris-HCl, pH 8.0; or AMP, pH 10) and 1% cationic surfactant (DTAB, DTACl, or water without surfactant as a control—"No Deterg."). Thus, there were 27 different combinations that were tested. The genomic DNA was adsorbed onto a glass filter by vacuum-filtration using the ABI PRISM 6100 Nucleic Acid PrepStation (Applied Biosystems Product Number 6100-01). The sample solutions were transferred to the glass fiber GF/B filter (in a 96-well format) and were evacuated with a 2.4 psi vacuum. The filters were washed three times with 90% EtOH. DNA was recovered from the glass fiber first by using 200 µl TE solution. Following a three minute incubation at room temperature, the DNA-containing eluate was evacuated and collected into the 96-well sample archive tray (ABI Prism 4306737, Applied Biosystems). A second separate elution was done with 100 µl of 0.1N NaOH.

Figure 14:
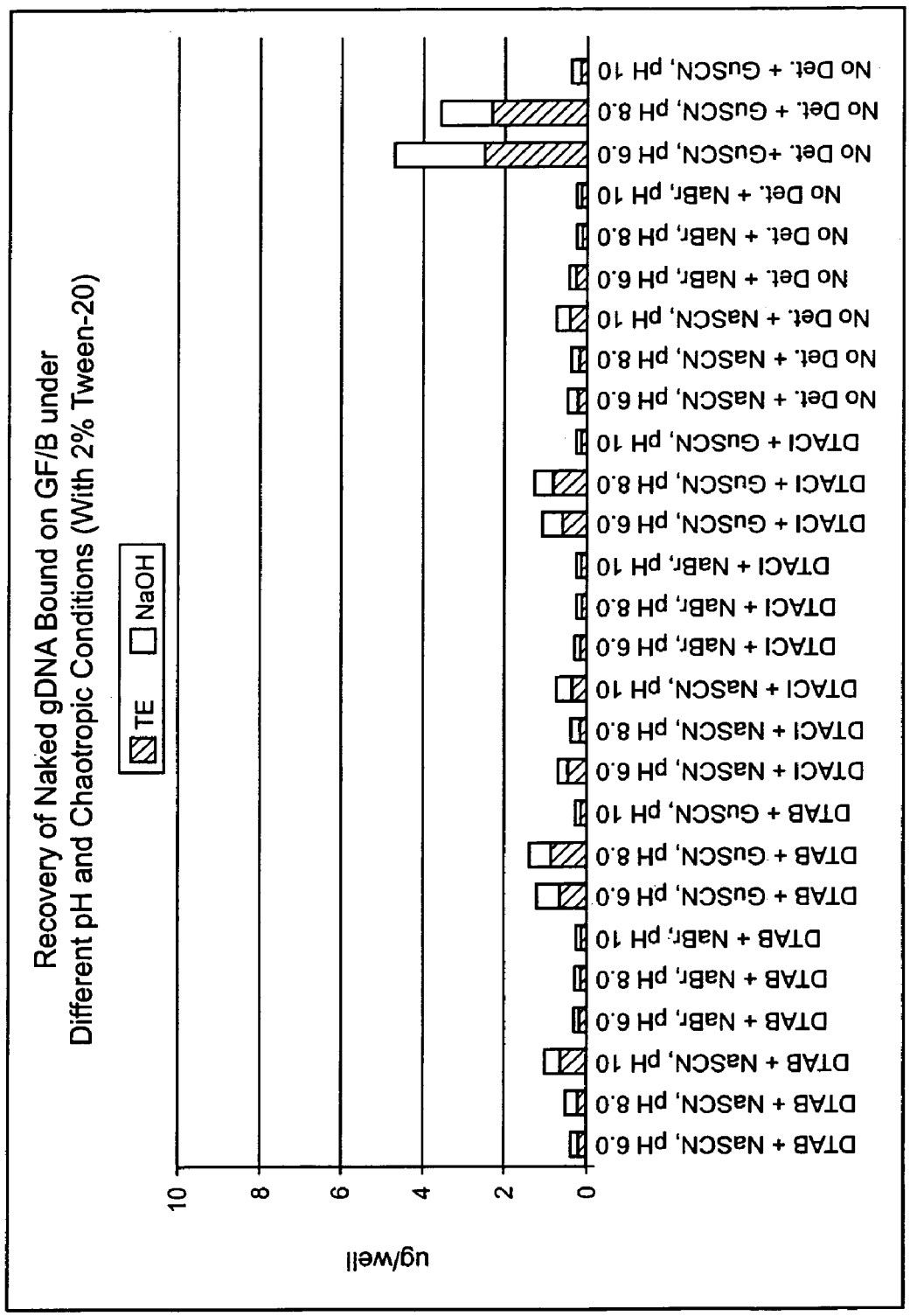
FIG. 14 shows the efficiency of recovery of genomic DNA from glass fiber GF/B filters in the presence of 2% Tween 20, using a number of different pH levels, salts, and surfactants when eluting initially with TE (10 mM Tris, pH 8.0, 1 mM EDTA) followed by elution with 100 mM NaOH. The values represent the cumulative release of nucleic acid.

Under most conditions, binding of purified DNA was poor, as shown in FIG. 14. When guanidinium thiocyanate was the binding salt, the presence of the cationic surfactants DTAB and DTACl appeared to inhibit the recovery of DNA.

Example 17

The effect of Tween-20 on DNA recovery was examined by repeating the experiment outlined in Example 15 without the presence of the nonionic surfactant (Tween 20). Eight micrograms of partially sheared calf thymus genomic DNA (prepared as in Example 15) was added to 600 µl DNA binding solution containing 5M of one salt (NaSCN, NaBr, or GuSCN), 20 mM EDTA, 50 mM buffer (one of MES, pH 6.0; Tris-HCl, pH 8.0; or AMP, pH 10) and 1% cationic surfactant (DTAB, DTACl, or water without surfactant as a control- "No Deterg."). Thus, there were 27 different combinations that were tested. The genomic DNA was adsorbed onto a glass filter by vacuum-filtration using the ABI PRISM 6100 Nucleic Acid PrepStation (Applied Biosystems Product No. 6100-01). The sample solutions were transferred to glass fiber GF/B filters (in a 96-well format) and were evacuated with a 2.4 psi vacuum. The filters were washed three times with 90% EtOH. DNA was recovered from the glass fiber first by using 200 µl TE solution. Following a three minute incubation at room temperature, the DNA-containing eluate was evacuated and collected into the 96-well sample archive tray (ABI Prism 4306737, Applied Biosystems). A second separate elution was done with 100 µl of 0.1N NaOH.

Figure 15:
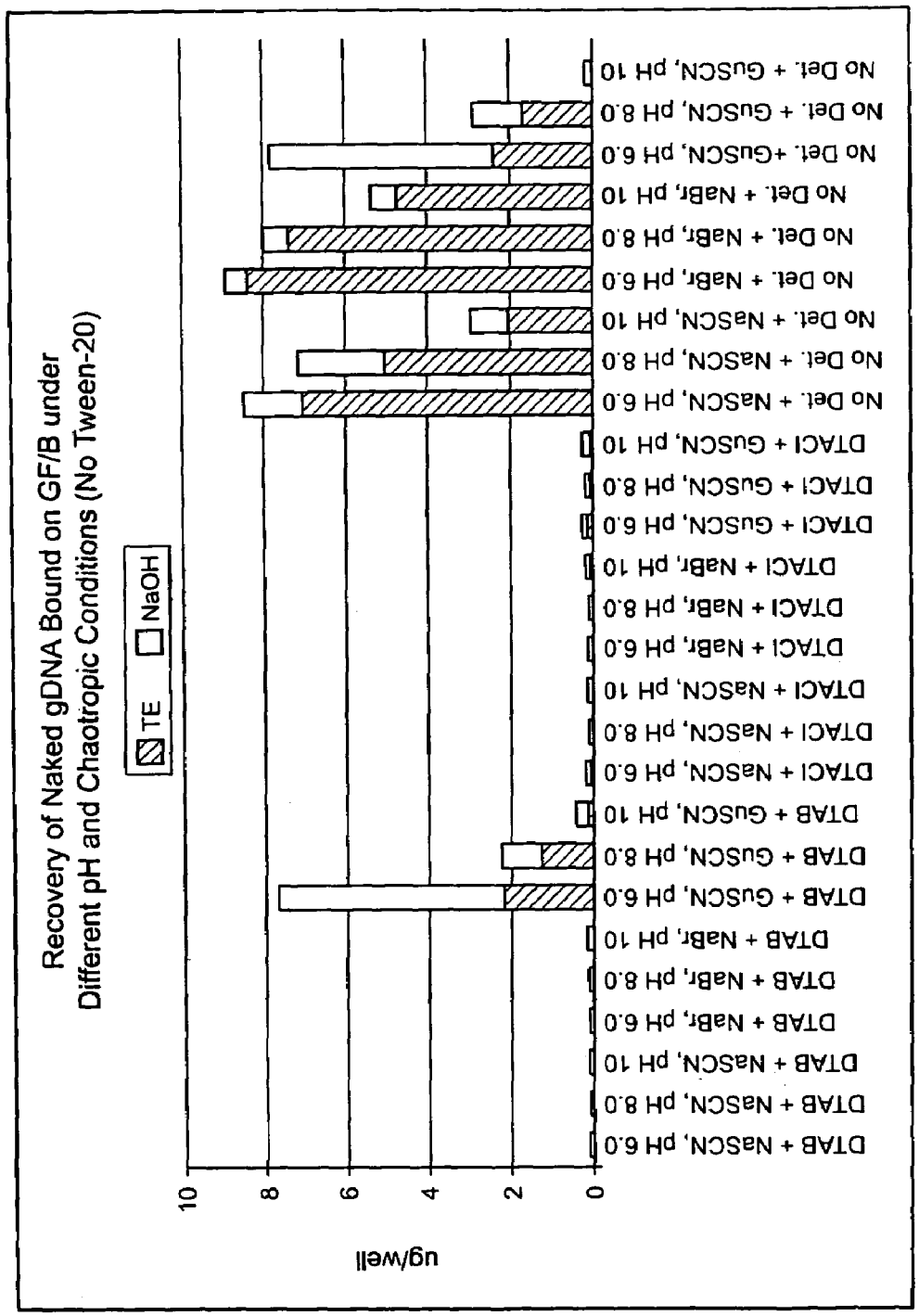
FIG. 15 shows the efficiency of recovery of genomic DNA from glass fiber GF/B filters in the absence of Tween 20, using a number of different pH levels, salts, and surfactants when eluting initially with TE (10 mM Tris, pH 8.0, 1 mM EDTA) followed by elution with 100 mM NaOH. The values represent the cumulative release of nucleic acid.

Even in the absence of Tween 20, all of the conditions assayed showed little recovery of DNA when bound to the glass fiber GF/B membrane (FIG. 15). The presence of guanidinium thiocyanate and DTAB showed some recovery. DNA could be recovered from GF/B by all three salts when no cationic surfactant was present during binding. (FIG. 15). Also, more DNA was recovered from GF/B at pH 6.0 than at pH 8.0 or pH 10.0.

Example 18

Figure 16:
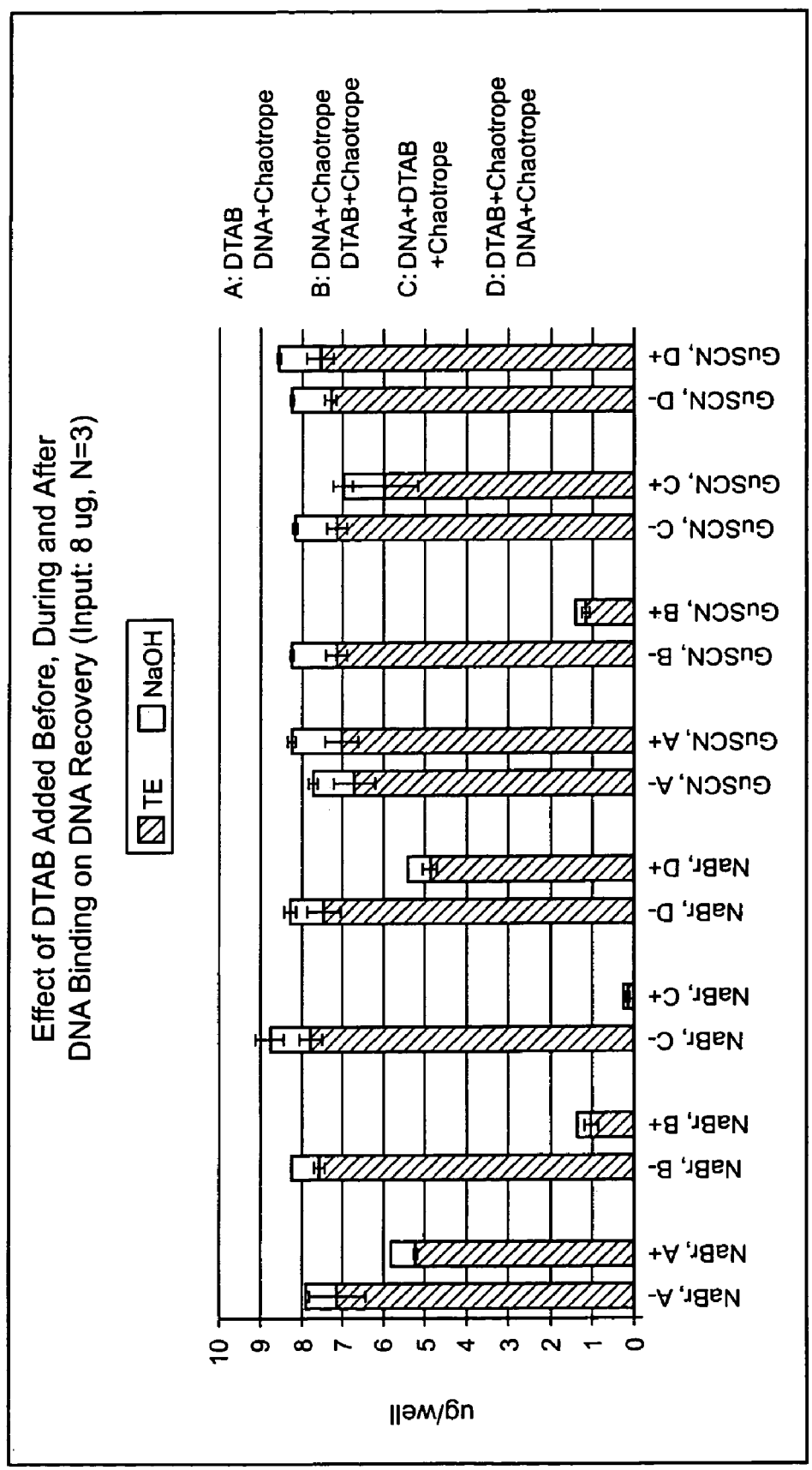
FIG. 16 shows the effect of the cationic surfactant docecyltrimethylmmonium bromide (DTAB) on DNA recovery when added before, during, and after DNA binding. The values represent the cumulative release of nucleic acid.

The inhibitory effect of the cationic surfactant, DTAB, was further examined. DTAB was introduced at various points of the purification reaction, before DNA binding, during binding, or after DNA binding has occurred on the solid phase. DNA binding and purification procedures were carried out using GF/B glass fiber filters (in a 96-well format) on the ABI PRISM 6100. The various purification conditions were designated A through D as shown in FIG. 16.

In set A, the GF/B membrane was pretreated with 100 µl of liquid lacking (A−) or containing (A+) 1% DTAB. Calf thymus DNA (8 µg) was then bound in 800 µL of 50 mM MES, pH 6.0, 20 mM EDTA, and 5 M salt (either NaBr or GUSCN). The membranes were then washed in 90% ethanol and the bound nucleic acid eluted first with 200 µl of TE, then followed by 100 mM NaOH.

In set B, the membranes were not prewashed. Calf thymus DNA (8 µg) was bound to GF/B glass fiber filters in 800 µl of 50 mM MES, pH, 6.0, 20 mM EDTA, and 5 M salt (either NaBr or GuSCN). Following binding, the membranes were washed in 50 mM MES, pH 6.0, 20 mM EDTA and 5 M salt (either NaBr or GuSCN) either lacking (B−) or containing (B+) 1% DTAB. The membranes were then washed in 90% ethanol and the bound nucleic acid eluted first with 200 µl of TE, then followed by 100 mM NaOH.

In set C, the membranes were not prewashed. Calf thymus DNA (8 µg) was bound to GF/B glass fiber filters in 800 µl of 50 mM MES, pH 6.0, 20 mM EDTA, and 5 M salt (either NaBr or GUSCN) either lacking (C−) or containing (C+) 1% DTAB. The membranes were then washed in 90% ethanol and the bound nucleic acid eluted first with 200 µl of TE, then followed by 100 mM NaOH In set D, the GF/B membrane was pretreated with 100 µl of 5 M salt (either NaBr or GuSCN) lacking (A−) or containing (A+) 1% DTAB. Calf thymus DNA (8 µg) was then bound in 800 µl of 50 mM MES, pH 6.0, 20 mM EDTA, and 5 M salt (either NaBr or GuSCN). The membranes were then washed in 90% ethanol and the bound nucleic acid eluted first with 200 µl of TE, then followed by 100 mM NaOH. The results are shown in FIG. 16.

When the GF/B membrane was pretreated with DTAB (A+), and the DNA bound in the presence of GuSCN or NaBr without DTAB, DNA recovery from the GF/B membrane was not significantly reduced compared to recovery from a GF/B membrane which was not pretreated with DTAB (A−). Therefore, in this experiment, the surfactant did not appear to interact directly with the solid phase to inhibit binding of nucleic acids.

When DNA was bound to a GF/B membrane with salt, but without DTAB, and DTAB was incorporated in the chaotropic solution as the wash buffer (B+), DNA recovery from the membrane was significantly reduced compared to recovery from a GF/B membrane with no DTAB in the wash buffer (B−). These results suggest that the present of the cationic surfactant during the wash step removes DNA bound to the solid phase.

The effect of the cationic surfactant during binding to the solid phase in this experiment appeared related to the composition of the salt used during binding. When NaBr was the binding salt (compare NaBr C+ and NaBr C−), and when DTAB was included during binding (C+), recovery of DNA was significantly reduced compared to recovery with no DTAB during binding. However, when GuSCN was the binding salt, no significant reduction in recovery, was seen (compare GuSCN C+ and GuSCN C−). Therefore, in this experiment, depending on the salt composition, the presence of the cationic surfactant during binding may inhibit DNA binding to the solid phase.

As in A, pretreatment of the GF/B glass fiber filters with 5M salt (either NaBr or GuSCN) in the absence (D−) or presence (D+) of 1% DTAB did not appear to influence subsequent binding of nucleic acid.

The results in FIG. 16 indicate that in this experiment, DTAB did not tightly interact with the GF/B membrane to block DNA binding. In this work, the cationic surfactant, when present during the binding reaction, blocked binding of the DNA to the GF/B membrane. In addition, in this work, once the DNA was bound (in the absence of cationic detergent), the presence of the cationic surfactant during the subsequent wash steps resulted in bound DNA being removed from the membrane.

Example 19

To try to identify components of the protease digestion reaction that interfered with DNA binding to the glass fiber GF/B membrane, each of the following: $CaCl_2$, aurintricarboxylic acid, and Tween 20, was evaluated separately in a DNA binding reaction. Since binding and recovery of DNA may be affected by the presence of protein in samples, binding was performed in the presence or absence of 13% fetal bovine serum (FBS).

Figure 18:
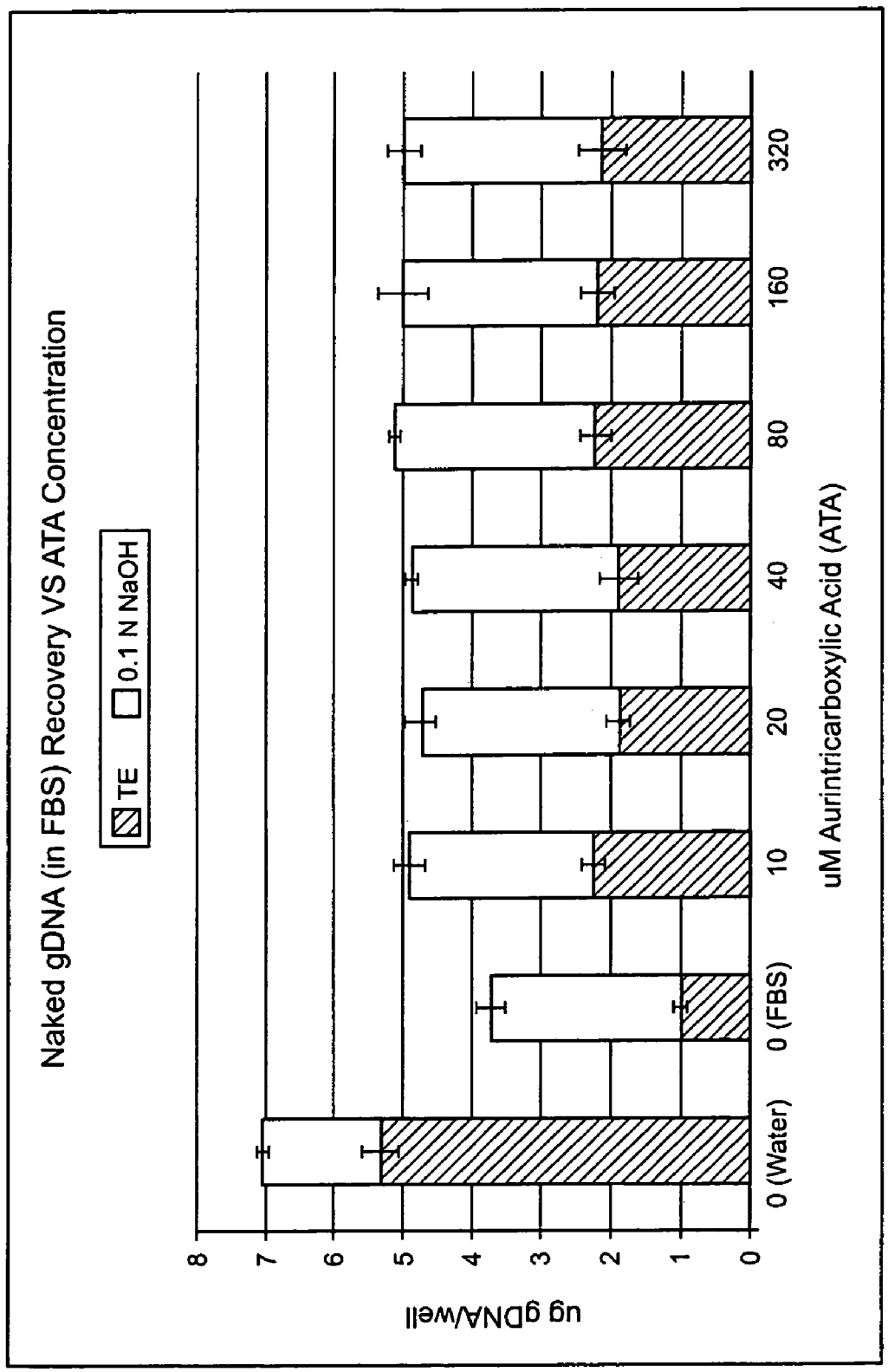
FIG. 18 shows the recovery of genomic DNA from buffer containing 1% fetal bovine serum as a function of aurintricarboxylic acid (ATA) concentration when eluting initially with TE followed by 100 mM NaOH. The values represent the cumulative release of nucleic acid following the two elution steps.
Figure 19:
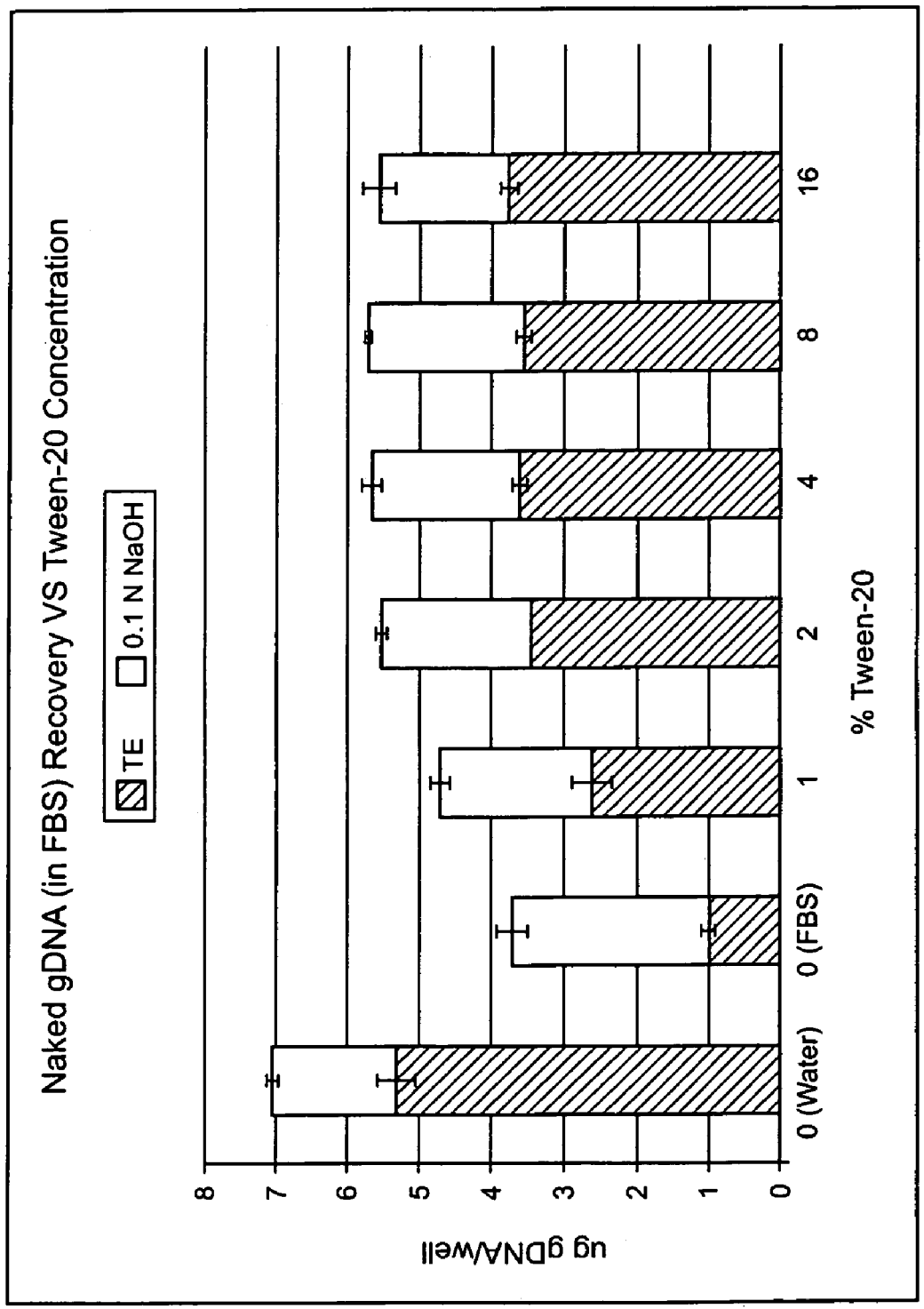
FIG. 19 shows the recovery of genomic DNA from buffer containing 1% fetal bovine serum as a function of Tween 20 concentration when eluting initially with TE followed by 100 mM NaOH. The values represent the cumulative release of nucleic acid following the two elution steps.
Figure 20:
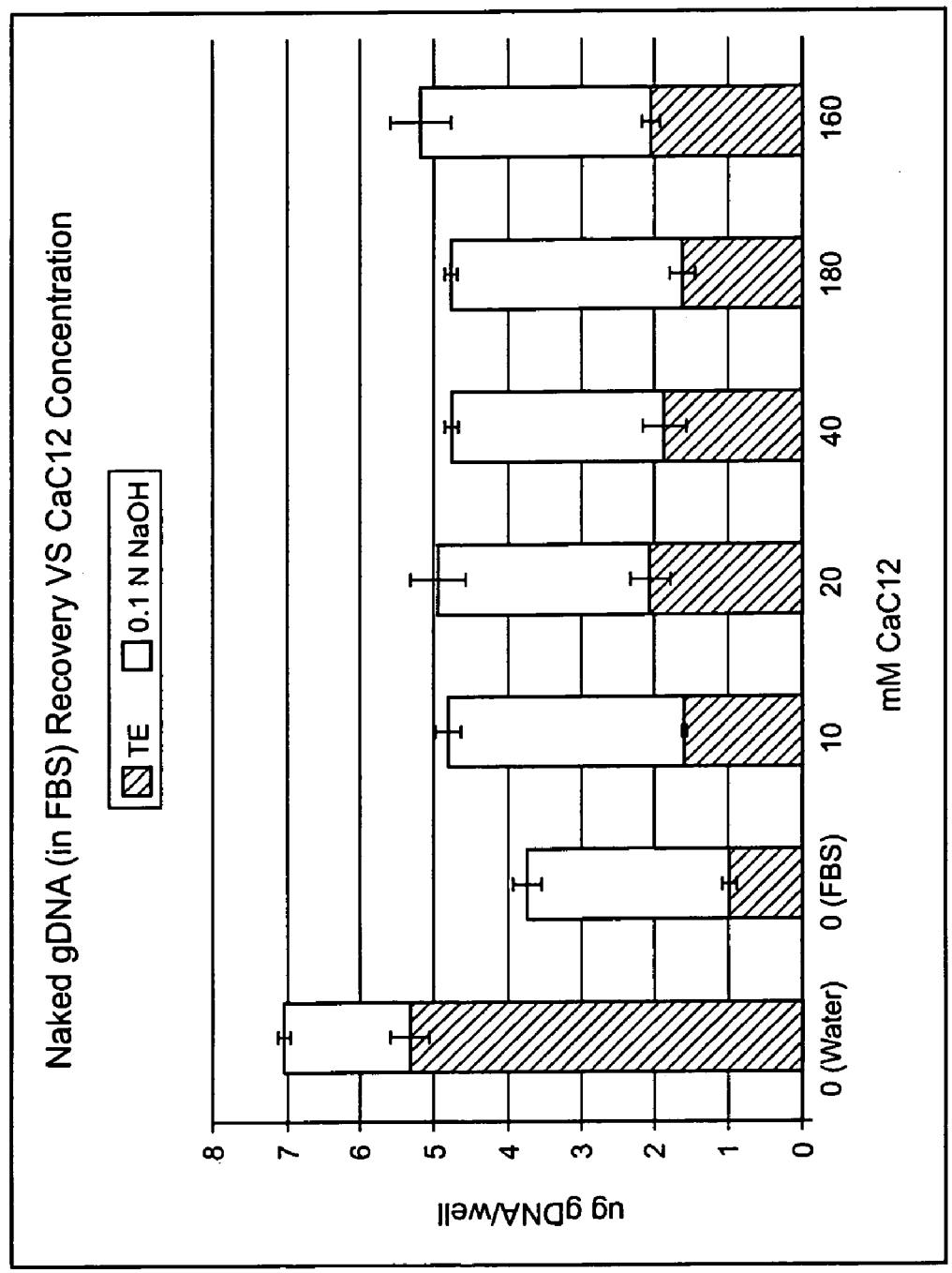
FIG. 20 shows the recovery of genomic DNA from buffer containing 1% fetal bovine serum as a function of $CaCl_2$ concentration when eluting initially with TE followed by 100 mM NaOH. The values represent the cumulative release of nucleic acid following the two elution steps.

In this work, addition of $CaCl_2$ (FIG. 20), aurintricarboxylic acid (FIG. 18), and Tween-20 (FIG. 19), at progressively higher concentrations all increased the recovery of DNA from the GF/B membrane. Aurintricarboxylic acid was evaluated at six concentrations from 10 µM to 320 µM at two-fold increments while DTAB and Tween 20 were both evaluated at five concentration levels from 1 to 16% at two-fold increments. DNA was first eluted with 200 µl of TE, followed by a separate elution with 100 µl of 0.1N NaOH. The maximum increase was, seen at 10 µM aurintricarboxylic acid (FIG. 18), 20% Tween-20 (FIG. 19), and 20 mM $CaCl_2$ (FIG. 20).

Figure 17:
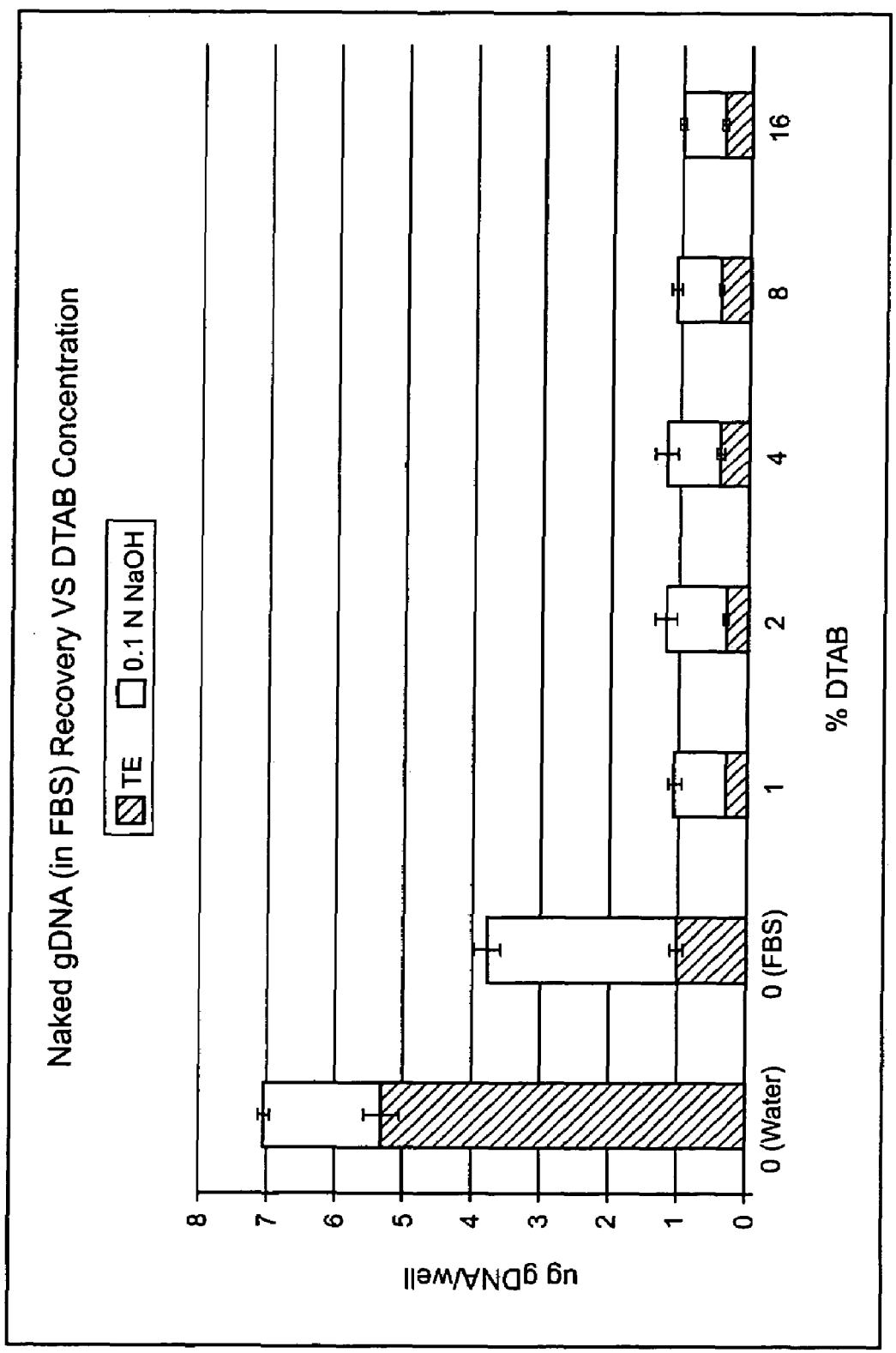
FIG. 17 shows the recovery of genomic DNA from buffer containing 1% fetal bovine serum as a function of DTAB concentration when eluting initially with TE followed by 100 mM NaOH. The values represent the cumulative release of nucleic acid following the two elution steps.

In contrast, in this work, the presence of the cationic surfactant dodecyltrimethylammonium bromide (DTAB) significantly reduced the recovery of DNA (FIG. 17). In addition, the DNA that was recovered was bound very tightly to the GF/B membrane, such that most of the DNA was only eluted with 0.1N NaOH for recovery.

Example 20

Having identified the cationic surfactant as a major component inhibiting DNA recovery, the ability of a nonionic surfactant to reverse the inhibitory effect was examined. Calf thymus genomic DNA (8 µg) was bound to the glass fiber GF/B membrane in the presence of 0%, 1% and 4% dodecyltrimethylammonium bromide (DTAB) with increasing concentrations of Tween 20.

The binding buffer also contained 5M GuSCN, 20 mM EDTA, and 50 mM MES (pH 6.0). DNA was first eluted with 200 µl of TE followed by a separate elution with 100 µl of 0.1N NaOH. All binding and elution steps were done at ambient temperature.

Figure 21:
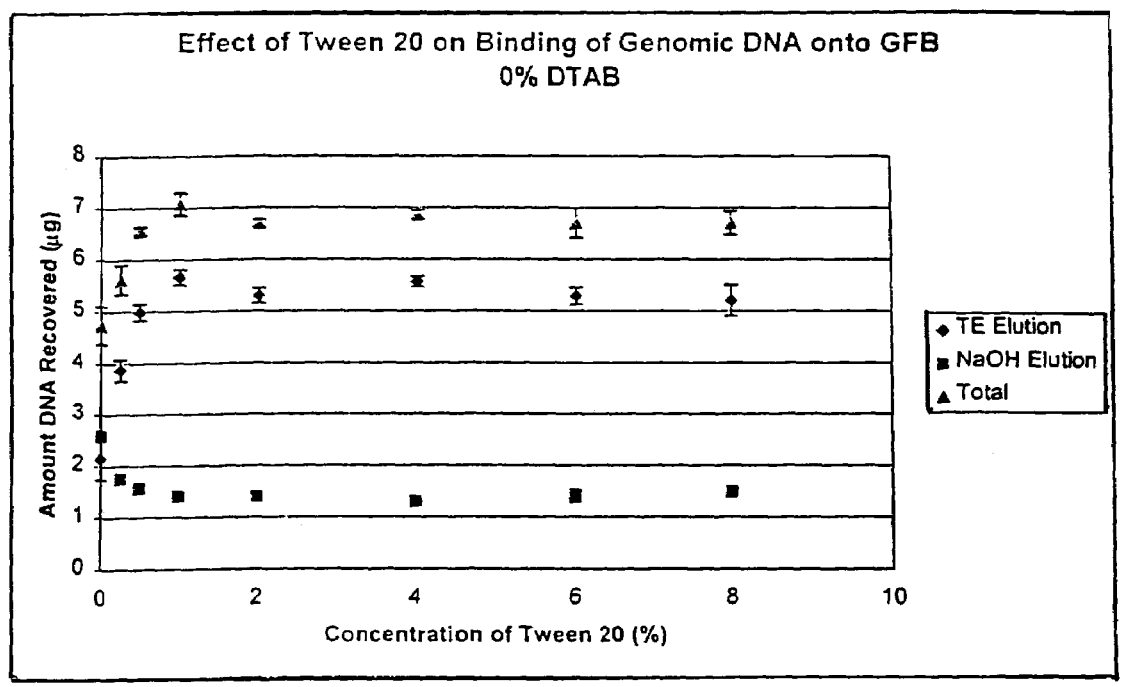
FIG. 21 shows the effect of Tween 20 concentration on binding of genomic DNA to GF/B filters in the presence of 3.75 M guanidinium thiocyanate lacking DTAB. The values represent the amount of nucleic acid released upon elution with TE, 100 mM NaOH, and the net amount eluted by under the two conditions.

In the absence of any cationic surfactant (0% DTAB), but in increasing Tween 20 concentrations, DNA recovery was observed without any of the nonionic surfactant (FIG. 21). The amount of DNA recovered increased significantly when the concentration of Tween, 20 was increased to at least 1% (FIG. 21).

Figure 22:
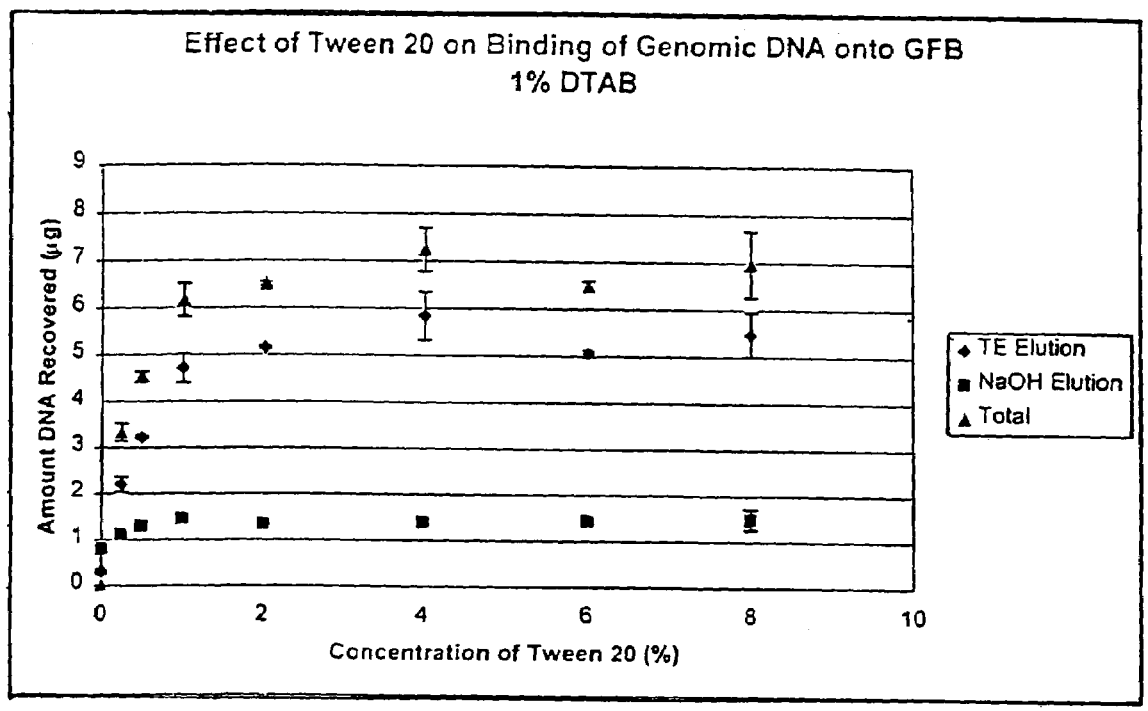
FIG. 22 shows the effect of Tween 20 concentration on binding of genomic DNA to GF/B filters in the presence of 3.75 M guanidinium thiocyanate and 1% DTAB. The values represent the amount of nucleic acid released upon elution with TE, 100 mM NaOH and the net amount eluted by under the two conditions.
Figure 23:
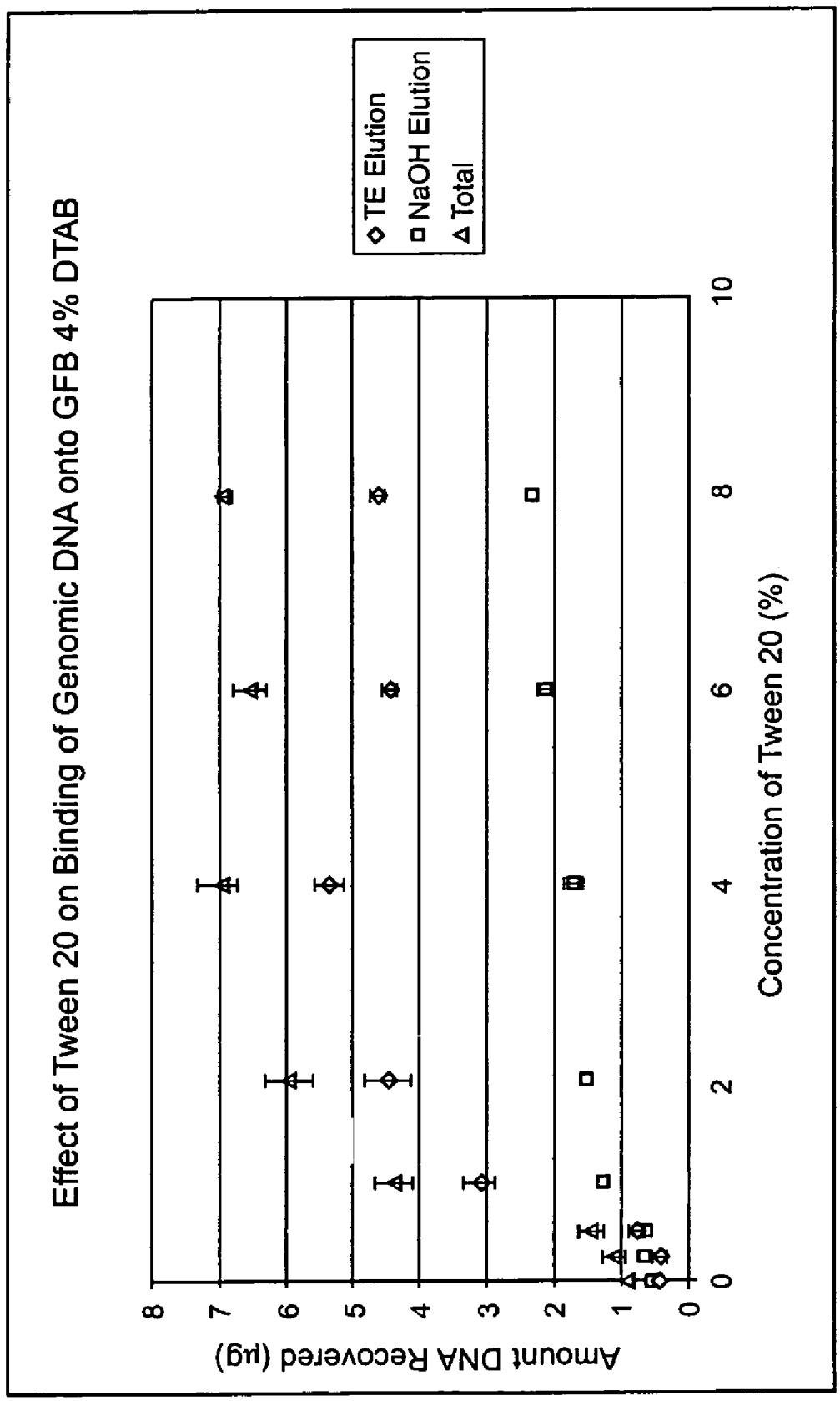
FIG. 23 shows the effect of Tween 20 concentration on binding of genomic DNA to GF/B filters in the presence of 3.75 M guanidinium thiocyanate and 4% DTAB. The values represent the amount of nucleic acid released upon elution with TE, 100 mM NaOH, and the net amount eluted by under the two conditions.
Figure 24:
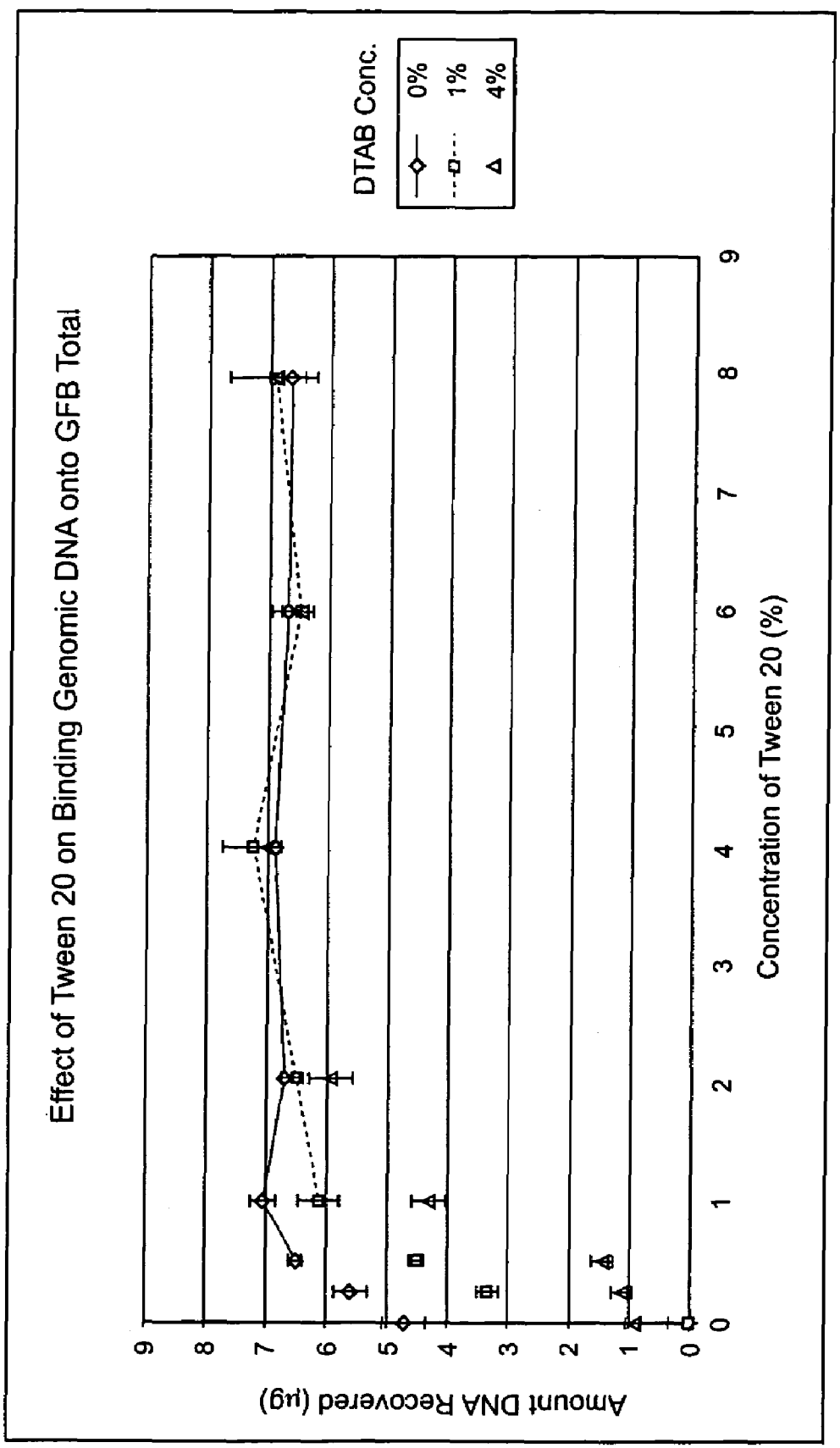
FIG. 24 shows the effect of Tween 20 on binding of genomic DNA to GF/B filters in the presence of the indicated DTAB concentrations, and elution with TE, followed by elution with NaOH.
Figure 25:
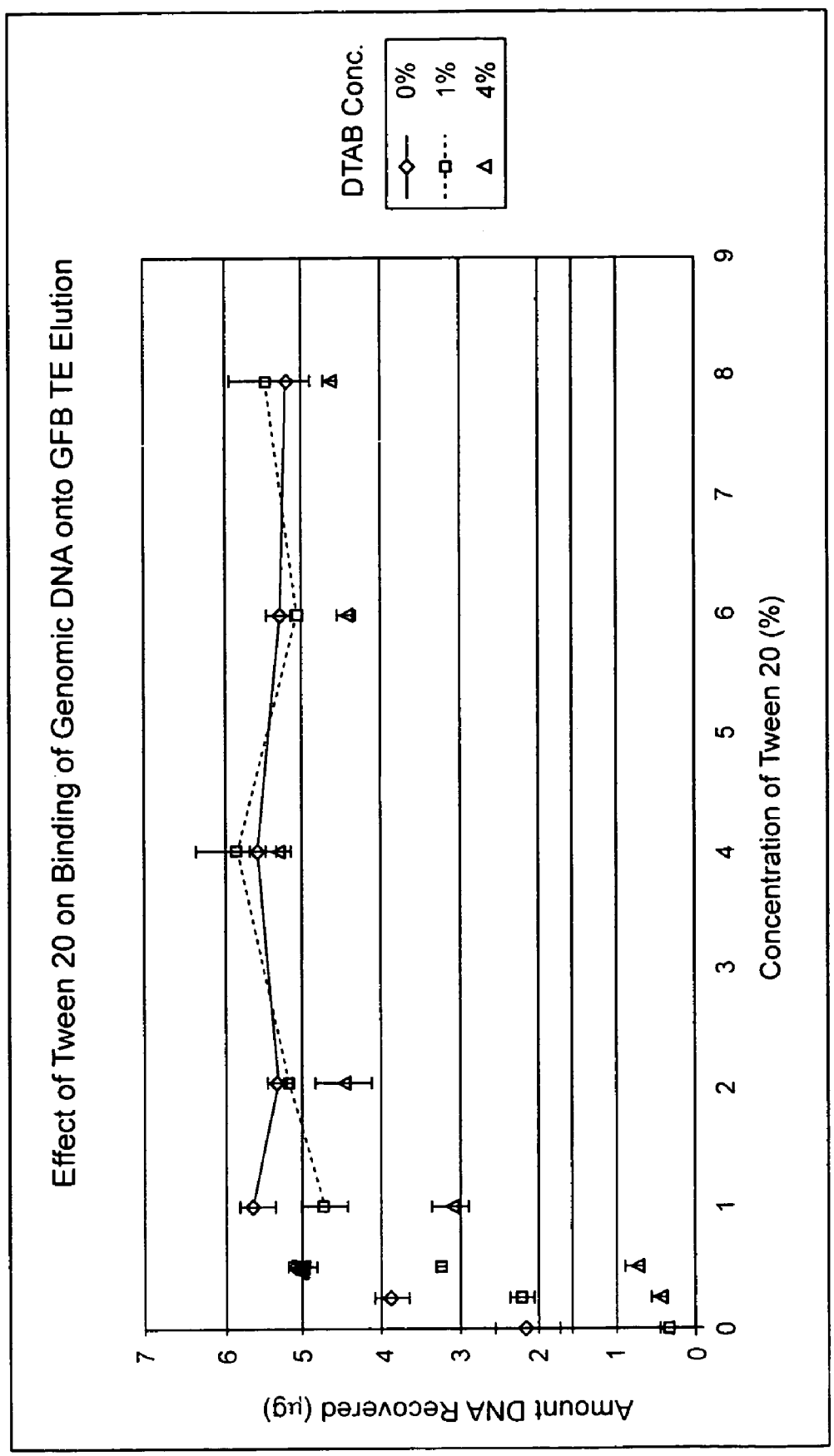
FIG. 25 shows the effect of Tween 20 concentration on binding of genomic DNA to GF/B filters in the presence of the indicated DTAB concentrations and recovery by elution with TE.

In the presence of 1% DTAB, DNA recovery from the filter was completely inhibited in the absence of Tween-20 (FIG. 22). Addition of Tween 20 to a concentration of at least 2% substantially blocked the inhibitory effect of the cationic surfactant (FIG. 22). In the presence of 4% DTAB, a concentration of at least 4% Tween-20 substantially blocked the inhibitory effect of the cationic surfactant (FIG. 23). In this work, when the appropriate amount of Tween-20 was added to the binding reaction, the amount of genomic DNA recovered from the glass fiber GF/B filter was not influenced by the presence of the cationic surfactant (FIG. 24). In addition, most of the bound DNA was recovered by a TE elution, and did not require an alkaline elution buffer (FIG. 25).

Example 21

Having identified conditions which resulted in binding of genomic DNA to glass fiber GF/B membranes in the presence of certain components of a tissue maceration method, the ability to isolate DNA from rat tail tissue was examined. In this example, two glass fiber membranes, GF/B and GF/D, were examined.

Figure 28:
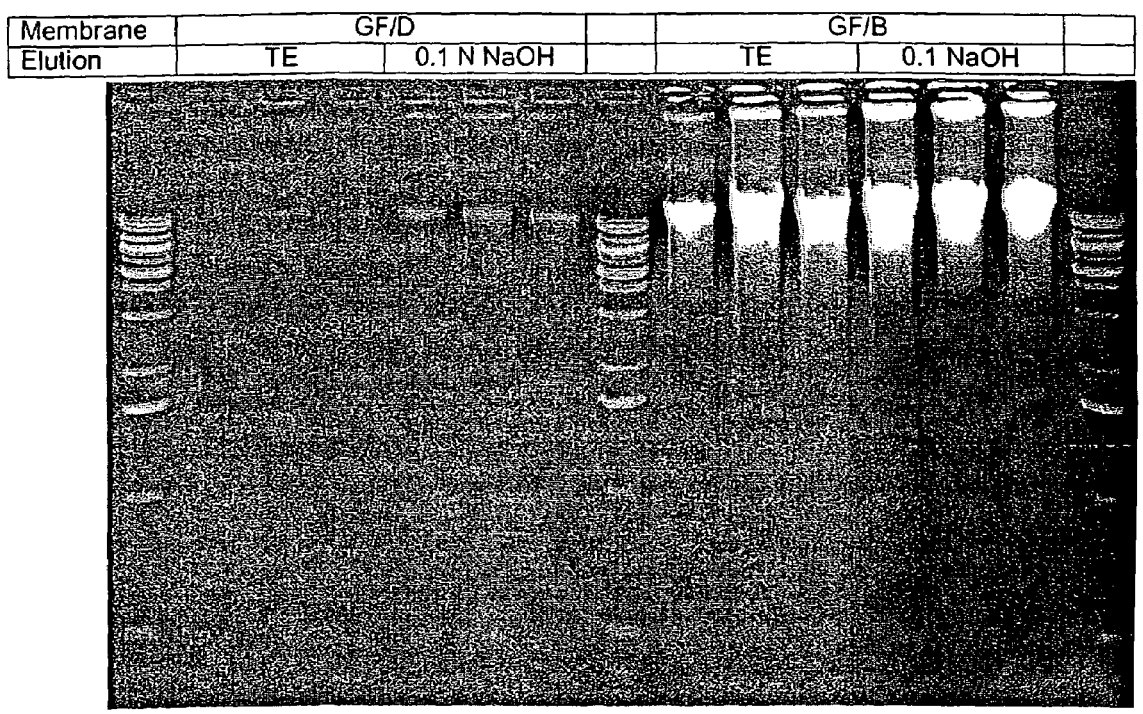
FIG. 28 depicts genomic DNA from 50 mg rat tail sections digested with 1 mg of Proteinase K and 1% DTAB, and bound to GF/B or GF/D filters in the presence of 3.75M GuSCN and 4.5% Tween 20. The genomic DNA was eluted with 150 µl of TE followed by elution with 0.01N NaOH. Of the eluate, 20 µl (14% of the total sample) was used for gel electrophoresis on 1% agarose.

Rat tail sections (50 mg) were digested in microfuge tubes containing 200 µl of a solution comprising 1 mg of Proteinase K, 1% DTAB, 100 mM Tris-HCl (pH 8.0), 20 µM ATA, and 20 mM $CaCl_2$. The reaction tubes were incubated at 65° C. with mixing (Eppendorf Thermomixer Model 5436) until all the samples were digested. It took 45 to 50 minutes to reduce the rat tail sections to a cloudy solution containing undigested bone and hair. The digests were then clarified by adding 600 µl of binding solution containing 5M GuSCN, 50 mM MES (pH 6.0), 20 mM EDTA, and 6% Tween 20. The released DNA was then bound to GF/B or GF/D filter membranes by transferring the solution into the filter leaving the bones and undigested particulates at the bottom of the tube. Following vacuum-mediated evacuation of the samples on an ABI Prism 6100, the filters were washed with 90% ethanol. The genomic DNA was eluted with either 150 µl of TE or 0.01N NaOH solutions. To visualize the integrity of the recovered DNA, 20 µl of the resulting eluate was electrophoresed on a 1% agarose gel stained with ethidium bromide (FIG. 28).

Figure 26:
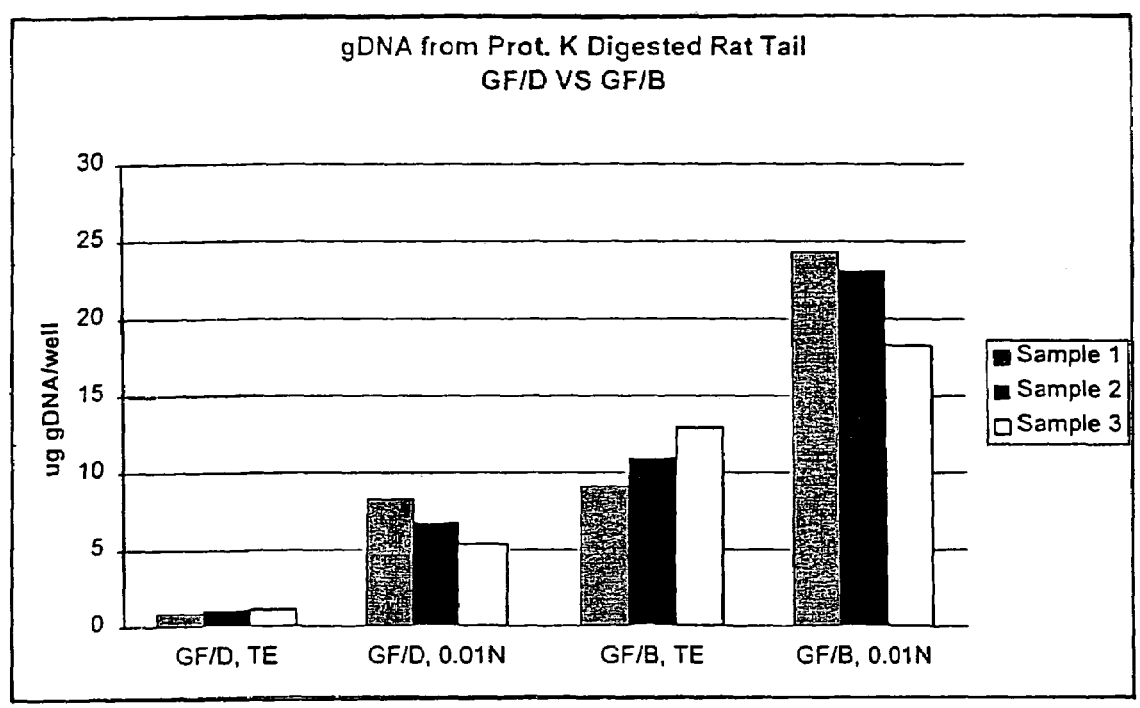
FIG. 26 shows the genomic DNA recovery from rat tails (~50 mg) with either GF/B or GF/D glass filters, and using either 0.01N NaOH or TE.
Figure 27:
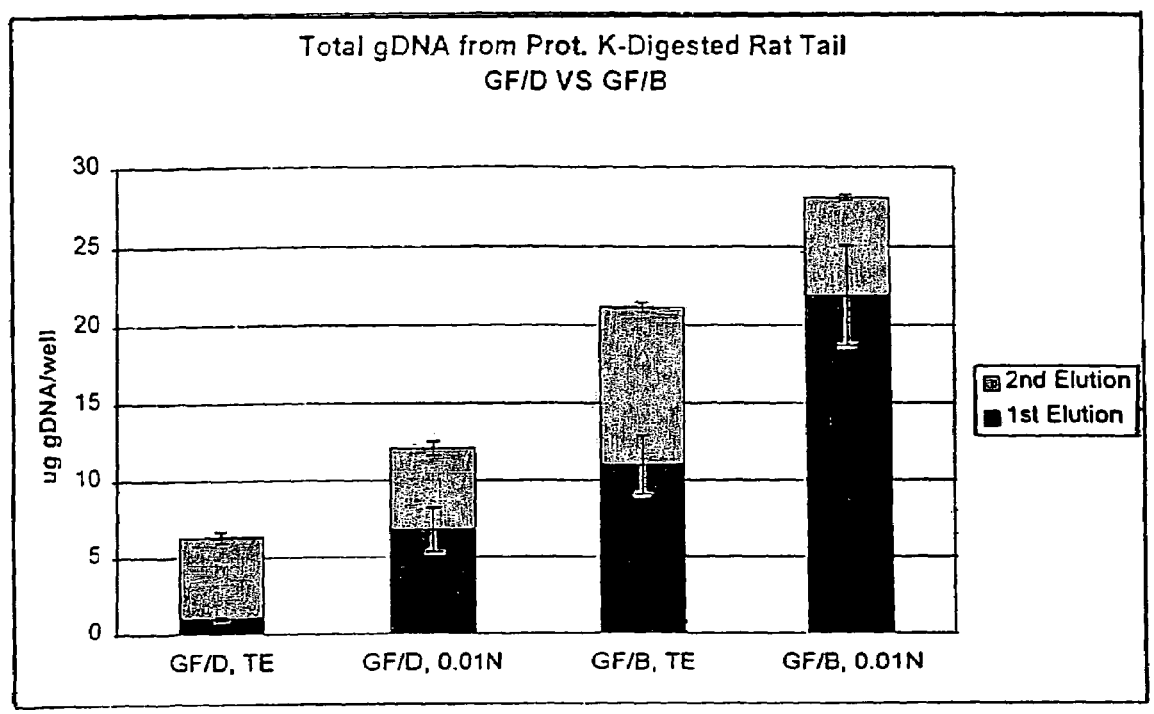
FIG. 27 shows the total genomic DNA recovered from rat tails (~50 mg) after a second elution with 0.1N NaOH from GF/B or GF/D glass fiber filters initially eluted with 0.01N NaOH or TE.

In this work, the glass fiber filter GF/B was superior to GF/D for recovery of genomic DNA (FIG. 26). A greater amount of DNA was recovered when eluted with 0.01N NaOH, compared to TE. Although most of the DNA was recovered from the membrane with 0.01 N NaOH, some DNA remained on the filter, as seen by further elution with 0.1 N NaOH (FIG. 27). The recovered DNA was of high molecular weight, as indicated in FIG. 28.

Example 22

The process from Example 21 was used to isolate genomic DNA from several rat tissues and mouse tail. Fifty milligram sections of rat muscle, liver, lung, pancreas, kidney, brain, small intestine, and tail, and 50 mg sections of mouse tail were placed in the microfuge tubes containing 200 µl of digestion solution. The digestion solution comprised 1 mg of Proteinase K, 1% DTAB, 100 mM Tris-HCl (pH 8.0), 20 µM ATA, and 20 mM CaCl$_2$.

Three identical samples were processed for each tissue type. The reaction tubes were incubated for 60 minutes at 65° C. with mixing (Eppendorf Thermomixer Model 5436). The digestion time for each tissue was noted and at the end of 60 minutes, the amount of undigested tissue was determined. The amount of time it takes to resolubilized 50 mg of various rodent tissues is presented in Table 14.

TABLE 14

| Tissue Sample | Digestion Time (min) |
| --- | --- |
| Rat Small Intestine | 45 |
| Rat Brain | 60* |
| Rat Lung | 55 |
| Rat Liver | 60* |
| Rat Kidney | 36 |
| Rat Skeletal Muscle | 60* |
| Rat Pancreas | 40 |
| Rat Tail | 50 |
| Mouse Tail | 40 |

*1 to 3 mg of tissue left undigested after 60 min incubation at 60° C.

As shown in Table 14, most of the tissues were effectively digested in less than one hour. Digestion of liver, brain and kidney were about 95% complete after one hour.

Figure 30:
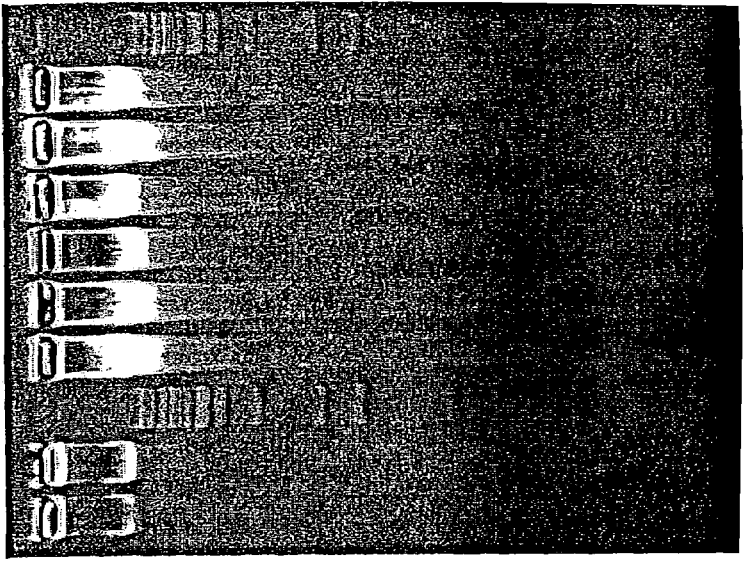
FIG. 30 depicts genomic DNA from 50 mg sections of rat tissues and a 35 mg mouse tail section digested with 1 mg of Proteinase K and 1% DTAB, and bound to GF/B filters in the presence of 3.75 M GuSCN and 4.5% Tween 20. The genomic DNA was eluted with 100 µl 0.01N NaOH followed by 100 µl of TE. For gel electrophoresis (on 1% agarose), 15 µl of each eluate was used.
Figure 30:
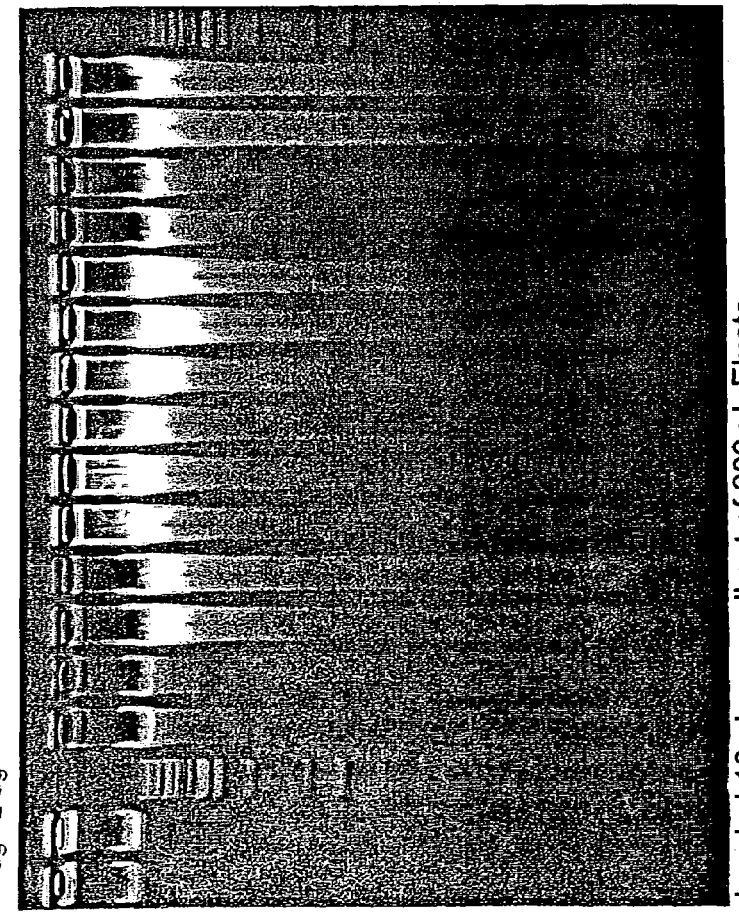

Following a 60 minute digestion, 600 µl of binding solution was then added to each sample. Binding solution contained 5M GuSCN, 50 mM MES (pH 6.0), 20 mM EDTA, and 6% Tween 20. The samples were then placed on GF/B filter membranes on an ABI Prism 6100. The filters were then washed with 90% ethanol. The genomic DNA was eluted with 100 µl of 0.01N NaOH solution and the first eluate was neutralized with 100 µl of 15 mM Tris-HCL, pH 7.0. Of the resultant 200 µl eluate, 20 µl was used for electrophoresis (10 µl per lane) on 1% agarose (FIG. 30). The DNA recovered was of high molecular weight, as seen in FIG. 30.

Figure 29:
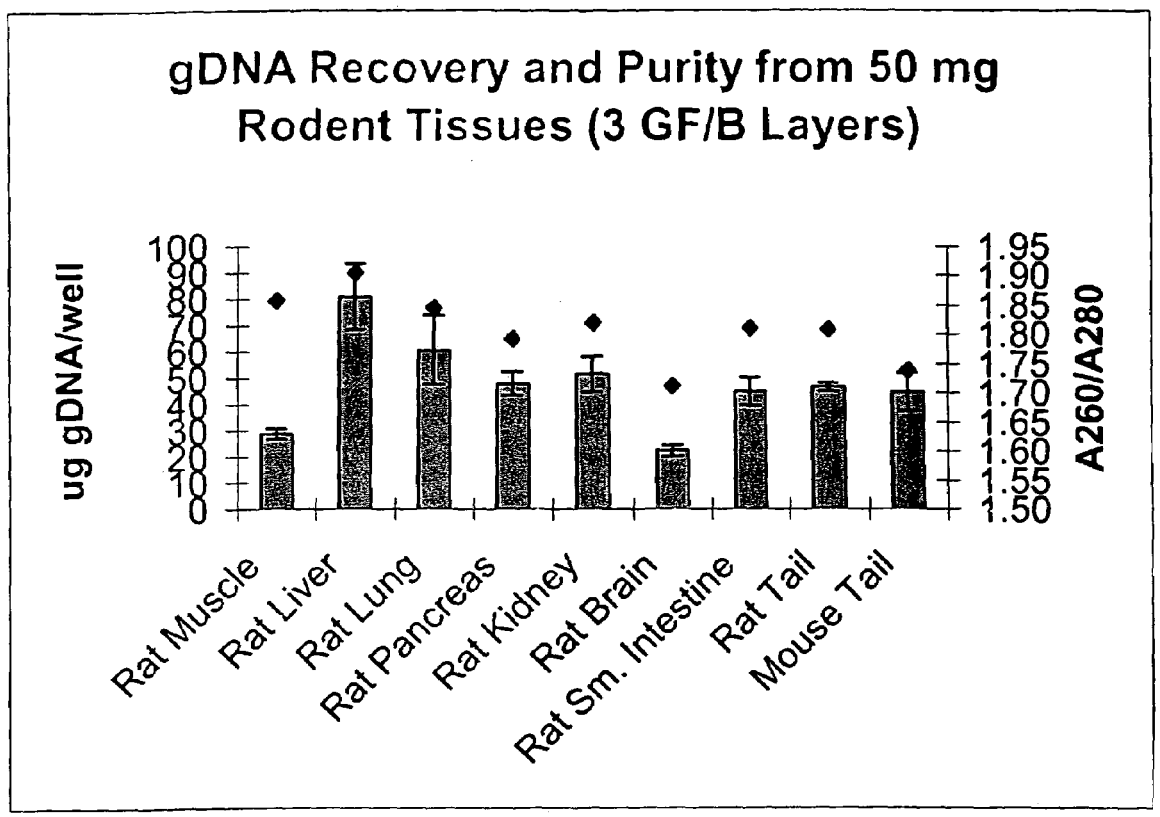
FIG. 29 shows the genomic DNA recovered from 50 mg of various rodent tissues. Tissue was digested with 1 mg of Proteinase K in the presence of 1% DTAB. The released nucieic acid was bound to GF/D membranes in the presence of 3.75 M guanidinium thiocyanate containing 4.5% Tween 20.

The total genomic DNA recovery is shown in FIG. 29. The total amount of genomic DNA, in µg of gDNA per well, is shown by the bars, as measured by the scale at the left of the graph. The relative purity of the DNA is shown by the filled diamonds, and is measured by the ratio of UV absorbance at 260 nm over 280 nm, shown by the scale at the right of the graph.

What is claimed is:

1. A method for isolating nucleic acids from a biological sample comprising:
    combining the sample with at least one cationic surfactant, at least one protease, and a buffer, to form a reaction composition;
    incubating the reaction composition at a temperature suitable for releasing nucleic acid from the biological sample; and
    isolating the released nucleic acid;
    wherein the method further comprises adding a polymer.

2. The method of claim 1, wherein the polymer is a polyethylene glycol.

3. A method for isolating nucleic acids from a biological sample comprising:
    combining the sample with at least one cationic surfactant, at least one protease, and a buffer, to form a reaction composition;
    incubating the reaction composition at a temperature suitable for releasing nucleic acid from the biological sample; and
    isolating the released nucleic acid;
    wherein the method further comprises adding a divalent cation capable of precipitating the nucleic acid, wherein the divalent cation is zinc.

4. A method for isolating nucleic acids from a biological sample comprising:
    combining the samnie with at least one cationic surfactant, at least one protease, a buffer and a ribonuclease inhibitor, to form a reaction composition;
    incubating the reaction composition at a temperature suitable for releasing nucleic acid from the biological sample; and
    isolating the released nucleic acid;
    wherein the nucleic acid is ribonucleic acid.

5. The method of claim 4, wherein the ribonuclease inhibitor comprises aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvic acid, formamide, copper, or zinc.

6. The method of claim 5, wherein the ribonuclease inhibitor is aurintricarboxylic acid.

7. A method for isolating nucleic acids from a biological sample comprising:
    combining the sample with at least one cationic surfactant, at least one protease, and a buffer, to form a reaction composition;
    incubating the reaction composition at a temperature suitable for releasing nucleic acid from the biological sample, wherein the reaction composition is incubated at a temperature of less than 60° C.; and
    isolating the released nucleic acid;
    wherein the nucleic acid is ribonucleic acid.

8. The method of claim 7, wherein the reaction composition is incubated at a temperature between 40° C. and 50° C.

9. A method for isolating nucleic acids from a biological sample comprising:
    combining the sample with at least one cationic surfactant, at least one protease, and a buffer, to form a reaction composition;
    incubating the reaction composition at a temperature suitable for releasing nucleic acid from the biological sample, wherein the reaction composition has a pH between 5.0 and 7.0; and
    isolating the released nucleic acid;
    wherein the nucleic acid is ribonucleic acid.

10. The method of claim 9, wherein the reaction composition is incubated at a temperature between 40° C. and 50° C., and wherein the reaction composition further comprises aurintricarboxylic acid.

11. A method for releasing nucleic acids from a biological sample comprising:
   combining the sample with at least one cationic surfactant, at least one protease, a buffer and a ribonuclease inhibitor, to form a reaction composition; and
   incubating the reaction composition at a temperature suitable for releasing the nucleic acids from the biological sample;
   wherein the nucleic acid is ribonucleic acid.

12. The method of claim 11, wherein the ribonuclease inhibitor comprises aurintricarboxylic acid, vanadylate ribonucleoside complexes, phenylglyoxal, p-hydroxyphenylglyoxal, polyamines, spermidine, 9-aminoacridine, iodoacetate, bentonite, poly[2'-O-(2,4-dinitrophenyl)]poly(adenyhlic acid), zinc sulfate, bromopyruvic acid, formamide, copper, or zinc.

13. The method of claim 12, wherein the ribonuclease inhibitor is aurintricarboxylic acid.

14. A method for releasing nucleic acids from a biological sample comprising:
   combining the sample with at least one cationic surfactant, at least one protease, and a buffer, to form a reaction composition; and
   incubating the reaction composition at a temperature suitable for releasing the nucleic acids from the biological sample, wherein the reaction composition is incubated at a temperature of less than 60° C.;
   wherein the nucleic acid is ribonucleic acid.

15. The method of claim 14, wherein the reaction composition is incubated at a temperature between 40° C. and 50° C.

16. A method for releasing nucleic acids from a biological sample comprising:
   combining the sample with at least one cationic surfactant, at least one protease, and a buffer, to form a reaction composition, wherein the reaction composition has a pH between 5.0 and 7.0; and
   incubating the reaction composition at a temperature suitable for releasing the nucleic acids from the biological sample;
   wherein the nucleic acid is ribonucleic acid.

17. The method of claim 16, wherein the reaction composition is incubated at a temperature between 40° C. and 50° C., and wherein the reaction composition further comprises aurintricarboxylic acid.

18. A kit for obtaining nucleic acid from a biological sample comprising at least one cationic surfactant; at least one protease; and at least one organic solvent for extracting the nucleic acids, precipitating the nucleic acids, or both extracting and precipitating the nucleic acids; wherein the organic solvent for extracting nucleic acids comprises phenol and the organic solvent for precipitating nucleic acids comprises isopropanol or ethanol.

19. A kit for obtaining nucleic acid from a biological sample comprising at least one cationic surfactant and at least one protease, wherein the kit further comprises a polymer.

20. A kit for obtaining nucleic acid from a biological sample comprising at least one cationic surfactant and at least one protease, wherein the kit further comprises at least one ribonuclease inhibitor.

21. The kit of claim 20, wherein the at least one ribonuclease inhibitor is aurintricarboxylic acid, vanadylate ribonucleoside complexes, phenylglyoxal, p-hydroxyphenylglyoxal, polyamines, spermidine, 9-aminoacridine, iodoacetate, Bentonite, poly[2'-O-(2,4-dinitrophenyl)]poly(adenyhlic acid), zinc sulfate, bromopyruvic acid, formamide, copper, or zinc.

22. A kit for obtaining nucleic acid from a biological samDle comprising at least one cationic surfactant and at least one protease, wherein the kit further comprises at least one solubilizing agent.

23. The kit of claim 22, wherein the solubilizing agent comprises 1-methyl 2 pyrolidinone, N-methyl pyrolidinone, pyrolidinone, dimethylformamide, or dimethylsulfoxide.

* * * * *